United States Patent
Otsu et al.

(10) Patent No.: US 10,177,322 B2
(45) Date of Patent: Jan. 8, 2019

(54) IRIDIUM COMPLEX, METHOD FOR PRODUCING IRIDIUM COMPLEX, ORGANIC ELECTROLUMINESCENT ELEMENT, DISPLAY DEVICE, AND LIGHTING DEVICE

(71) Applicant: Konica Minolta, Inc., Tokyo (JP)

(72) Inventors: Shinya Otsu, Musashino (JP); Motoaki Sugino, Akishima (JP); Hiroshi Kita, Hachioji (JP)

(73) Assignee: KONICA MINOLTA, INC., Tokyo (JP)

(*) Notice: Subject to any disclaimer, the term of this patent is extended or adjusted under 35 U.S.C. 154(b) by 0 days.

(21) Appl. No.: 15/645,345

(22) Filed: Jul. 10, 2017

(65) Prior Publication Data

US 2017/0309839 A1    Oct. 26, 2017

Related U.S. Application Data

(62) Division of application No. 14/917,801, filed as application No. PCT/JP2014/075688 on Sep. 26, 2014, now Pat. No. 9,748,501.

(30) Foreign Application Priority Data

Sep. 27, 2013 (JP) ................. 2013-201039

(51) Int. Cl.
| | |
|---|---|
| C07F 15/00 | (2006.01) |
| H01L 51/50 | (2006.01) |
| H01L 51/00 | (2006.01) |
| C09K 11/06 | (2006.01) |
| H05B 33/14 | (2006.01) |

(52) U.S. Cl.
CPC ...... H01L 51/0085 (2013.01); C07F 15/0033 (2013.01); C09K 11/06 (2013.01); H05B 33/14 (2013.01); C09K 2211/1007 (2013.01); C09K 2211/1011 (2013.01); C09K 2211/1014 (2013.01); C09K 2211/1029 (2013.01); C09K 2211/1044 (2013.01); C09K 2211/1088 (2013.01); C09K 2211/1092 (2013.01); C09K 2211/185 (2013.01); H01L 51/0067 (2013.01); H01L 51/0069 (2013.01); H01L 51/0072 (2013.01); H01L 51/0073 (2013.01); H01L 51/0074 (2013.01); H01L 51/0081 (2013.01); H01L 51/0094 (2013.01); H01L 51/5016 (2013.01)

(58) Field of Classification Search
CPC .................. C07F 15/00; H01L 51/50
USPC .............. 548/101; 313/504; 546/4
See application file for complete search history.

(56) References Cited

U.S. PATENT DOCUMENTS

| | | | |
|---|---|---|---|
| 6,097,147 A | 8/2000 | Baldo et al. | |
| 7,491,823 B2 | 2/2009 | Thompson et al. | |
| 2011/0057559 A1 | 3/2011 | Xia et al. | |
| 2014/0158998 A1* | 1/2014 | Noh et al. | ............ H01L 257/40 |

FOREIGN PATENT DOCUMENTS

| | | |
|---|---|---|
| JP | 2003113161 A | 4/2003 |
| JP | 2003113164 A | 4/2003 |
| JP | 2005112765 A | 4/2005 |
| JP | 2007504272 A | 3/2007 |
| JP | 2009500316 A | 1/2009 |
| JP | 2011052088 A | 3/2011 |
| JP | 2011068848 A | 4/2011 |
| JP | 2011222650 A | 11/2011 |
| WO | 0244189 A1 | 6/2002 |
| WO | 2004101707 A1 | 11/2004 |
| WO | 2007004113 A2 | 1/2007 |
| WO | 2009047993 A1 | 4/2009 |
| WO | 2011086089 A1 | 7/2011 |
| WO | 2012111548 A1 | 8/2012 |

OTHER PUBLICATIONS

Lo, S-C. et al.: Blue Phosphorescence from iridium(III) complexes at room temperature. Chem. Mater., vol. 18, pp. 5119-5129, 2006.*
M.A. Baldo, et al; High-efficiency fluorescent organic light-emitting devices using a phosphorescent sensitizer; Letters to Nature; vol. 43; Feb. 2000; pp. 750-753.
S. Lamansky, et al; Highly phosphorescent bis-cyclometalated iridium complexes: synthesis, photophysical . . . ; J. Am. Chem. Soc.; vol. 123; 2001; pp. 4304-4312.
M.A. Baldo, et al; Highly efficient phosphorescent emission from organic electroluminescent devices; Nature; vol. 395; Sep. 1998; pp. 151-154.
International Search Report dated Jan. 6, 2015 for PCT/JP2014/075688 and English translation.

* cited by examiner

*Primary Examiner* — Charanjit Aulakh
(74) *Attorney, Agent, or Firm* — Lucas & Mercanti, LLP

(57) ABSTRACT

Disclosed herein are an iridium complex having improved luminous efficiency and emission lifetime, a method for producing the same, an organic electroluminescent element using the iridium complex, and a display device and a lighting device that include the organic electroluminescent element. The iridium complex is contained in at least one organic layer sandwiched between an anode and a cathode of an organic electroluminescent element, and has a coefficient of external influence of 0.73 Å$^2$/MW or less as defined by the following definition equation:

Coefficient of external influence (Svdw)=Van der Waals surface area [Å$^2$]/molecular weight (MW).

10 Claims, 6 Drawing Sheets

LIGHT

LIGHT

US 10,177,322 B2

IRIDIUM COMPLEX, METHOD FOR PRODUCING IRIDIUM COMPLEX, ORGANIC ELECTROLUMINESCENT ELEMENT, DISPLAY DEVICE, AND LIGHTING DEVICE

CROSS REFERENCE TO RELATED APPLICATION

This application is a Divisional application of U.S. application Ser. No. 14/917,801 filed Mar. 9, 2016, which was a 371 of PCT/JP2014/075688 filed on Sep. 26, 2014 which, in turn, claimed the priority of Japanese Application No. 2013-201039 filed on Sep. 27, 2013, all applications are incorporated herein by reference.

TECHNICAL FIELD

The present invention relates to an iridium complex and a method for producing the same. Further, the present invention relates to an organic electroluminescent element using the iridium complex, and a display device and a lighting device that include the organic electroluminescent element. More specifically, the present invention relates to an iridium complex that is a regular octahedral transition metal complex-based phosphorescence-emitting compound having improved oxygen tolerance, and a method for producing the same.

BACKGROUND ART

An organic electroluminescent element (hereinafter, also referred to as organic EL element) is a light-emitting element that has a structure in which a light-emitting layer containing a luminescent compound is sandwiched between a cathode and an anode and that utilizes emission of light (fluorescence•phosphorescence) caused by deactivation of excitons generated by recombination of holes injected from the anode and electrons injected from the cathode by the application of an electric field within the light-emitting layer. Further, an organic EL element is an all-solid-state element that includes organic material films with a thickness of only about a submicron level provided between electrodes, and can emit light at a voltage of about several volts to several tens of volts, and is therefore expected to be used for next-generation flat-panel displays and lighting.

Princeton University has developed an organic EL element for practical use and has reported an organic EL element using phosphorescence emission from an excited triplet state (see, for example, Non-Patent Literature 1), and since then, materials that emit phosphorescence at room temperature have been actively studied (see, for example, Patent Literature 1 and Non-Patent Literature 2).

Further, an organic EL element utilizing phosphorescence emission can achieve, in principle, luminous efficiency about 4 times higher than that of a conventional organic EL element utilizing fluorescence emission, and therefore development of materials thereof as well as research and development of layer structures and electrodes of light-emitting elements has been performed all over the world. For example, many compounds, mainly, heavy metal complexes such as iridium complexes have been synthesized and studied (see, for example, Non-Patent Literature 3).

As described above, a phosphorescence emission system is a very high-potential system. However, an organic EL element utilizing phosphorescence emission is significantly different from an organic EL element utilizing fluorescence emission in that how to control the position of a luminescent center, especially, how stably light can be emitted by recombination within a light-emitting layer is an important technical issue to be solved to improve the efficiency and lifetime of the element.

Under the circumstances, a multi-layered element is well-known in recent years, which has a light-emitting layer, a hole transport layer provided adjacent to the anode side of the light-emitting layer, and an electron transport layer provided adjacent to the cathode side of the light-emitting layer (see, for example, Patent Literature 2). As the light-emitting layer, a mixed layer using a host compound and a phosphorescence-emitting compound as a dopant is often used.

On the other hand, from the viewpoint of material, materials that have high carrier transportability and are thermally or electrically stable are required. Particularly, a blue phosphorescent compound itself has high triplet excitation energy ($T_1$), and therefore in order to utilize blue phosphorescence emission, development of applicable peripheral materials and precise control of a luminescent center are strongly required.

As a typical blue phosphorescence-emitting compound, FIrpic (Bis[2-4,6-difluorophenyl)pyridinato-$C^2$,N] (picolinato)iridium(III)) is known, which achieves a shorter emission wavelength by fluorine substitution of phenylpyridine as a primary ligand and use of picolinic acid as an auxiliary ligand. Such a dopant is combined with carbazole derivatives or triarylsilanes as host compounds to achieve higher efficiency of elements, which however significantly deteriorates the emission lifetime of the elements. Therefore, such trade-off needs to be improved.

As a means for improving the trade-off, improvement in the thermal stability of a metal complex by caging has been considered. For example, there is a technique in which the generation of degradation products during vapor deposition is prevented by improving the thermal stability of a metal complex as a material for organic EL elements to improve the performance of the elements.

Further, metal complexes having a specific ligand have been found in recent years as high-potential blue phosphorescent compounds (see, for example, Patent Literatures 3 and 4).

Improvement in the performance of a phosphorescence-emitting material for phosphorescent organic EL elements influences the achievement of full-scale use of organic EL elements for lighting and electronic displays, and is therefore an issue of greatest concern in the field of organic EL materials, but development of a phosphorescent material having improved performance is a difficult issue.

CITATION LIST

Patent Literatures

Patent Literature 1: U.S. Pat. No. 6,097,147
Patent Literature 2: JP 2005-112765 A
Patent Literature 3: US 2011/0057559 A
Patent Literature 4: WO 2011/086089 A

Non-Patent Literature

Non-Patent Literature 1: M. A. Baldo et al., nature, vol. 395, pp. 151 to 154 (1998)
Non-Patent Literature 2: M. A. Baldo et al., nature, vol. 403, no. 17, pp. 750 to 753 (2000)

Non-Patent Literature 3: S. Lamansky et al., J. Am. Chem. Soc., vol. 123, p. 4304 (2001)

SUMMARY OF INVENTION

Technical Problem

In view of the above problems and circumstances, it is an object of the present invention to provide an iridium complex having improved luminous efficiency and emission lifetime, a method for producing the same, an organic electroluminescent element using the iridium complex, and a display device and a lighting device that include the organic electroluminescent element.

Solution to Problem

In order to achieve the above object, the present inventors have studied the causes of the above problems, and as a result, have found that when an iridium complex contained in at least one organic layer sandwiched between an anode and a cathode of an organic electroluminescent element has a coefficient of external influence of 0.73 Å²/MW or less as defined by the following definition equation, the iridium complex is less likely to be affected by oxygen, which leads to improvement in luminous efficiency and emission lifetime. This finding has led to the completion of the present invention.

More specifically, the above object of the present invention is achieved by the following means.

1. An iridium complex contained in at least one organic layer sandwiched between an anode and a cathode of an organic electroluminescent element, the iridium complex having a coefficient of external influence of 0.73 Å²/MW or less as defined by the following definition equation:

Coefficient of external influence (Svdw)=Van der Waals surface area [Å²]/Molecular weight (MW).

2. The iridium complex according to the above 1, which has a partial structure represented by the following general formula (1):

[Chemical Formula 1]

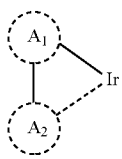

General Formula (1)

(wherein $A_1$ is an aromatic ring, and $A_2$ is a nitrogen atom-containing aromatic ring).

3. The iridium complex according to the above 2, wherein the partial structure represented by the general formula (1) is a partial structure represented by any one of the following general formulas (2) to (5):

[Chemical Formula 2]

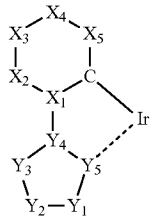

General Formula (2)

(wherein a carbon atom and $X_1$ to $X_5$ are a group of atoms forming a 6-membered aromatic ring, and $Y_1$ to $Y_5$ are a group of atoms forming a nitrogen atom-containing 5-membered aromatic ring).

[Chemical Formula 3]

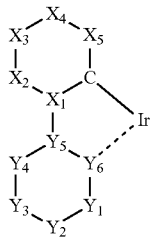

General Formula (3)

(wherein a carbon atom and $X_1$ to $X_5$ are a group of atoms forming a 6-membered aromatic ring, and $Y_1$ to $Y_6$ are a group of atoms forming a nitrogen atom-containing 6-membered aromatic ring).

[Chemical Formula 4]

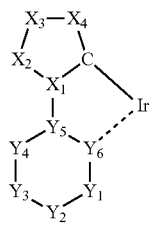

General Formula (4)

(wherein a carbon atom and $X_1$ to $X_4$ are a group of atoms forming a 5-membered aromatic ring, and $Y_1$ to $Y_6$ are a group of atoms forming a nitrogen atom-containing 6-membered aromatic ring).

[Chemical Formula 5]

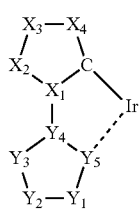

General Formula (5)

(wherein a carbon atom and $X_1$ to $X_4$ are a group of atoms forming a 5-membered aromatic ring, and $Y_1$ to $Y_5$ are a group of atoms forming a nitrogen atom-containing 5-membered aromatic ring).

4. The iridium complex according to the above 3, wherein in the general formula (2) or (3), the group of atoms consisting of a carbon atom and $X_1$ to $X_5$ forms a benzene ring or a pyridine ring.

5. The iridium complex according to the above 3, wherein in the general formula (2) or (5), the nitrogen-containing group of atoms consisting of $Y_1$ to $Y_5$ forms an imidazole ring, a pyrazole ring, or a triazole ring.

6. The iridium complex according to any one of the above 3 to 5, wherein in the general formula (2) or (3), at least one of the atoms represented by $X_5$ and $Y_1$ is a carbon atom having a substituent group, and wherein the substituent group is a halogen atom, a trifluoromethyl group, or a pentafluorophenyl group.

7. The iridium complex according to any one of the above 3 to 5, wherein in the general formula (4) or (5), at least one of the atoms represented by $X_4$ and $Y_1$ is a carbon atom having a substituent group, and wherein the substituent group is a halogen atom, a trifluoromethyl group, or a pentafluorophenyl group.

8. A method for producing the iridium complex according to anyone of the above 1 to 7, including synthesizing the iridium complex by a solvent-free reaction using, as an alternative to a reaction solvent, an organic compound serving as a ligand of the iridium complex.

9. The iridium complex production method according to the above 8, wherein a 6-coordinated iridium complex is formed by coordination of ligands to iridium, and then a substituent group is introduced into the ligands of the iridium complex.

10. An organic electroluminescent element including the iridium complex according to any one of the above 1 to 7.

11. A display device including the organic electroluminescent element according to the above 10.

12. A lighting device including the organic electroluminescent element according to the above 10.

Advantageous Effects of Invention

According to the present invention, it is possible to provide an iridium complex having improved luminous efficiency and emission lifetime, a method for producing the same, an organic electroluminescent element using the iridium complex, and a display device and a lighting device that include the organic electroluminescent element.

The occurrence mechanism of the effects of the present invention and the action mechanism of the present invention are not clear, but are supposed as follows.

It is known that an iridium complex (hereinafter, also referred to as Ir complex) used in organic EL elements causes poor emission due to the presence of oxygen. The present inventors have investigated the molecular design of an iridium complex that is less likely to be affected by oxygen, and as a result have found that an iridium complex can be shielded from oxygen by coordinating ligands in such a manner that iridium as a central metal is surrounded by the ligands. More specifically, the present inventors have found that when the value of a parameter (coefficient of external influence (Svdw)) obtained by dividing the Van der Waals surface area of an iridium complex having an optimized structure calculated by quantum computing by the molecular weight of the iridium complex is 0.73 Å$^2$/MW or less, the iridium complex is less likely to be affected by oxygen.

The reason for this is considered to be that when the value of Van der Waals surface area per molecular weight is equal to or less than the predetermined value, the proportion of atoms per volume occupied by the iridium complex is high and the iridium complex has a structure into which oxygen cannot enter, and therefore iridium as a central metal is not affected by oxygen.

DESCRIPTION OF EMBODIMENTS

Figure 1:
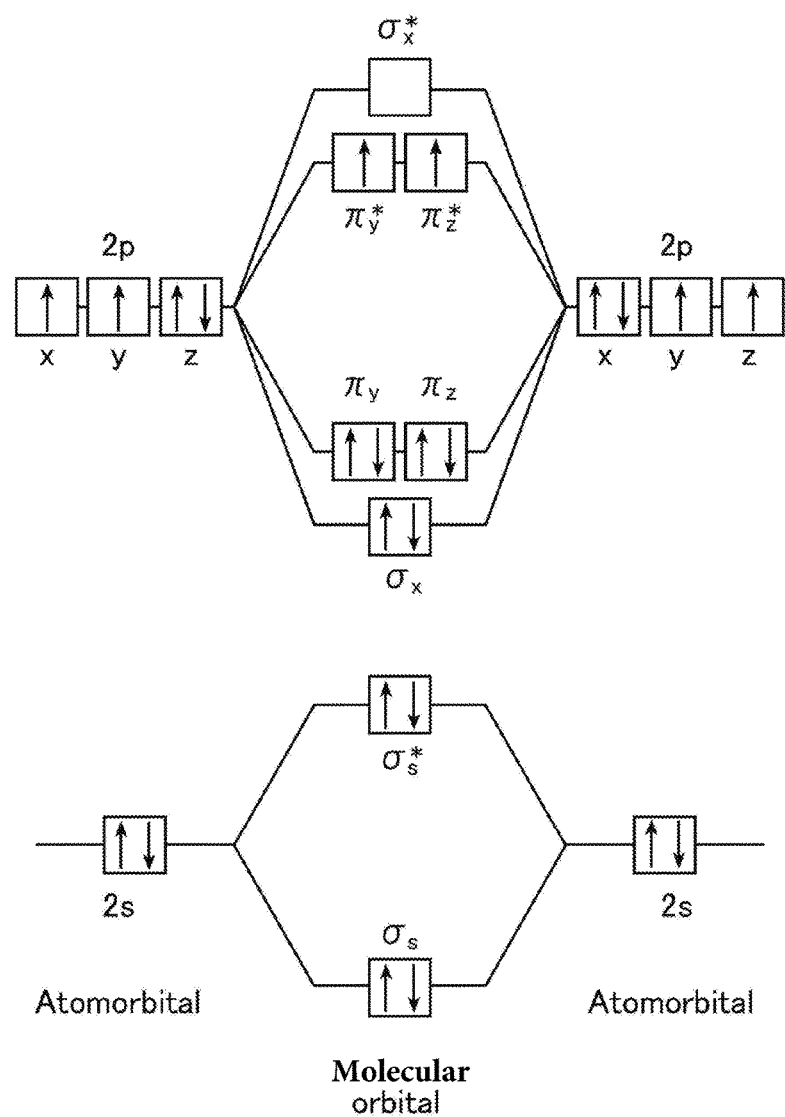
FIG. 1 is a diagram of the molecular orbital of triplet oxygen.

An iridium complex according to the present invention is an iridium complex to be contained in at least one organic layer sandwiched between an anode and a cathode of an organic electroluminescent element, and has a coefficient of external influence of 0.73 Å$^2$/MW or less as defined by the above definition equation. This is a technical feature common to the inventions disclosed herein.

From the viewpoint of the occurrence of the effects of the present invention, it is preferred that the iridium complex according to an embodiment of the present invention has a partial structure represented by the above general formula (1).

Further, from the viewpoint that iridium as a central metal is less likely to be affected by oxygen, it is preferred that the partial structure represented by the above general formula (1) is a partial structure represented by any one of the above general formulas (2) to (5).

Further, from the viewpoint of the occurrence of the effects of the present invention, it is preferred that, in the above general formula (2) or (3), the group of atoms consisting of a carbon atom and $X_1$ to $X_5$ forms a benzene ring or a pyridine ring.

Further, from the viewpoint of the occurrence of the effects of the present invention, it is preferred that, in the above general formula (2) or (5), the nitrogen-containing group of atoms consisting of $Y_1$ to $Y_5$ forms an imidazole ring, a pyrazole ring, or a triazole ring.

Further, from the viewpoint of the occurrence of the effects of the present invention, it is preferred that, in the above general formula (2) or (3), at least one of the atoms represented by $X_5$ and $Y_1$ is a carbon atom having a substituent group, and the substituent group is a halogen atom, a trifluoromethyl group, or a pentafluorophenyl group.

Further, from the viewpoint of the occurrence of the effects of the present invention, it is preferred that, in the above general formula (4) or (5), at least one of the atoms represented by $X_4$ and $Y_1$ is a carbon atom having a substituent group, and the substituent group is a halogen atom, a trifluoromethyl group, or a pentafluorophenyl group.

A method for producing the iridium complex according to the present invention preferably includes synthesizing the iridium complex by a solvent-free reaction using, as an alternative to a reaction solvent, an organic compound serving as a ligand of the iridium complex, from the viewpoint that bulky ligands can be coordinated to iridium as a central metal so that the iridium is less likely to be externally affected.

Further, from the viewpoint of synthesis, it is preferred that a 6-coordinated iridium complex is formed by coordinating ligands to iridium, and then a substituent group is introduced into the ligands of the iridium complex.

The iridium complex according to the present invention can be appropriately used in an organic electroluminescent element. This makes it possible to improve luminous efficiency and emission lifetime.

The organic electroluminescent element according to the present invention can be appropriately used in a display device. This makes it possible to improve luminous efficiency and emission lifetime.

The organic electroluminescent element according to the present invention can be appropriately used in a lighting device. This makes it possible to improve luminous efficiency and emission lifetime.

Hereinbelow, the present invention, components thereof, and embodiments and aspects for carrying out the present invention will be described in detail. It is to be noted that "to" used between numerical values in this application means that values described before and after "to" are included as a lower limit and an upper limit, respectively.

Before the description of a main subject, the principle of light emission from an iridium complex and the structure of an iridium complex will be described which relate to the technical idea of the present invention.

Metal complexes having platinum or iridium as a central metal and appropriate ligands are widely used as phosphorescence-emitting compounds. The present invention is directed to a phosphorescence-emitting compound substantially unaffected by oxygen, in which a metal element is surrounded by ligands to be completely shielded from the influence of external elements. Therefore, the present invention excludes a planar 4-coordinated platinum (II) complex in which ligands are not coordinated above and below platinum (II) metal in a direction orthogonal to the plane of the complex.

The present invention is directed to a regular octahedral phosphorescence-emitting complex typified by an iridium (III) complex. Further, two or more ligands forming the complex are arranged to fill together the space around a central metal so that the central metal is completely shielded from the influence of oxygen or the like.

Therefore, the present invention relates to a metal complex capable of forming a luminescent thin film that shows little reduction in luminescence intensity even in the presence of oxygen or little change in the resistance value of a light-emitting layer during application of electric current with time and therefore has a very great industrial value.

The essence of the technique is to completely eliminate energy transfer between the phosphorescent iridium complex and an oxygen molecule, that is, to separate the phosphorescent iridium complex and oxygen by a distance at which energy transfer does not occur between them.

A prototype of such an organic EL element (type using a fluorescent material) was released in 1987. Further, an organic EL element using a phosphorescent material was released in 1998 which achieves high luminous efficiency by utilizing all singlet and triplet excitons for electroluminescence.

Fluorescence emission-type organic EL elements have already been applied not only to indicators and audio systems for cars but also to electronic displays for mobile phones and the like, and such cars and mobile phones are commercially available. Further, a phosphorescence emission-type organic EL device "Symfos (registered trademark) OLED-10K" was also commercialized by KONICA MINOLTA, INC. in October 2011, which is the world's-first all-phosphorescent lighting device, and its practicality has been demonstrated.

From the viewpoint of luminous efficiency, a phosphorescence emission system can achieve luminous efficiency theoretically four times higher than that of a fluorescence emission system, and is therefore preferred in terms of power consumption. However, blue phosphorescence emitters have high triplet energy, and therefore light-emitting elements that emit blue phosphorescence have a much shorter lifetime than those that emit phosphorescence of another color, which is the biggest factor in preventing the development of industry.

Further, green or red phosphorescence emitters as well as blue phosphorescence emitters are affected by oxygen due to their luminescence mechanism, and therefore also have an undesirable property that they cannot be basically produced or used in the presence of oxygen.

Here, luminescence mechanisms will be described.

The ground state of all the substances other than oxygen is a singlet (singlet ground state). For example, the ground state of a fluorescent substance used as a fluorescent marker is a singlet. When excited by light, the fluorescent substance reaches a singlet excited state at 100%, and then returns to a ground state at an efficiency of almost 100%. At this time, so-called "fluorescence" is emitted.

However, in the case of an organic EL element excited not by light but by electric field, a luminescent substance reaches a triplet excited state with a probability of 75%, and only 25% singlet excited states can contribute to light emission. Therefore, in the case of a fluorescence emission-type organic EL element, 75% of excitons are basically dissipated as heat, and therefore cannot contribute to light emission at all.

A difference between a singlet and a triplet will be briefly described.

In a ground state, HOMO level contains two electrons of opposite spin. When one of the electrons is excited to LUMO level without changing its spin direction, a singlet excited state is formed. On the other hand, when one of the electrons is excited to LUMO level while its spin direction is reversed, a triplet excited state is formed.

A transition without spin reversal is called allowed transition, and a transition with spin reversal is called forbidden transition.

Therefore, a transition from a ground state to an excited singlet state is an allowed transition, a transition from an excited singlet state to an excited triplet state is a forbidden transition, and a transition from an excited triplet state to a ground state is also a forbidden transition.

In general, an allowed transition is kinetically very fast, and a forbidden transition with spin reversal is very slow.

For example, when quinacridon that is a common fluorescent substance is excited by light to a singlet excited state, a speed at which the singlet excited state is deactivated to a ground state, that is, so-called fluorescence lifetime (Tf) is several picoseconds to several tens of picoseconds. On the other hand, in the case of benzophenone that shows phosphorescence emission under a low-temperature condition in liquid nitrogen, a speed at which benzophenone in a triplet excited state is deactivated to a ground state, that is, so-called phosphorescence lifetime (Tp) is several milliseconds to several tens of milliseconds, which differs by 5 to 6 orders of magnitude.

Benzophenone is a compound made of only carbon, oxygen, and hydrogen. However, a phosphorescence-emitting complex formed by coordinating three ligands to iridium as a heavy metal, such as $Ir(ppy)_3$, has a phosphorescence lifetime of several microseconds due to the effect of the heavy metal. Although phosphorescence involves a forbidden transition, the speed thereof is 1000 times or more higher than usual.

Further, it is known that intersystem crossing from a singlet excited state to a triplet excited state is accelerated due to the heavy atom effect of iridium, and therefore fluorescence of this substance is not observed at all, and only phosphorescence from an triplet excited state is emitted with high efficiency in a phosphorescence quantum yield (hereinafter, also referred to as quantum yield) of almost 100%.

Particularly, an oxygen molecule is usually stable in a triplet state, and therefore acts as a triplet quencher. As shown in FIG. 1, each of the $\pi^*2p$ orbitals of an oxygen molecule is occupied by one electron, which is a state having a total spin quantum number of 1. This state is called triplet oxygen, and the electron configuration thereof is most stable. Therefore, an oxygen molecule is usually present in a triplet state, and is the only molecule whose ground state is a triplet. Due to such a specific property of an oxygen molecule, energy transfer between the triplet state of an iridium complex and the triplet state of an oxygen molecule occurs without electron spin reversal, and therefore the speed of the energy transfer is high, and the presence of triplet oxygen causes poor emission.

Here, energy transfer will be described.

Energy transfer can be described by two main energy transfer mechanisms, Forster mechanism and Dexter mechanism.

Forster mechanism depends on three factors, the distance between two molecules, the overlap between emission and absorption spectra, and the relative orientation of bipolar moment. It is considered that energy transfer between triplet oxygen and an iridium complex occurs mainly via Dexter mechanism because the degree of overlap between emission and absorption spectra is small and therefore energy transfer via Forster mechanism is small.

Energy transfer via Dexter mechanism is a short-range phenomenon that decreases with $e^{-R}$, and depends on the spatial overlap between the molecular orbitals of two molecules. More specifically, the speed of the energy transfer exponentially decreases as the distance between two molecules increases. Therefore, it is important to increase the distance between an iridium complex and triplet oxygen.

However, an oxygen molecule is very small, and therefore enters the central part of an iridium complex so that energy transfer via Dexter mechanism occurs.

In order to solve the problem, we have developed an iridium complex whose iridium atom is completely surrounded by substituent groups and have succeeded in completely keeping oxygen away from the iridium atom.

Here, a phosphorescence-emitting complex will be described. As complexes capable of emitting phosphorescence, an iridium complex and a platinum complex are well known. As described above, phosphorescence emission requires spin reversal. The use of a heavy atom such as Ir or Pt allows phosphorescence emission due to heavy atom effect.

Figure 2:
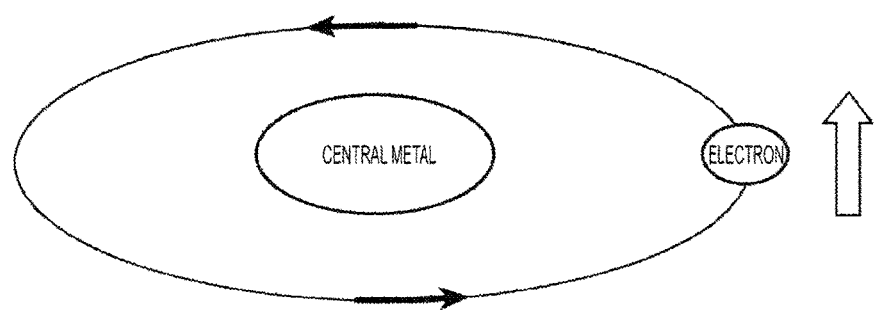
FIG. 2 is a schematic diagram showing the heavy atom effect of a phosphorescence-emitting complex.

This can be described by spin orbit interaction. An electron has a spin and orbits a central nucleus, and at this time, the use of a heavy metal makes it possible to increase centrifugal force and to reverse the spin (see FIG. 2).

Here, the structure of a phosphorescence-emitting complex will be described.

A platinum complex is a planar 4-coordinated complex having a large vacant space around a metal atom, and is therefore not suitable for the present invention.

On the other hand, an iridium complex is an octahedral 6-coordinated complex and therefore has a spherical structure in which a metal atom is surrounded by ligands coordinating to the metal atom. As an iridium complex capable of emitting phosphorescence, $Ir(ppy)_3$ is well known. When the optimized structure of $Ir(ppy)_3$ is calculated by Gaussian and the volume occupied by the complex is approximated by an ellipsoid, the aspect ratio between a longer diameter and a shorter diameter is 1.01. This indicates that an iridium atom in the octahedral 6-coordinated iridium complex is surrounded by ligands in all directions.

Various studies have heretofore been made by taking advantage of the structural feature of an iridium complex having a spherical structure. For example, as described in JP 2003-231692 A and WO 2009/008367, the distance between the molecules of an iridium complex is increased by introducing a large substituent group into the ligands of the iridium complex to increase luminous efficiency.

Further, studies have been made in which a unit having electron transportability (electron transportable unit) is introduced into an iridium complex to promote the injection of electrons into the iridium complex.

These studies are different from the present invention in purposes and effects. Unlike the regular octahedral iridium complex according to the present invention, iridium complexes obtained from the studies are high in the ratio of volume occupied by ligands but are not high in the coverage of the space around the metal, and therefore cannot emit light in the presence of oxygen.

Under the circumstances, we have intensively studied, and as a result, have succeeded in developing an iridium complex shielded from oxygen by optimizing its coefficient of external influence (Svdw) (=Van der Waals surface area/ molecular weight).

The coefficient of external influence of the iridium complex is preferably 0.73 $Å^2$/MW or less from the viewpoint of keeping oxygen away from iridium as a central metal, and is more preferably 0.69 $Å^2$/MW or less.

Here, "coefficient of external influence (Svdw)" refers to an index indicating the degree of possible external influence on the iridium complex. More specifically, "coefficient of external influence" means the Van der Waals (sometimes abbreviated as "VDW") surface area per molecular weight of the iridium complex as represented by the following definition equation:

$$\text{Coefficient of external influence (Svdw)} = \text{Van der Waals surface area } [Å^2]/\text{Molecular weight (MW)}.$$

The smaller value of the coefficient, that is, the smaller value of VDW surface area per certain molecular weight indicates that atoms constituting the iridium complex are present more densely in a space having a small surface area. This means that iridium as a central metal is shielded by atoms constituting ligands so as to be less likely to receive external influence, for example, influence of oxygen.

It is to be noted that in this application, the Van der Waals surface area and the molecular weight are defined as values calculated based on the following certain procedure.

More specifically, structural optimization was performed by molecular orbital calculation software, Gaussian 98 (Gaussian 98, Revision A. 11. 4, M. J. Frisch, et al, Gaussian, Inc., Pittsburgh Pa., 2002.) produced by Gaussian, Inc. in USA using B3LYP/6-31G* as a keyword, and the molecular weight (MW) and Van der Waals surface area of the optimized structure were determined.

Further, the iridium complex according to the present invention had a problem in synthesis, but the problem could be solved by the following method.

Usually, an iridium complex is synthesized using iridium chloride as a starting material, but this reaction proceeds through a dimer intermediate, called p complex, cross-linked by two chlorine atoms to finally produce an iridium complex through a substitution reaction between a chlorine atom and a ligand or a substitution reaction through an acetylacetone complex. However, the iridium complex according to the present invention cannot be produced by the above reaction. This is because the above reaction does not proceed due to the large steric hindrance of the iridium complex according to the present invention during the reaction.

In order to solve the above problem, the reaction needs to be performed at high temperature to exceed a large activation energy resulting from the large steric hindrance during the reaction. However, there is no organic solvent whose solubility and boiling point are suitable for such a high temperature reaction. For this reason, the synthesis of the iridium complex according to the present invention was considered to be difficult.

As a result of intensive studies, it has been found that a solvent-free reaction in which a ligand itself acts as an alternative to an organic solvent is effective for the reason that a high-temperature reaction state can be easily achieved.

However, it is difficult to allow a desired complex-forming reaction to proceed at a temperature equal to or higher than the decomposition temperature of an organic compound serving as a ligand, and therefore the reaction temperature of a complex-forming reaction actually applicable to the present invention is equal to or higher than the melting point of the ligand but equal to or less than the decomposition temperature of the ligand.

The iridium complex according to the present invention can be efficiently synthesized by using the above method in combination with any one of the following methods (1) to (3).

For example, a method (1) is a method in which the complex is closest-packed by introducing a substituent group into the complex after the complex is formed. A method (2) is a method in which the complex is closest-packed by converting a meridional isomer of the complex previously synthesized to a facial isomer of the complex by, for example, a photoisomerization reaction. A method (3) is a method in which the complex is closest-packed by reacting, at high pressure, a bulky ligand that prevents a complex-forming reaction from proceeding under a normal temperature condition and a metal ion source.

The closest packing structure of an iridium complex not only inhibits energy transfer between the iridium complex and triplet oxygen but also has an advantage in improving the characteristics of an organic EL element. Particularly, the closest packing structure of an iridium complex is effective at increasing emission lifetime.

Three possible causes of a reduction in the emission lifetime of an organic EL element are the following:

(I) Decomposition of iridium complex;
(II) Aggregation of molecules of iridium complex; and
(III) Interaction between iridium complex and host compound.

In regard to (I), decomposition of an iridium complex can be suppressed by surrounding its central metal with ligands because even when a nucleophile and an electrophile are present, it is possible to avoid contact of the nucleophile and the electrophile with the chemical bond and the coordination bond between a metal part and a ligand part of the iridium complex.

In regard to (II), the distance between an Ir part in which positive charges are most localized and a ligand part in which negative charges are localized can be increased by surrounding a central metal with ligands. Therefore, electrostatic interaction between the molecules of an iridium complex is reduced so that aggregation can be suppressed.

Figure 3:
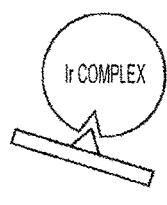
FIG. 3 is a schematic diagram showing interaction between a common Ir complex and a host compound and interaction between an Ir complex according to the present invention and a host compound.
Figure 3:
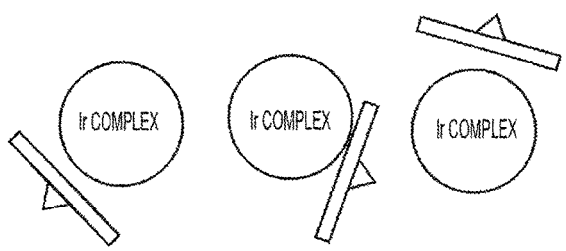

In regard to (III), as shown in FIG. 3, a spherical iridium complex with no gaps has no interaction sites, and therefore the number of interaction points with a host compound is significantly increased. Therefore, various assemblies coexist, which increases entropy and improves stability. That is, the initial state of a light-emitting layer can be stabilized, and therefore a change in the condition of film of the light-emitting layer with time or during application of electric current can be suppressed.

Hereinbelow, the iridium complex according to the present invention will be described from the viewpoint of production.

In the case of a vapor deposition-type organic EL element, a vapor deposition temperature can be reduced because the aggregation of the iridium complex can be suppressed as described above. Decomposition of the complex can be suppressed in a long-time vapor-deposition process, and therefore variations in the performance of organic EL elements can be reduced.

Further, decomposition products are less likely to remain in a vapor deposition source, and therefore the process of adding the complex to a vapor deposition source during production by vapor deposition is simplified, which makes it possible to improve productivity.

On the other hand, a coating-type organic EL element can be produced by coating in the atmosphere.

It is to be noted that the entry of oxygen into an organic EL element deteriorates the performance of the element, and therefore an organic EL element is usually required to be produced at an oxygen permeability of $1 \times 10^{-3}$ mL/m$^2 \cdot$24 h·atm or less (as measured by a method in accordance with JIS K 7129-1992).

However, the use of the iridium complex according to the present invention significantly improved the requirement for oxygen permeability. This makes it possible to achieve coating in the atmosphere and therefore to significantly reduce production cost.

<Constituent Layers of Organic EL Element>

Constituent layers of the organic EL element according to the present invention will be described. Preferred specific examples of the layer configuration of various organic layers sandwiched between an anode and a cathode of the organic EL element according to the present invention are shown below, but the present invention is not limited thereto.

(i) anode/light-emitting layer unit/electron transport layer/cathode (ii) anode/hole transport layer/light-emitting layer unit/electron transport layer/cathode (iii) anode/hole transport layer/light-emitting layer unit/hole blocking layer/electron transport layer/cathode (iv) anode/hole transport layer/light-emitting layer unit/hole blocking layer/electron transport layer/cathode buffer layer/cathode (v) anode/anode buffer layer/hole transport layer/light-emitting layer unit/hole blocking layer/electron transport layer/cathode buffer layer/cathode Further, the light-emitting layer unit may have a non-luminescent interlayer provided between light-emitting layers, and may be configured as a multi-photon unit in which the intermediate layer is a charge generating layer. In this case, examples of the charge generating layer include: a conductive inorganic compound layer such as ITO (indium tin oxide), IZO (indium zinc oxide), $ZnO_2$, TiN, ZrN, HfN, $TiO_x$, $VO_x$, CuI, InN, GaN, $CuAlO_2$, $CuGaO_2$, $SrCu_2O_2$, $LaB_6$, or $RuO_2$; a bilayer film such as $Au/Bi_2O_3$; a multilayer film such as $SnO_2/Ag/SnO_2$, $ZnO/Ag/ZnO$, $Bi_2O_3/Au/Bi_2O_3$, $TiO_2/TiN/TiO_2$, or $TiO_2/ZrN/TiO_2$; fullerenes such as $C_{60}$; a conductive organic layer such as oligothiophene; and a conductive organic compound layer such as metal phthalocyanine, metal-free phthalocyanine, metal porphyrin, or metal-free porphyrin.

The light-emitting layer of the organic EL element according to the present invention is preferably a white light-emitting layer, and a lighting device using them is preferred.

Each of the constituent layers of the organic EL element according to the present invention will be described below.

<Light-Emitting Layer>

The light-emitting layer used in the present invention is a layer that emits light by recombination of electrons and holes injected from the electrodes or from the electron transport layer and the hole transport layer, and a light-emitting portion may be within the light-emitting layer or at the interface between the light-emitting layer and an adjacent layer.

The total thickness of the light-emitting layers is not particularly limited, but is preferably adjusted to be in the range of 2 nm to 5 μm, more preferably in the range of 2 to 200 nm, particularly preferably in the range of 5 to 100 nm from the viewpoint of achieving the homogeneity of films, preventing application of an unnecessarily-high voltage during light emission, and improving the stability of emission color against driving current.

The light-emitting layer can be formed by forming a film using a luminescent dopant and a host compound that will be described layer by, for example, a vacuum deposition method or a wet method (also referred to as wet process, and examples thereof include spin coating, casting, die coating, blade coating, roll coating, ink jetting, printing, spray coating, curtain coating, and LB (Langmuir Blodgett) process).

The light-emitting layer of the organic EL element according to the present invention preferably contains a luminescent dopant (phosphorescence-emitting dopant or fluorescence-emitting dopant) compound and a host compound.

(1) Luminescent Dopant Compound

The luminescent dopant compound (also referred to as luminescent dopant or dopant compound or simply as dopant) will be described.

As the luminescent dopant, a fluorescence-emitting dopant (also referred to as fluorescent dopant, fluorescent compound, or fluorescence-emitting compound) or a phosphorescence-emitting dopant (also referred to as phosphorescent dopant, phosphorescent compound, or phosphorescence-emitting compound) can be used.

(1.1) Phosphorescent Dopant

The phosphorescent dopant will be described.

The phosphorescent dopant is a compound in which light emission from an excited triplet is observed, more specifically a compound that emits phosphorescence at room temperature (25° C.), and is defined as a compound having a phosphorescence quantum yield of 0.01 or more at 25° C. The phosphorescence quantum yield is preferably 0.1 or more.

The phosphorescence quantum yield can be measured by a method described in The Fourth Series of Experimental Chemistry, Vol. 7 Spectroscopy II, p. 398 (1992, Maruzen Publishing Co., Ltd.). The phosphorescence quantum yield in a solution can be measured using various solvents. However, the phosphorescent dopant used in the present invention shall achieve the above phosphorescence quantum yield (0.01 or more) in any one of arbitrary solvents.

There are two principles for light emission from the phosphorescent dopant. One of them is an energy transfer type in which recombination of carriers occurs on a host compound to which carriers are transported so that an excited state of the luminescent host compound is formed, and this energy is transferred to the phosphorescent dopant so that luminescence is obtained from the phosphorescent dopant. The other is a carrier trap type in which recombination of carriers occurs on the phosphorescent dopant serving as a carrier trap so that luminescence is obtained from the phosphorescent dopant. In either case, the energy of excited state of the phosphorescent dopant is required to be lower than that of excited state of the host compound.

As described above, the present inventors have intensively studied to achieve the above object of the present invention, and as a result, have found that the luminous efficiency and emission lifetime of an organic EL element can be improved by allowing an organic layer of the organic EL element to contain an iridium complex having a coefficient of external influence of 0.73 Å$^2$/MW or less as defined by the above definition equation.

The reason for this is considered to be that when the coefficient of external influence is 0.73 Å$^2$/MW or less, preferably 0.69 Å$^2$/MW or less, oxygen is prevented from coming close to iridium as a central metal, thus resulting in an improvement in luminous efficiency and emission lifetime.

[Iridium Complex Represented by General Formula (1)]

The iridium complex according to the present invention preferably has a partial structure represented by the following general formula (1).

[Chemical Formula 6]

General Formula (1)

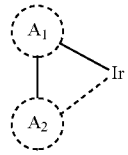

In the general formula (1), $A_1$ is an aromatic ring, and $A_2$ is a nitrogen atom-containing aromatic ring.

In the general formula (1), the aromatic rings represented by $A_1$ and $A_2$ are preferably a 5-membered aromatic ring or a 6-membered aromatic ring. (2) to (5)]

[Iridium Complexes Represented by General Formulas

In the iridium complex according to the present invention, the partial structure represented by the general formula (1) is preferably a partial structure represented by any one of the following general formulas (2) to (5).

[Chemical Formula 7]

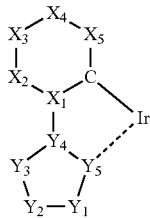

General Formula (2)

In the general formula (2), a carbon atom and $X_1$ to $X_5$ are a group of atoms forming a 6-membered aromatic ring, and $Y_1$ to $Y_5$ are a group of atoms forming a nitrogen atom-containing 5-membered aromatic ring.

[Chemical Formula 8]

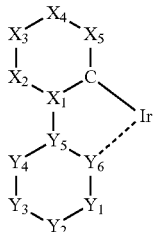

General Formula (3)

In the general formula (3), a carbon atom and $X_1$ to $X_5$ are a group of atoms forming a 6-membered aromatic ring, and $Y_1$ to $Y_6$ are a group of atoms forming a nitrogen atom-containing 6-membered aromatic ring.

[Chemical Formula 9]

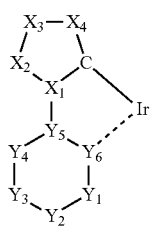

General Formula (4)

In the general formula (4), a carbon atom and $X_1$ to $X_4$ are a group of atoms forming a 5-membered aromatic ring, and $Y_1$ to $Y_6$ are a group of atoms forming a nitrogen atom-containing 6-membered aromatic ring.

[Chemical Formula 10]

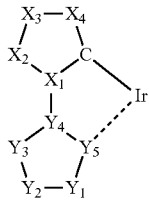

General Formula (5)

In the general formula (5), a carbon atom and $X_1$ to $X_4$ are a group of atoms forming a 5-membered aromatic ring, and $Y_1$ to $Y_5$ are a group of atoms forming a nitrogen atom-containing 5-membered aromatic ring.

Further, it is preferred that in the above general formula (2) or (3), the group of atoms consisting of a carbon atom and $X_1$ to $X_5$ forms a benzene ring or a pyridine ring.

Further, it is preferred that in the above general formula (2) or (5), the nitrogen-containing group of atoms consisting of $Y_1$ to $Y_5$ forms an imidazole ring, a pyrazole ring, or a triazole ring.

Further, it is preferred that in the above general formula (2) or (3), at least one of the atoms represented by $X_5$ and $Y_1$ is a carbon atom having a substituent group, and the substituent group is a halogen atom, a trifluoromethyl group, or a pentafluorophenyl group.

Further, it is preferred that in the above general formula (4) or (5), at least one of the atoms represented by $X_4$ and $Y_1$ is a carbon atom having a substituent group, and the substituent group is a halogen atom, a trifluoromethyl group, or a pentafluorophenyl group.

The aromatic ring contained in the partial structure represented by each of the general formulas (1) to (5) may further have a substituent group, and the substituent group may be linked to another group to form a fused ring. Examples of the substituent group include: an alkyl group (e.g., methyl, ethyl, trifluoromethyl, isopropyl); an alkoxy group (e.g., methoxy, ethoxy); a halogen atom (e.g., fluorine atom); a nitro group; a dialkylamino group (e.g., dimethylamino); a trialkylsilyl group (e.g., trimethylsilyl); a triarylsilyl group (e.g., triphenylsilyl); a triheteroarylsilyl group (e.g., tripyridylsilyl); a benzyl group; an aryl group (e.g., phenyl); and a heteroaryl group (e.g., pyridyl, carbazolyl).

[Specific Examples of Iridium Complex]

Hereinbelow, specific examples of the iridium complex according to the present invention represented by any one of the general formulas (1) to (5) are shown below, but the present invention is not limited thereto.

[Chemical Formula 11]

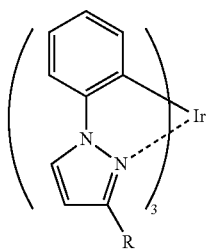

(A)

-continued
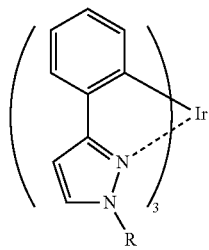
(B)
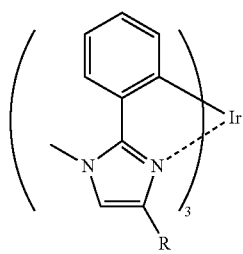
(C)
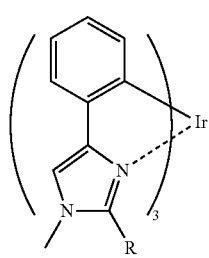
(D)
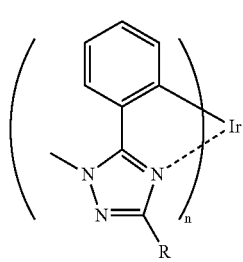
(E)
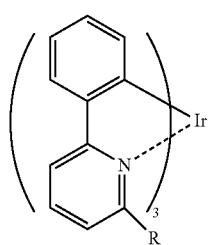
(F)
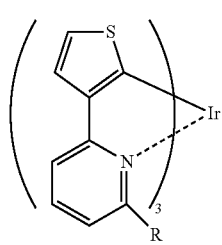
(G)
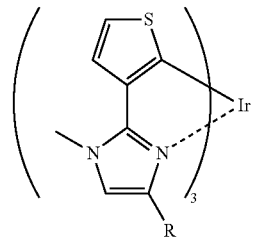
(H)
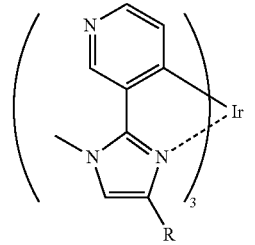
(I)
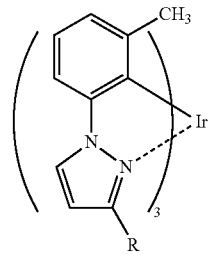
(J)
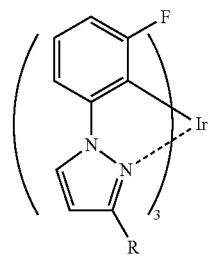
(K)
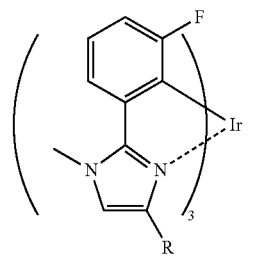
(L)
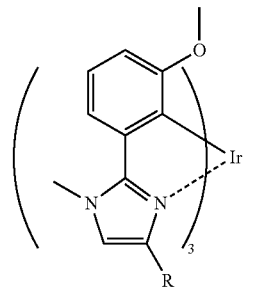
(M)

-continued
(N)
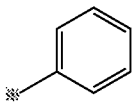
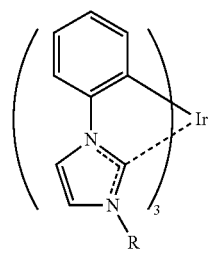
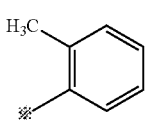
(O)
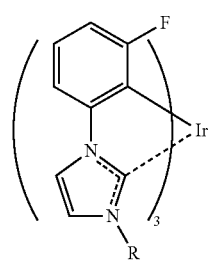
* —Br
* —F
* —Cl
(P)
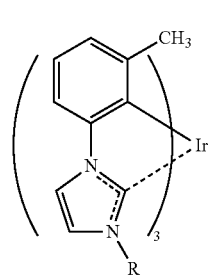
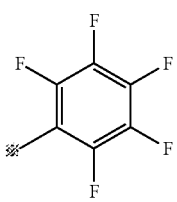
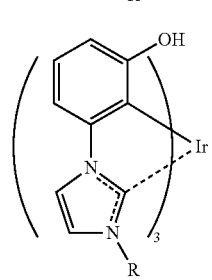
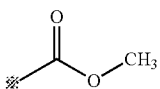
(Q)
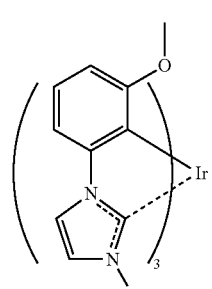
* —S—
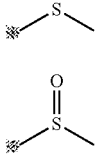
[Chemical Formula 12]
(R)
R1
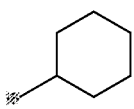
R2
R3
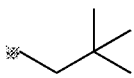
R4
R5
R6
R7
R8
R9
R10
R11
R12
R13
R14
R15
R16
R17
R18
R19
R20

-continued

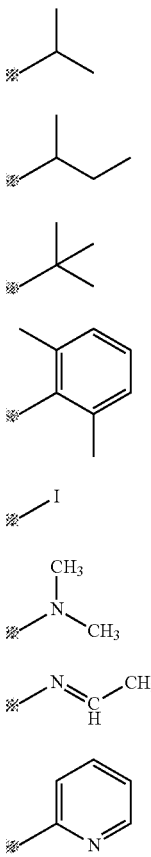

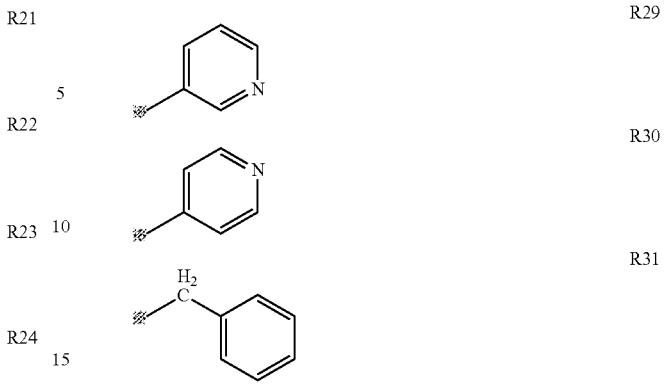

It is to be noted that a substituent group R contained in structural formulas (A) to (R) is a substituent group represented by any one of R1 to R4 and R6 to R31 wherein ⋇ represents a substitution position.

[Coefficient of External Influence of Iridium Complex]

Structural optimization was performed on the iridium complex according to the present invention by molecular orbital computational software, Gaussian 98 (Gaussian 98, Revision A. 11. 4, M. J. Frisch, et al, Gaussian, Inc., Pittsburgh Pa., 2002.) produced by Gaussian, Inc. (USA) using B3LYP/6-31G* as a keyword, and the molecular weight (MW) and Van der Waals surface area of the structurally-optimized iridium complex were determined. From the thus obtained molecular weight and Van der Waals surface area, the coefficient of external influence (Svdw) (=Van der Waals surface area [$Å^2$]/molecular weight (MW)) can be determined. The coefficients of external influence of iridium complexes calculated based on the definition equation are shown in Tables 1 to 4.

TABLE 1

| Dopant Compound | Van der Waals Surface Area [$Å^2$] | Molecular Weight [MW] | Coefficient of External Influence [$Å^2$/MW] | Note |
| --- | --- | --- | --- | --- |
| (A)-R1 | 460.53 | 621.71 | 0.74 | Comparative Example |
| (A)-R2 | 506.71 | 663.79 | 0.76 | Comparative Example |
| (A)-R3 | 545.54 | 825.71 | 0.66 | Present Invention |
| (A)-R4 | 506.09 | 756.71 | 0.67 | Present Invention |
| (A)-R6 | 648.86 | 850.00 | 0.76 | Comparative Example |
| (A)-R7 | 702.43 | 892.08 | 0.79 | Comparative Example |
| (A)-R8 | 514.01 | 858.40 | 0.60 | Present Invention |
| (A)-R9 | 480.87 | 675.68 | 0.71 | Present Invention |
| (A)-R10 | 506.70 | 725.05 | 0.70 | Present Invention |
| (A)-R11 | 783.12 | 1119.86 | 0.70 | Present Invention |
| (A)-R12 | 589.23 | 795.81 | 0.74 | Comparative Example |
| (A)-R13 | 670.89 | 882.94 | 0.76 | Comparative Example |
| (A)-R14 | 559.63 | 759.98 | 0.74 | Comparative Example |
| (A)-R25 | 524.84 | 999.39 | 0.53 | Present Invention |
| (A)-R26 | 504.87 | 666.75 | 0.76 | Comparative Example |
| (A)-R27 | 617.61 | 744.87 | 0.83 | Comparative Example |
| (A)-R31 | 756.18 | 886.03 | 0.85 | Comparative Example |
| (B)-R1 | 461.94 | 621.71 | 0.74 | Comparative Example |
| (B)-R2 | 518.59 | 663.79 | 0.78 | Comparative Example |
| (B)-R3 | 549.87 | 825.71 | 0.67 | Present Invention |

TABLE 1-continued

| Dopant Compound | Van der Waals Surface Area [Å²] | Molecular Weight [MW] | Coefficient of External Influence [Å²/MW] | Note |
|---|---|---|---|---|
| (B)-R4 | 540.51 | 756.71 | 0.71 | Present Invention |
| (B)-R6 | 640.99 | 850.00 | 0.75 | Comparative Example |
| (B)-R7 | 708.00 | 892.08 | 0.79 | Comparative Example |
| (B)-R11 | 767.03 | 1119.86 | 0.68 | Present Invention |
| (B)-R12 | 588.49 | 795.81 | 0.74 | Comparative Example |
| (B)-R13 | 670.32 | 882.94 | 0.76 | Comparative Example |
| (B)-R14 | 562.26 | 759.98 | 0.74 | Comparative Example |
| (B)-R21 | 602.24 | 747.95 | 0.81 | Comparative Example |
| (B)-R28 | 645.83 | 852.96 | 0.76 | Comparative Example |

TABLE 2

| Dopant Compound | Van der Waals Surface Area [Å²] | Molecular Weight [MW] | Coefficient of External Influence [Å²/MW] | Note |
|---|---|---|---|---|
| (C)-R1 | 518.59 | 663.79 | 0.78 | Comparative Example |
| (C)-R2 | 569.25 | 705.87 | 0.81 | Comparative Example |
| (C)-R3 | 624.31 | 867.79 | 0.72 | Present Invention |
| (C)-R4 | 574.67 | 798.79 | 0.72 | Present Invention |
| (C)-R6 | 713.66 | 892.08 | 0.80 | Comparative Example |
| (C)-R7 | 735.56 | 934.16 | 0.79 | Comparative Example |
| (C)-R8 | 566.34 | 900.48 | 0.63 | Present Invention |
| (C)-R9 | 539.67 | 717.76 | 0.75 | Comparative Example |
| (C)-R10 | 555.89 | 767.13 | 0.72 | Present Invention |
| (C)-R11 | 790.44 | 1161.94 | 0.68 | Present Invention |
| (D)-R1 | 526.82 | 663.79 | 0.79 | Comparative Example |
| (D)-R2 | 560.21 | 705.87 | 0.79 | Comparative Example |
| (D)-R3 | 582.41 | 867.79 | 0.67 | Present Invention |
| (D)-R4 | 596.11 | 798.79 | 0.75 | Comparative Example |
| (D)-R6 | 702.43 | 892.08 | 0.79 | Comparative Example |
| (D)-R7 | 759.48 | 934.16 | 0.81 | Comparative Example |
| (D)-R8 | 577.23 | 900.48 | 0.64 | Present Invention |
| (D)-R9 | 547.91 | 717.76 | 0.76 | Comparative Example |
| (D)-R10 | 572.49 | 767.13 | 0.75 | Comparative Example |
| (D)-R11 | 801.34 | 1161.94 | 0.69 | Present Invention |
| (E)-R1 | 497.61 | 666.79 | 0.75 | Comparative Example |
| (E)-R2 | 545.28 | 708.87 | 0.77 | Comparative Example |
| (E)-R3 | 608.94 | 870.79 | 0.70 | Present Invention |
| (E)-R4 | 568.65 | 801.79 | 0.71 | Present Invention |
| (E)-R6 | 699.28 | 895.08 | 0.78 | Comparative Example |
| (E)-R7 | 749.73 | 937.16 | 0.80 | Comparative Example |
| (E)-R9 | 514.83 | 720.76 | 0.71 | Present Invention |
| (E)-R10 | 542.35 | 770.13 | 0.70 | Present Invention |
| (E)-R11 | 714.69 | 1164.94 | 0.61 | Present Invention |

TABLE 3

| Dopant Compound | Van der Waals Surface Area [Å²] | Molecular Weight [MW] | Coefficient of External Influence [Å²/MW] | Note |
| --- | --- | --- | --- | --- |
| (F)-R1 | 499.83 | 654.78 | 0.76 | Comparative Example |
| (F)-R2 | 527.92 | 696.86 | 0.76 | Comparative Example |
| (F)-R3 | 517.06 | 858.77 | 0.60 | Present Invention |
| (F)-R4 | 502.63 | 789.77 | 0.64 | Present Invention |
| (F)-R8 | 496.23 | 891.47 | 0.56 | Present Invention |
| (F)-R9 | 497.63 | 708.75 | 0.70 | Present Invention |
| (F)-R10 | 497.01 | 758.12 | 0.66 | Present Invention |
| (F)-R12 | 584.75 | 828.88 | 0.71 | Present Invention |
| (F)-R14 | 567.80 | 793.05 | 0.72 | Present Invention |
| (F)-R15 | 574.36 | 793.05 | 0.72 | Present Invention |
| (F)-R21 | 558.08 | 781.02 | 0.71 | Present Invention |
| (F)-R25 | 496.72 | 1032.46 | 0.48 | Present Invention |
| (F)-R26 | 564.03 | 783.98 | 0.72 | Present Invention |
| (G)-R3 | 482.43 | 876.84 | 0.55 | Present Invention |
| (G)-R4 | 468.12 | 807.84 | 0.58 | Present Invention |
| (G)-R8 | 461.57 | 909.54 | 0.51 | Present Invention |
| (G)-R9 | 463.00 | 726.82 | 0.64 | Present Invention |
| (G)-R10 | 462.44 | 776.19 | 0.60 | Present Invention |
| (G)-R12 | 550.14 | 846.96 | 0.65 | Present Invention |
| (G)-R14 | 533.18 | 811.13 | 0.66 | Present Invention |
| (G)-R15 | 525.99 | 859.12 | 0.61 | Present Invention |
| (G)-R21 | 530.51 | 799.10 | 0.66 | Present Invention |
| (G)-R25 | 462.07 | 1050.54 | 0.44 | Present Invention |
| (G)-R26 | 495.49 | 802.06 | 0.62 | Present Invention |

TABLE 4

| Dopant Compound | Van der Waals Surface Area [Å²] | Molecular Weight MW | Coefficient of External Influence [Å²/MW] | Note |
| --- | --- | --- | --- | --- |
| (H)-R3 | 566.08 | 885.86 | 0.64 | Present Invention |
| (H)-R4 | 530.36 | 816.86 | 0.65 | Present Invention |
| (H)-R8 | 537.72 | 918.55 | 0.56 | Present Invention |
| (H)-R9 | 505.28 | 735.84 | 0.69 | Present Invention |
| (H)-R10 | 531.01 | 785.20 | 0.68 | Present Invention |
| (H)-R12 | 613.15 | 855.97 | 0.72 | Present Invention |
| (H)-R13 | 694.87 | 943.10 | 0.74 | Comparative Example |
| (H)-R14 | 584.10 | 820.14 | 0.71 | Present Invention |
| (H)-R15 | 574.61 | 868.14 | 0.66 | Present Invention |
| (H)-R21 | 625.10 | 808.11 | 0.77 | Comparative Example |
| (H)-R25 | 548.31 | 1059.55 | 0.52 | Present Invention |
| (H)-R26 | 527.74 | 726.91 | 0.73 | Present Invention |
| (H)-R27 | 641.99 | 805.02 | 0.80 | Comparative Example |
| (H)-R28 | 672.65 | 913.12 | 0.74 | Comparative Example |
| (H)-R31 | 780.37 | 946.19 | 0.82 | Comparative Example |
| (I)-R3 | 573.39 | 870.74 | 0.66 | Present Invention |
| (I)-R8 | 549.99 | 903.44 | 0.61 | Present Invention |
| (I)-R9 | 527.81 | 720.72 | 0.73 | Present Invention |
| (I)-R10 | 544.15 | 770.09 | 0.71 | Present Invention |
| (I)-R21 | 637.28 | 792.99 | 0.80 | Comparative Example |
| (I)-R25 | 557.39 | 1044.44 | 0.53 | Present Invention |
| (J)-R2 | 521.32 | 705.87 | 0.74 | Comparative Example |
| (J)-R3 | 533.97 | 867.78 | 0.62 | Present Invention |
| (K)-R9 | 491.26 | 729.65 | 0.67 | Present Invention |
| (L)-R7 | 706.20 | 988.13 | 0.71 | Present Invention |
| (M)-R3 | 664.86 | 957.86 | 0.69 | Present Invention |
| (N)-R2 | 521.32 | 663.79 | 0.79 | Comparative Example |
| (N)-R3 | 566.62 | 825.70 | 0.69 | Present Invention |
| (O)-R2 | 526.85 | 717.76 | 0.73 | Present Invention |
| (O)-R3 | 572.11 | 879.67 | 0.65 | Present Invention |
| (O)-R6 | 705.18 | 903.97 | 0.78 | Comparative Example |
| (P)-R2 | 578.08 | 867.78 | 0.67 | Present Invention |

TABLE 4-continued

| Dopant Compound | Van der Waals Surface Area [Å$^2$] | Molecular Weight MW | Coefficient of External Influence [Å$^2$/MW] | Note |
|---|---|---|---|---|
| (Q)-R2 | 569.05 | 873.69 | 0.65 | Present Invention |
| (R)-R2 | 597.32 | 753.87 | 0.79 | Comparative Example |

In addition to the above exemplified compounds, the coefficients of external influence of iridium complexes having the partial structure represented by any one of the general formulas (2) to (5) are calculated based on the following hypothesis.

As shown in the following general formulas (2) to (5), a substituent group introduced in a position indicated by an arrow is not located in the vicinity of Ir as a central metal, and therefore can be regarded as not being involved in calculation of the coefficient of external influence. Therefore, a value calculated by regarding $X_1$ to $X_4$ (or $X_5$) and $Y_1$ to $Y_4$ (or $Y_5$) contained in the general formulas (2) to (5) as C—H or N—CH$_3$ can be regarded as the coefficient of external influence at the time when the partial structure has a substituent group in a position indicated by an arrow.

[Chemical Formula 13]

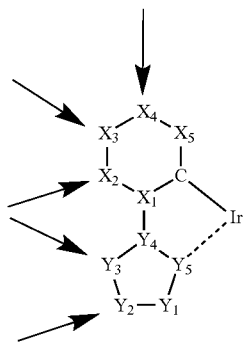

General Formula (2)

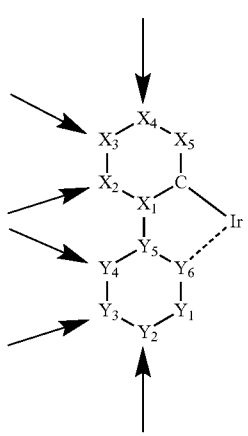

General Formula (3)

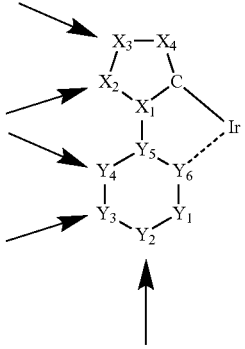

General Formula (4)

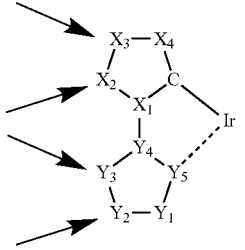

General Formula (5)

More specifically, for example, (A)-R3 having the partial structure represented by the general formula (2) has a coefficient of external influence of 0.66 as calculated based on the above definition equation. Therefore, the following (A)-R3-2 to (A)-R3-5 having a substituent group introduced in any one of positions indicated by arrows in (A)-R3 can also be regarded as having a coefficient of external influence of 0.66.

[Chemical Formula 14]

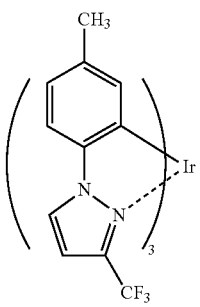

(A)-R3-2

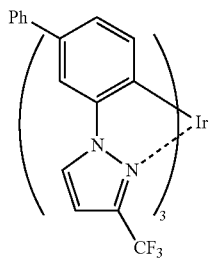
(A)-R3-3

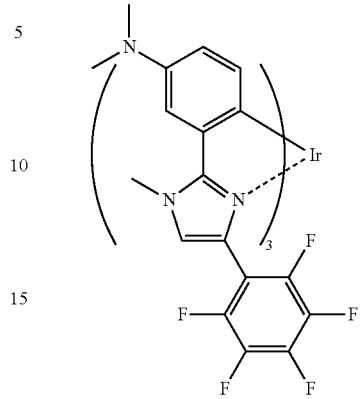
(C)-R11-2

[Chemical Formula 15]

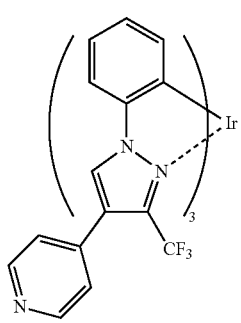
(A)-R3-4

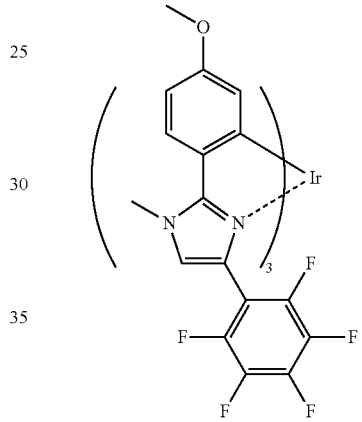
(C)-R11-3

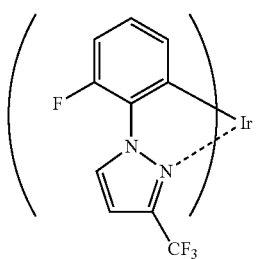
(A)-R3-5

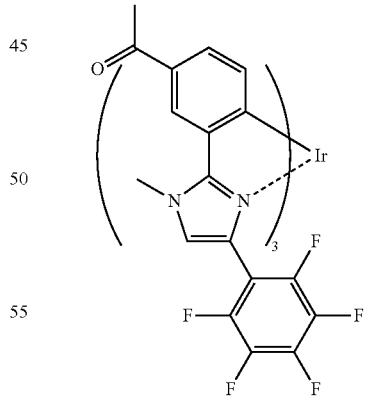
(C)-R11-4

Further, (C)—R11 having the partial structure represented by the general formula (2) has a coefficient of external influence of 0.68 as calculated based on the above definition equation. Therefore, the following (C)—R11-2 to (C)—R11-4 having a substituent group introduced in any one of positions indicated by arrows in (C)—R11 can also be regarded as having a coefficient of external influence of 0.68.

It is to be noted that as in the case of (C)—R11, when anyone of atoms in positions indicated by arrows (in this case, $Y_3$ in the general formula (2)) is substituted with a substituent group containing a nitrogen element, the coefficient of external influence can be calculated by regarding the substituent group as N—$CH_3$.

Further, (F)—R9 having the partial structure represented by the general formula (3) has a coefficient of external influence of 0.70 as calculated based on the above definition equation. Therefore, the following (F)—R9-2 to (F)—R9-5 having a substituent group introduced in any one of positions indicated by arrows in (F)—R9 can also be regarded as having a coefficient of external influence of 0.70.

[Chemical Formula 16]

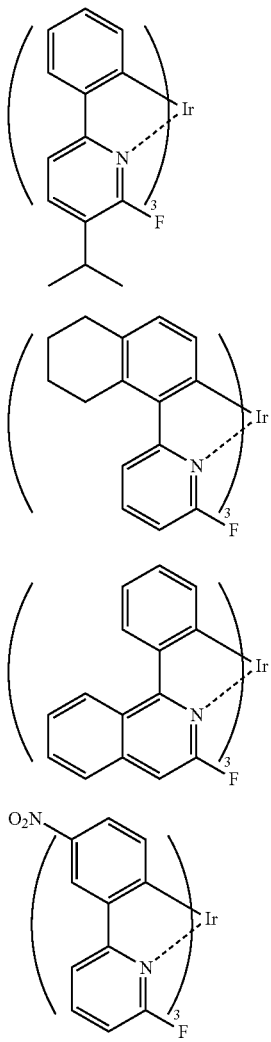

(F)-R9-2

(F)-R9-3

(F)-R9-4

(F)-R9-5

Further, (G)-R14 having the partial structure represented by the general formula (4) has a coefficient of external influence of 0.66 as calculated based on the above definition equation. Therefore, the following (G)-R14-2 to (G)-R14-4 having a substituent group introduced in any one of positions indicated by arrows in (G)-R14 can also be regarded as having a coefficient of external influence of 0.66.

[Chemical Formula 17]

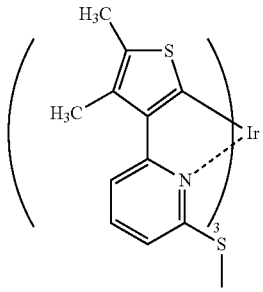

(G)-R14-2

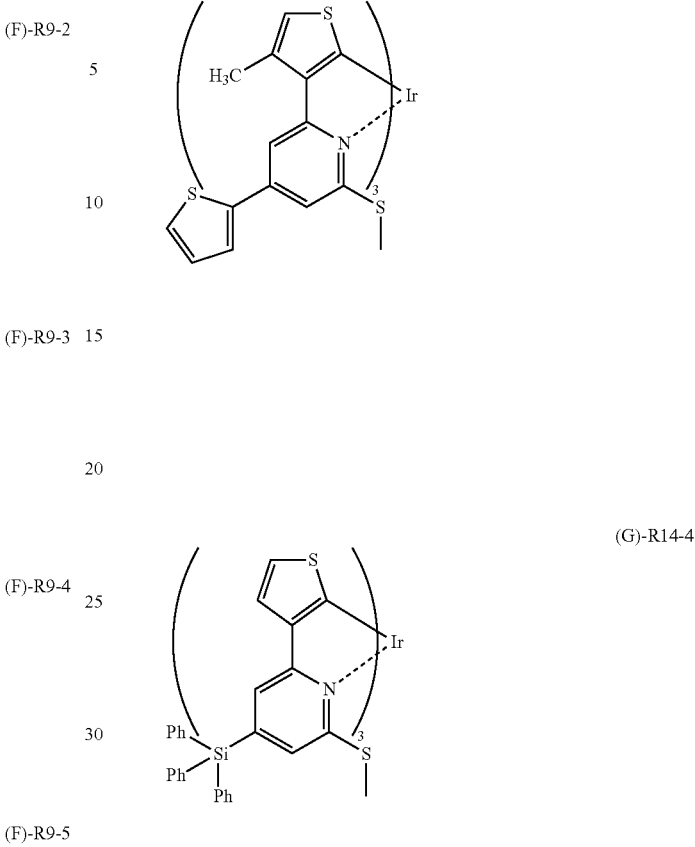

(G)-R14-3

(G)-R14-4

It is to be noted that a bulky substituent group such as a triphenylsilyl group introduced into (G)-R14-4 is considered to have an influence on steric structure and coordination environment, but does not significantly change the coefficient of external influence. Therefore, the coefficient of external influence of (G)-R14-4 can be regarded to be equal to that of (G)-R14.

Further, the coefficient of external influence of the iridium complex having a substituent group introduced in any one of positions indicated by arrows in the partial structure represented by the general formula (5) can also be calculated based on the same hypothesis.

As described above, the coefficient of external influence of the iridium complex having the partial structure represented by any one of the general formulas (2) to (5) can be regarded as the coefficient of external influence calculated by regarding $X_1$ to $X_4$ (or $X_5$) and $Y_1$ to $Y_4$ (or $Y_5$) contained in any one of the general formulas (2) to (5) as C—H or N—CH$_3$.

[Synthesis Examples of Iridium Complex]

Hereinbelow, synthesis examples of the iridium complex represented by any one of the general formulas (1) to (5) will be described, but the present invention is not limited thereto. Methods for synthesizing the iridium complex will be described below with reference to (A)-R3 and (C)—R11 described above as specific examples of the iridium complex.

[Production Method 1]

(A)-R3 can be synthesized in accordance with the following scheme.

Synthesis of (A)-R3

[Chemical Formula 18]

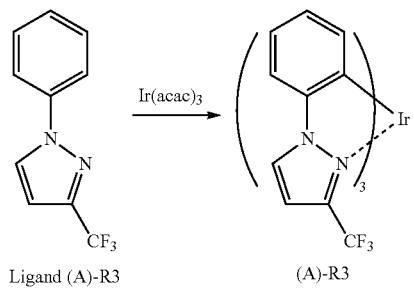

Ligand (A)-R3       (A)-R3

In a sealable glass tube, 0.33 g of Ir(acac)$_3$ and 1.0 g of Ligand (A)-R3 were placed. Then, the tube was purged with nitrogen and sealed using a gas burner to close a system. The glass container was heated to 300° C. using a mantle heater, and a reaction was performed at this temperature for 8 hours.

After the completion of the reaction, deposited crystals were collected by filtration and washed with MeOH. Further, the crystals were purified by silica gel column chromatography (developing solvent: hexane/THF=9/1). As a result, 0.3 g of (A)-R3 was obtained.

It is to be noted that this experiment was performed after a preliminary experiment in which it was confirmed that (A)-R3 was not generated at a reaction temperature of 280° C.

Mass=826

$^1$H-NMR (solvent THF) 8.52 (d) 1H, 7.46 (d) 1H, 6.89-6.87 (t) 1H, 6.79 (d) 1H, 6.61-6.57 (t) 1H, 6.42-6.41 (t) 1H.

As described above, the iridium complex according to the present invention is preferably synthesized by a solvent-free reaction using, as an alternative to a reaction solvent, an organic compound serving as a ligand of the iridium complex.

[Production Method 2]

(C)—R11 can be synthesized in accordance with the following scheme.

Synthesis of (C)-R11

[Chemical Formula 19]

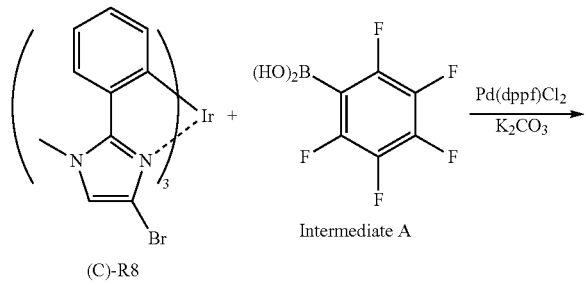

(C)-R8         Intermediate A

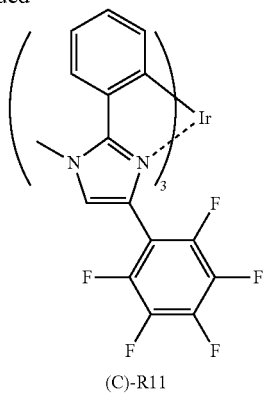

(C)-R11

Under a nitrogen stream, 1.0 g of (C)—R8, 0.85 g of an intermediate A, 0.1 g of Pd(dppf)Cl$_2$, and 0.8 g of K$_2$CO$_3$ were placed in a three-neck flask and dissolved in 40 mL of dimethylsulfoxide (DMSO) to obtain a solution. This solution was heated to 100° C. to reflux for 8 hours.

The reaction mixture was cooled to room temperature, and then water was added thereto. A crude product was obtained from the reaction mixture by extraction with ethyl acetate and vacuum-concentrated.

The crude product was purified by silica gel column chromatography (developing solvent: hexane/THF=9/1). As a result, 0.2 g of (C)—R11 was obtained. The structure of (C)—R11 was determined by nuclear magnetic resonance spectroscopy and mass spectroscopy.

As described above, the iridium complex according to the present invention is preferably produced by coordinating ligands to iridium to form a 6-coordinated iridium complex and then by introducing a substituent group into the ligands of the iridium complex.

The iridium complex according to the present invention can be produced in the same manner as the production method 1 or the production method 2.

(1.2) Fluorescent Dopant

Examples of the fluorescent dopant include coumarin-based dyes, pyran-based dyes, cyanine-based dyes, chloconium-based dyes, squarylium-based dyes, oxobenzanthracene-based dyes, fluorescein-based dyes, rhodamine-based dyes, pyrylium-based dyes, perylene-based dyes, stilbene-based dyes, polythiophene-based dyes, rare-earth complex-based fluorescence emitters, and compounds with high fluorescence quantum yield typified by laser dyes.

[Combined Use with Conventionally-Known Dopant]

The luminescent dopant used in the present invention may be a combination of two or more compounds. For example, phosphorescent dopants different in structure may be used in combination, or a phosphorescent dopant and a fluorescent dopant may be used in combination.

Here, specific examples of a conventionally-known luminescent dopant that may be used as a luminescent dopant in combination with the iridium complex according to the present invention represented by any one of the above general formulas (1) to (5) will be given below, but the present invention is not limited thereto.

[Chemical Formula 20]
D-1 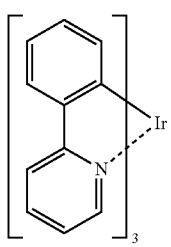
D-2 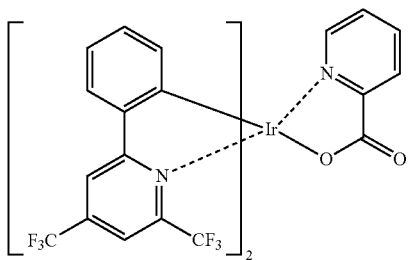
D-3 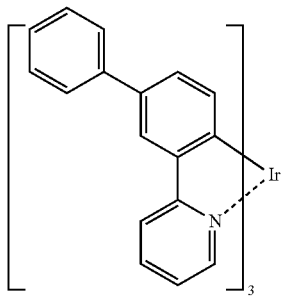
D-4 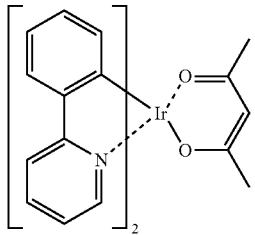
D-5 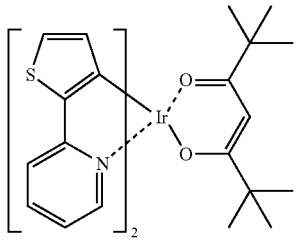
D-6 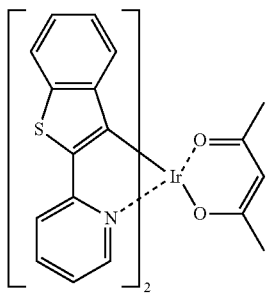
D-7 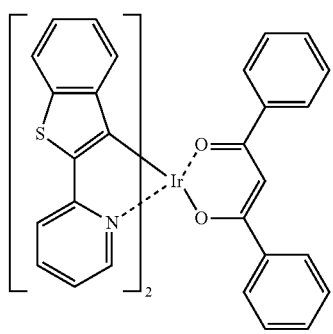
D-8 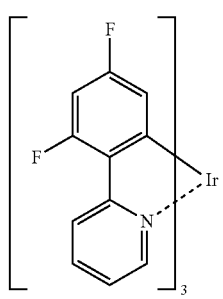
D-9 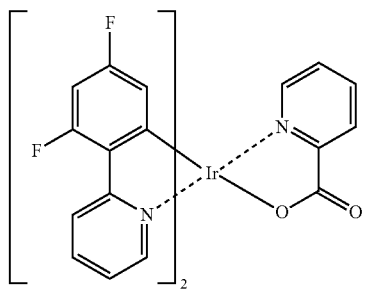
D-10 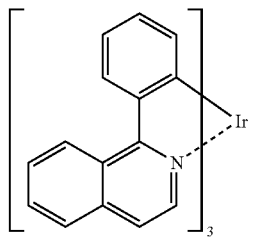
D-11 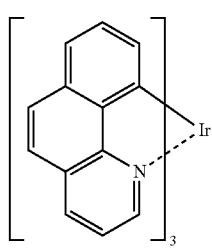

D-12
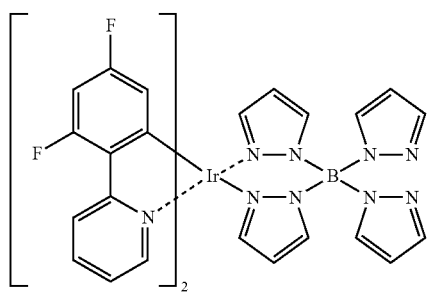
[Chemical Formula 21]
D-13
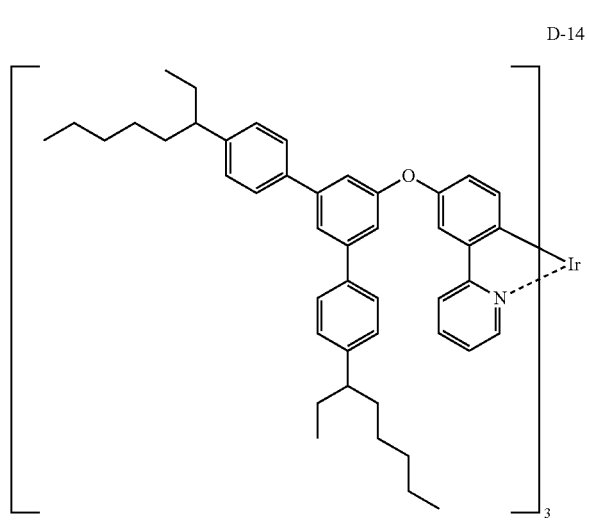
D-14
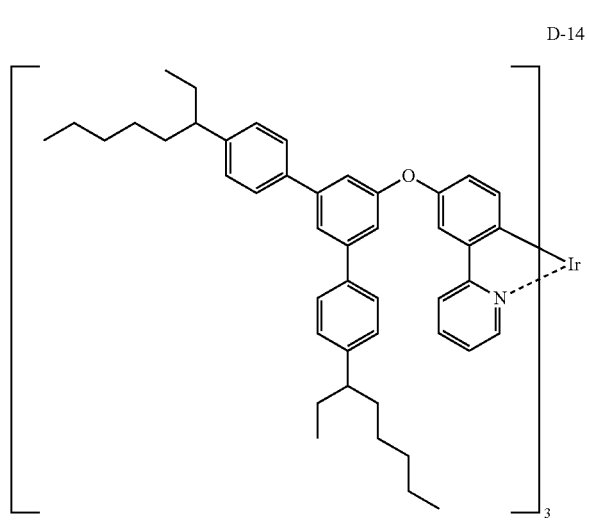
D-15
[Chemical Formula 22]
D-16
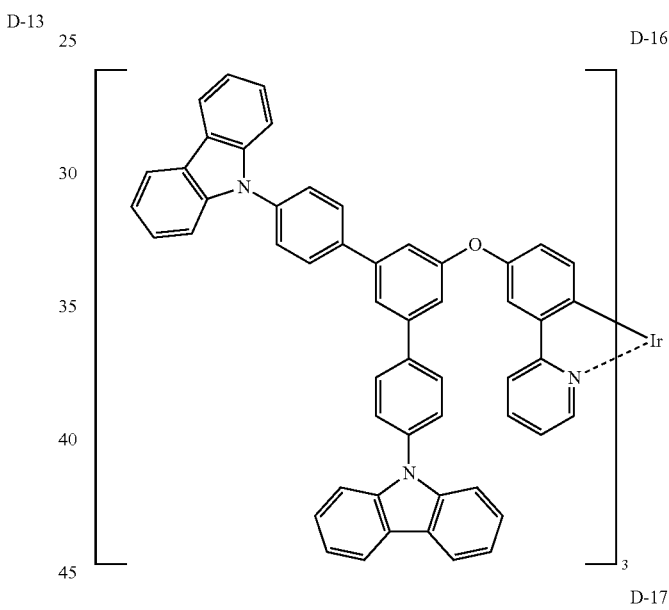
D-17
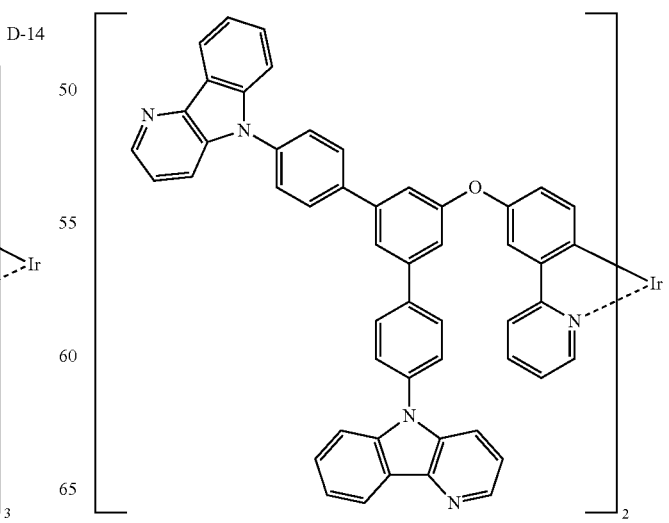

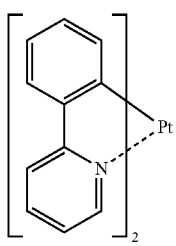
D-18
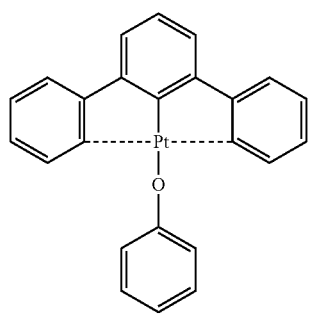
D-19
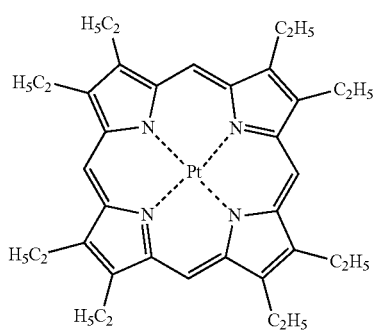
D-20
[Chemical Formula 23]
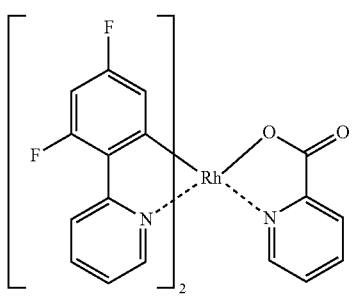
D-21
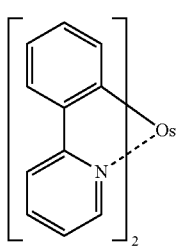
D-22
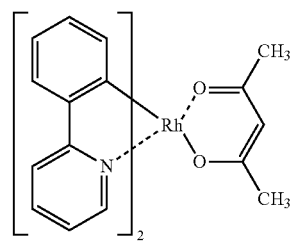
D-23
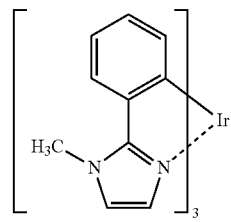
D-24
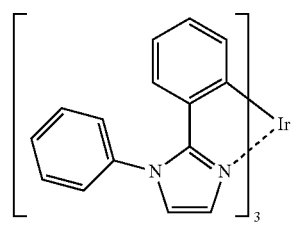
D-25
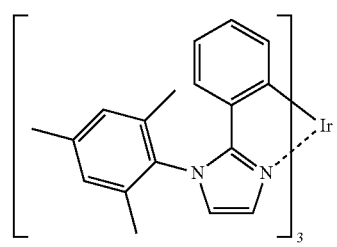
D-26
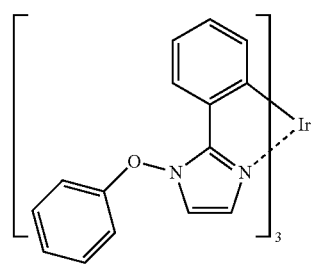
D-27
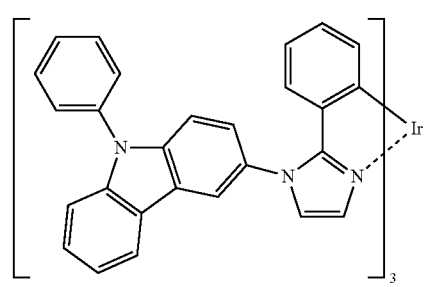
D-28

-continued
D-29
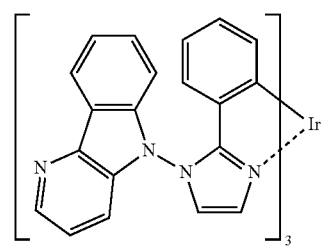
D-30
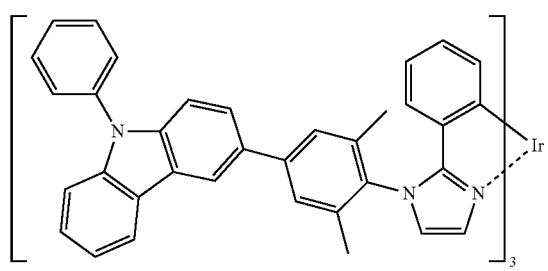
D-31
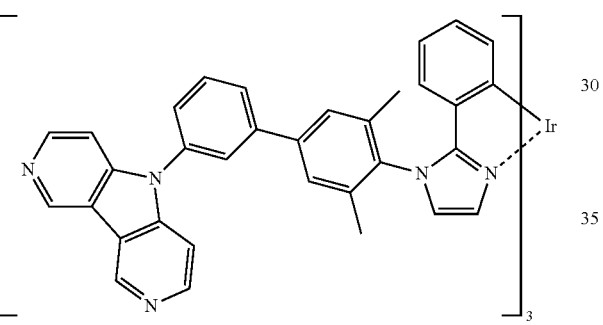
[Chemical Formula 24]
D-32
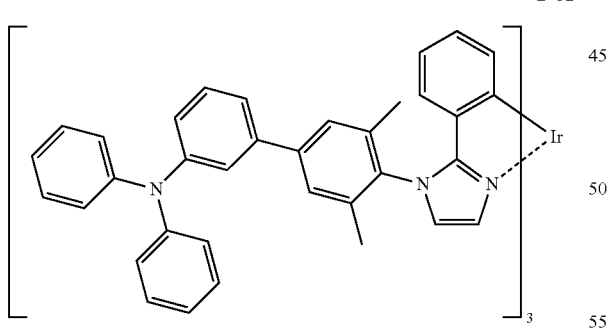
D-33
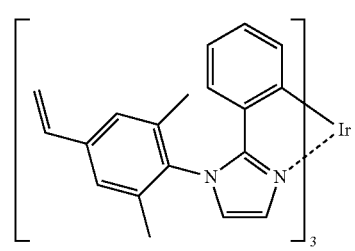
-continued
D-34
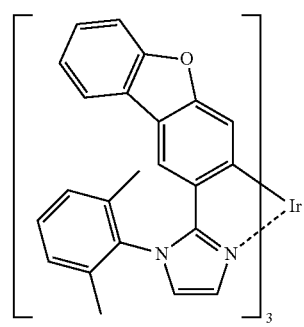
D-35
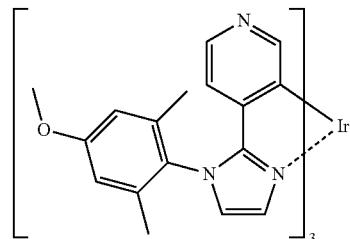
D-36
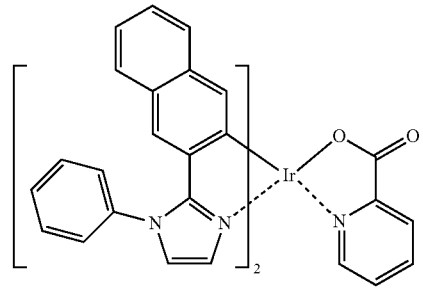
D-37
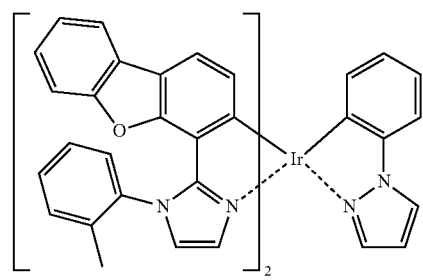
D-38
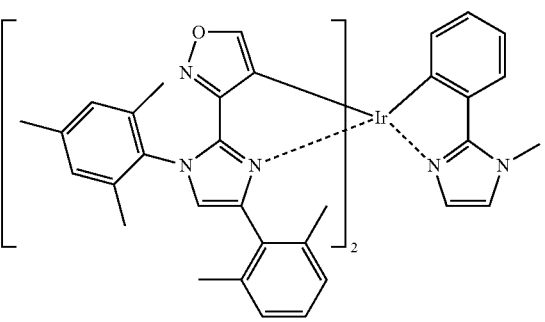

D-39 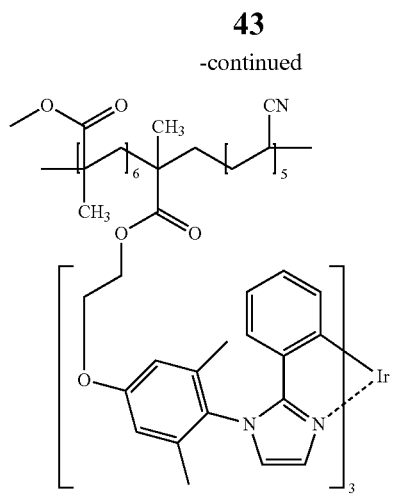
[Chemical Formula 25]
D-40 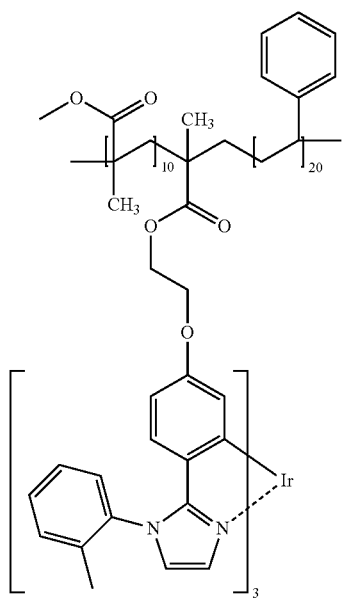
D-41 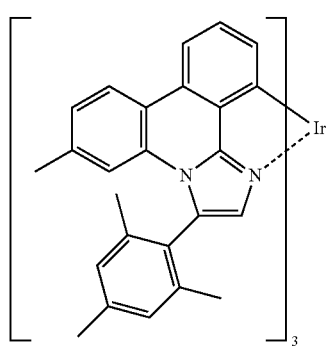
D-42 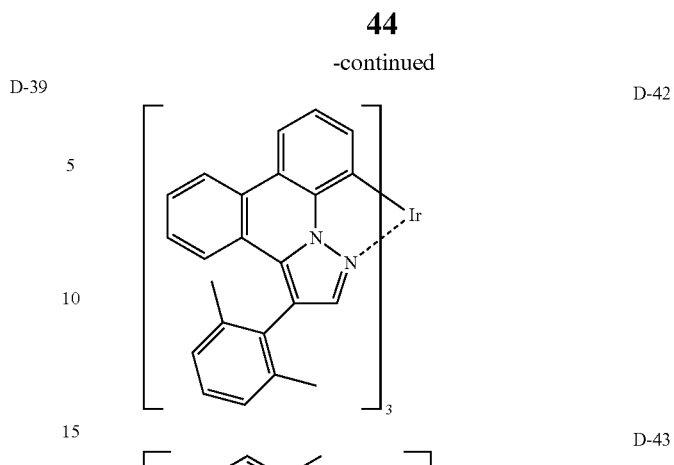
D-43 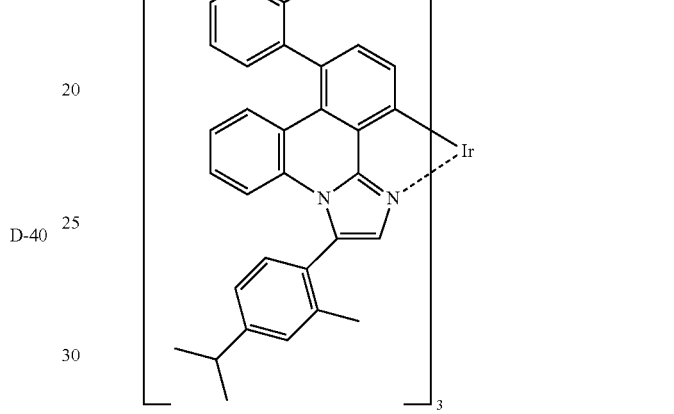
[Chemical Formula 26]
D-44 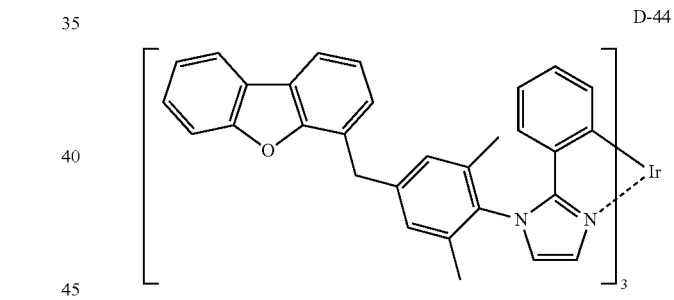
D-45 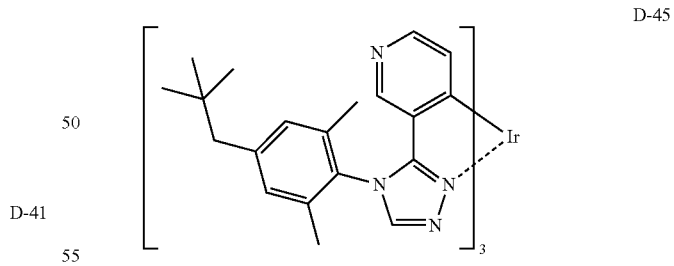
D-46 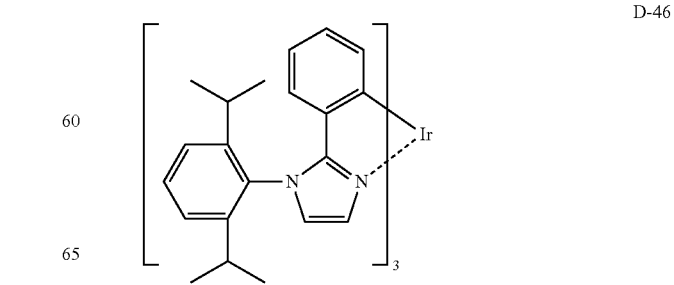

D-47

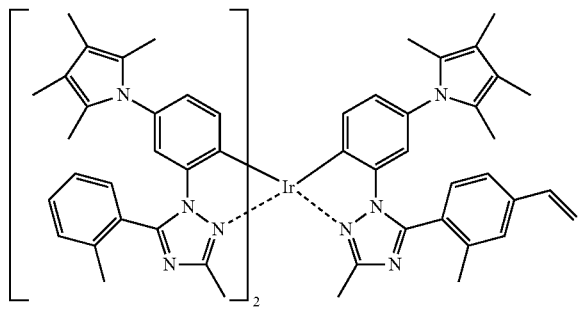

[Host Compound]

The host compound (also referred to as luminescent host or luminescent host compound) that can be used in the present invention is defined as a compound whose mass ratio in the light-emitting layer is 20% or more with respect to the total mass of compounds contained in the light-emitting layer and whose phosphorescence quantum yield of phosphorescence emission at room temperature (25° C.) is less than 0.1. Preferably, the phosphorescence quantum yield is less than 0.01. Further, the mass ratio of the host compound contained in the light-emitting layer is preferably 20% or more with respect to the total mass of compounds contained in the light-emitting layer.

The host compound that can be used in the present invention is not particularly limited, and may be a compound conventionally used in organic EL elements. Typical examples of such a host compound include carbazol derivatives, triarylamine derivatives, aromatic derivatives, nitrogen-containing heterocyclic compounds, thiophene derivatives, furan derivatives, compounds having basic skeletons of, for example, oligoarylene compounds, carboline derivatives, diazacarazol derivatives (here, diazacarbazol derivative refers to a compound obtained by substituting, with a nitrogen atom, at least one carbon atom on a hydrocarbon ring constituting the carboline ring of a carbolin derivative), and the like.

The known host compound that can be used in the present invention is preferably a compound that has hole transportability and electron transportability, can prevent emission of light with a longer wavelength, and has high Tg (glass transition temperature).

Further, in the present invention, conventionally-known host compounds may be used singly or in combination of two or more of them. The use of two or more host compounds makes it possible to control charge migration and therefore to increase the efficiency of the organic EL element. Further, the use of two or more kinds of the iridium complexes according to the present invention used as the phosphorescent dopants and/or two or more kinds of conventionally-known compounds makes it possible to mix different luminescences and therefore to obtain any emission color.

Further, the host compound used in the present invention may be either a low-molecular compound or a high-molecular compound having a repeating unit, or may be a low-molecular compound (polymerizable host compound) having a polymerizable group such as a vinyl group or an epoxy group. Such compounds may be used singly or in combination of two or more of them.

Specific examples of the known host compound include compounds described in the following literatures:

JP 2001-257076 A, JP 2002-308855 A, JP 2001-313179 A, JP 2002-319491 A, JP 2001-357977 A, JP 2002-334786 A, JP 2002-8860 A, JP 2002-334787 A, JP 2002-15871 A, JP 2002-334788 A, JP 2002-43056A, JP 2002-334789 A, JP 2002-75645 A, JP 2002-338579 A, JP 2002-105445 A, JP 2002-343568 A, JP 2002-141173 A, JP 2002-352957 A, JP 2002-203683 A, JP 2002-363227 A, JP 2002-231453 A, JP 2003-3165 A, JP 2002-234888 A, JP 2003-27048 A, JP 2002-255934 A, JP 2002-260861 A, JP 2002-280183 A, JP 2002-299060 A, JP 2002-302516 A, JP 2002-305083 A, JP 2002-305084 A, and JP 2002-308837 A Specific examples of a compound used as the host compound in the light-emitting layer of the organic EL element according to the present invention will be given below, but the present invention is not limited thereto.

[Chemical Formula 27]

OC-1

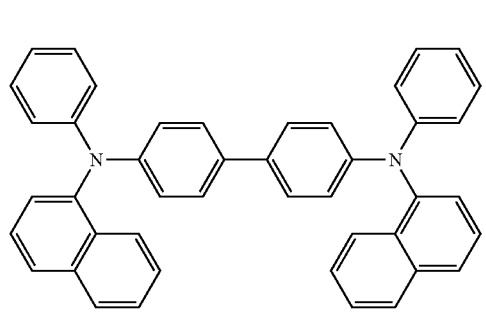

OC-2

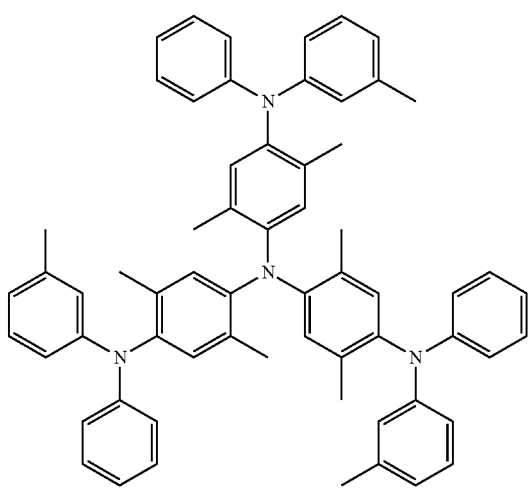

-continued
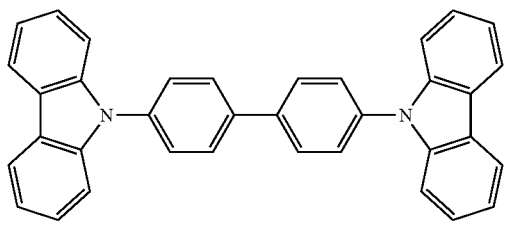
OC-3
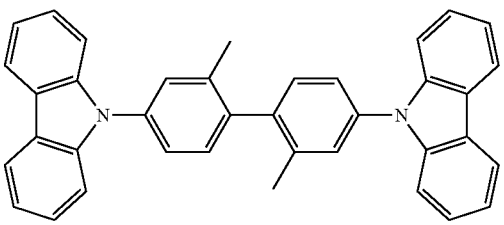
OC-4
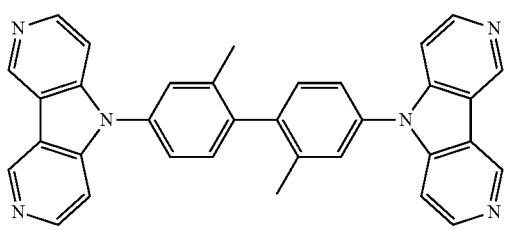
OC-5
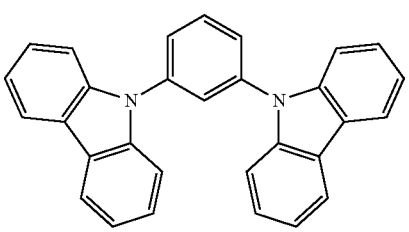
OC-6
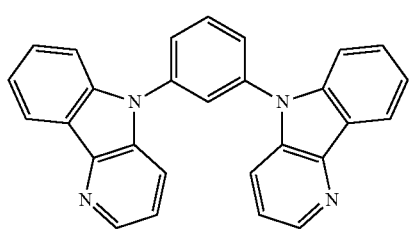
OC-7
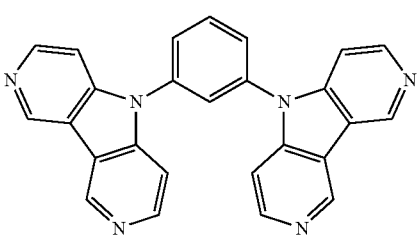
OC-8
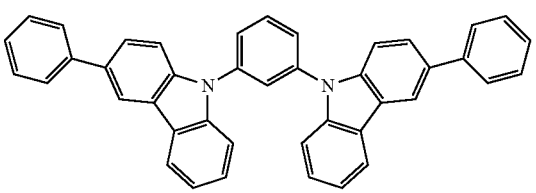
OC-10
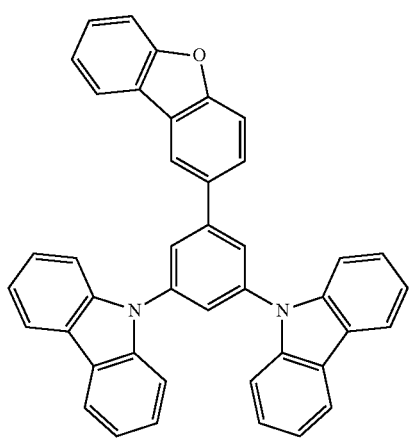
OC-9
[Chemical Formula 28]
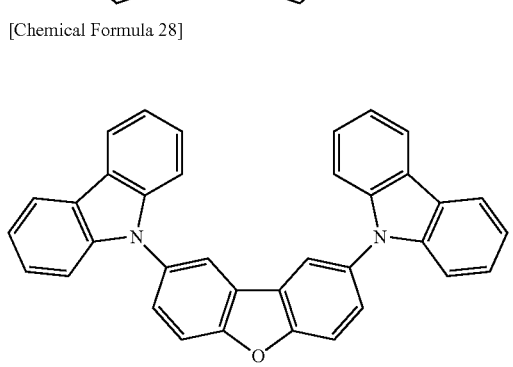
OC-11
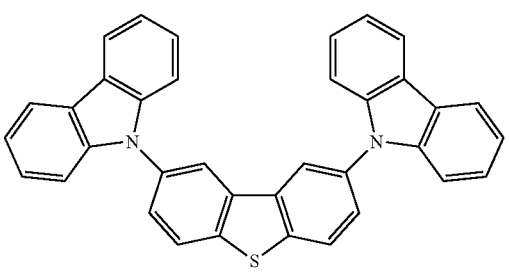
OC-12

-continued
OC-13
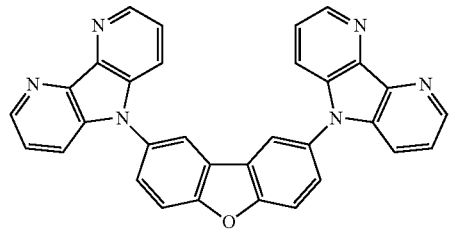
OC-14
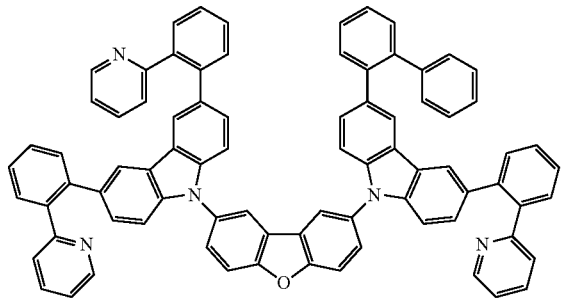
OC-15
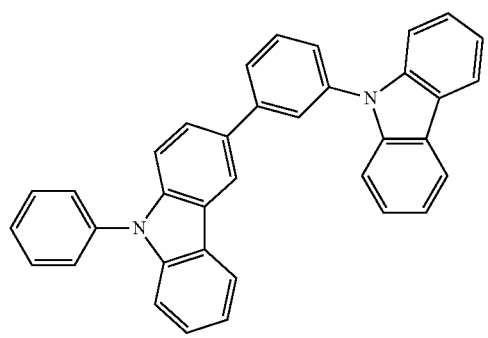
OC-16
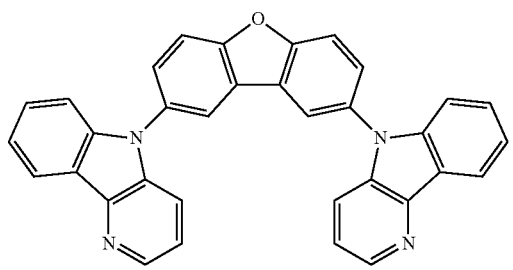
OC-17
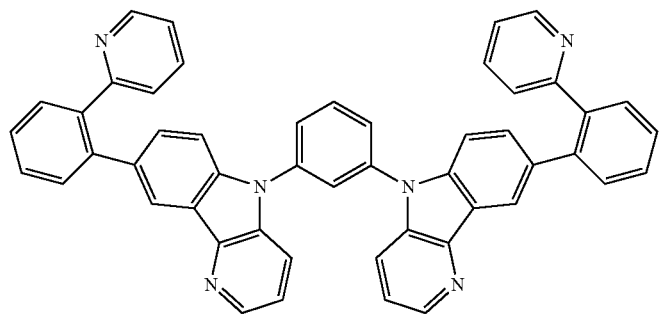
[Chemical Formula 29]
OC-18
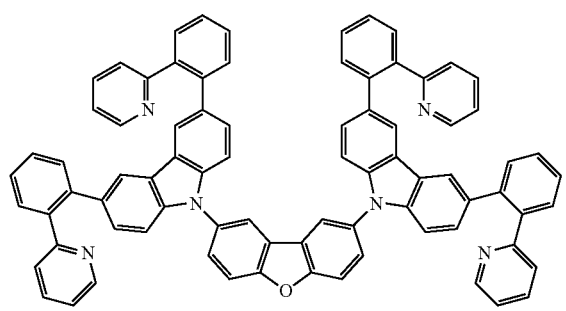
OC-19
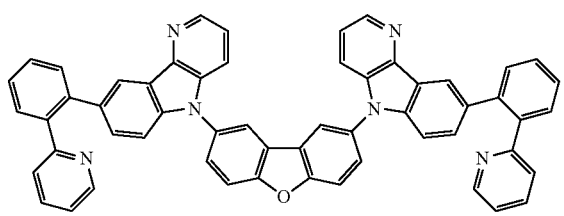

-continued
OC-20
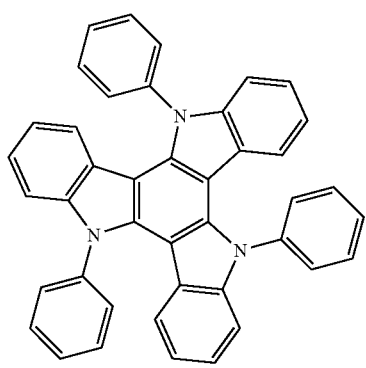
OC-21
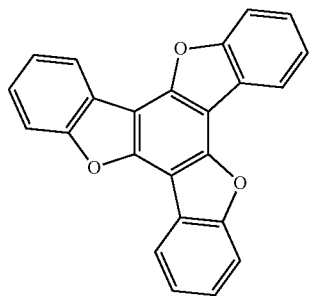
OC-22
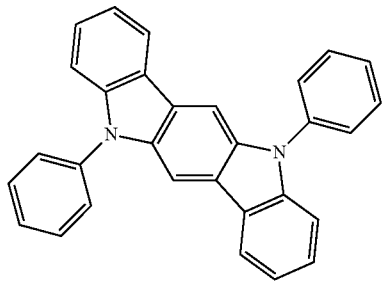
OC-23
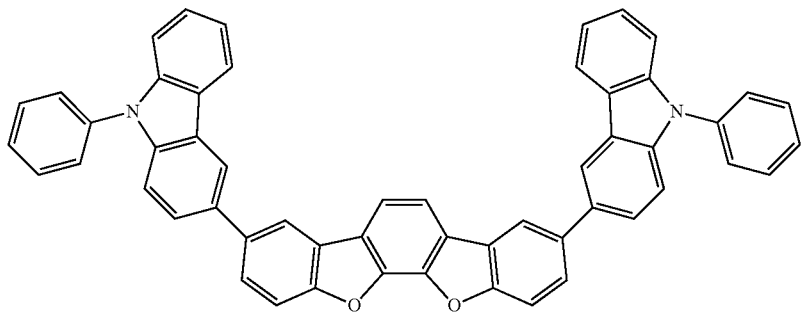
[Chemical Formula 30]
OC-24
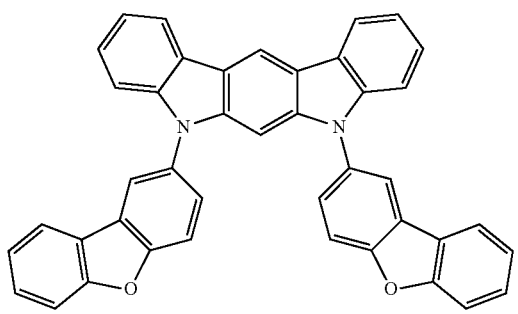
OC-25
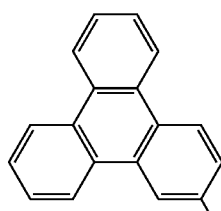
OC-26
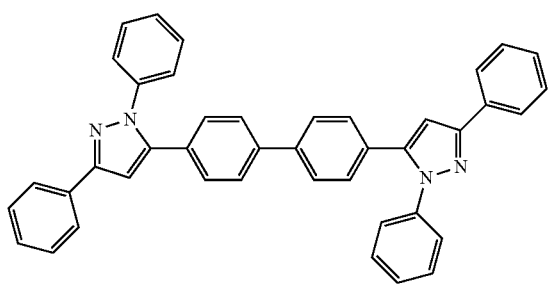
OC-27
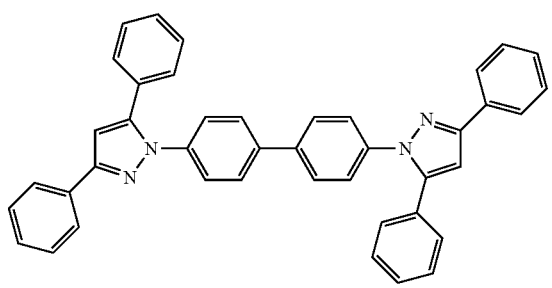

-continued

OC-28

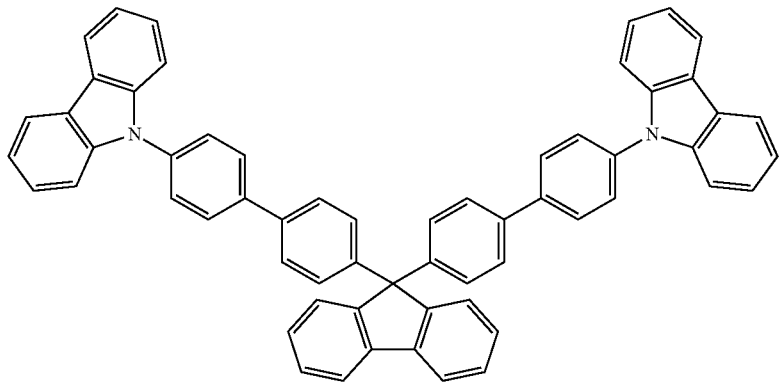

[Chemical Formula 31]

OC-29　　　　　　　　　　　　　　　OC-30

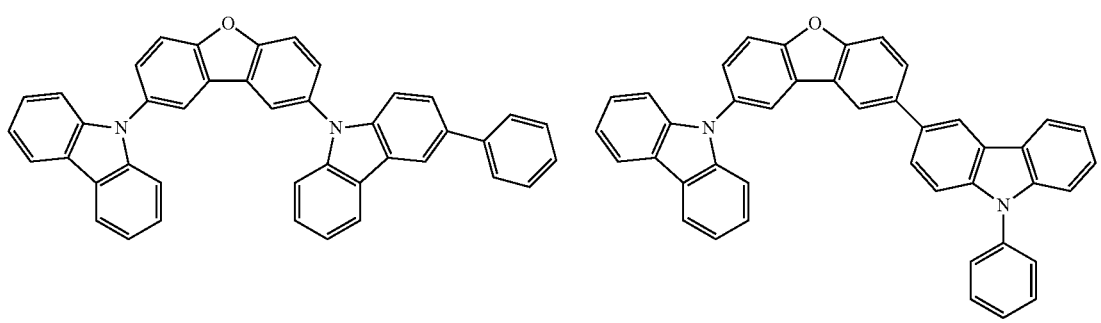

OC-31　　　　　　　　　　　　　　　OC-32

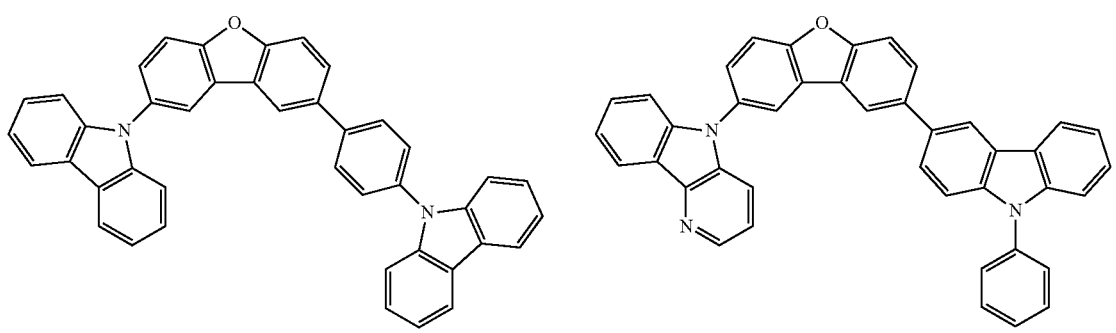

Further, a compound represented by the following general formula (B) or (E) is particularly preferred as the host compound in the light-emitting layer of the organic EL element according to the present invention.

[Chemical Formula 32]

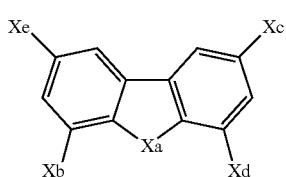

General Formula (B)

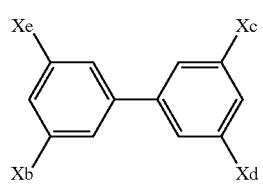

General Formula (E)

In the general formulas (B) and (E), Xa is O or S, Xb, Xc, Xd, and Xe are each a hydrogen atom, a substituent group, or a group represented by the following general formula (C), at least one of Xb, Xc, Xd, and Xe is a group represented by the following general formula (C), and Ar in at least one of the groups represented by the following general formula (C) is a carbazolyl group.

Ar-(L$_4$)$n$-*　　　　　　　General Formula (C)

In the general formula (C), L$_4$ is a divalent linking group derived from an aromatic hydrocarbon ring or an aromatic heterocycle; n is an integer of 0 to 3, and when n is 2 or more, two or more L$_4$s may be the same or different; * is a linking site to the general formula (B) or (E); and Ar is a group represented by the following general formula (D).

[Chemical Formula 33]

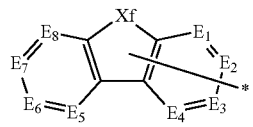

General Formula (D)

In the general formula (D), Xf is N(R″), O, or S, E$_1$ to E$_8$ are each C(R″$_1$) or N, R″ and R″$_1$ are each a hydrogen atom, a substituent group, or a linking site to L$_4$ in the general formula (C), and * is a linking site to L$_4$ in the general formula (C).

In the compound represented by the above general formula (B), at least two of Xb, Xc, Xd, and Xe are preferably represented by the general formula (C), and more preferably, Xc is represented by the general formula (C) wherein Ar is a carbazolyl group that may have a substituent group.

Specific examples of the compound represented by the general formula (B) that is preferably used as the host compound in the light-emitting layer of the organic EL element according to the present invention will be given below, but the present invention is not limited thereto.

[Chemical Formula 34]

1

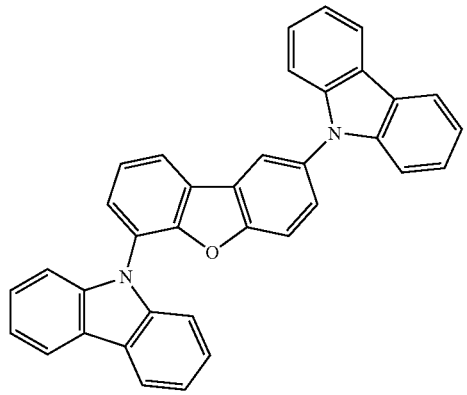

2

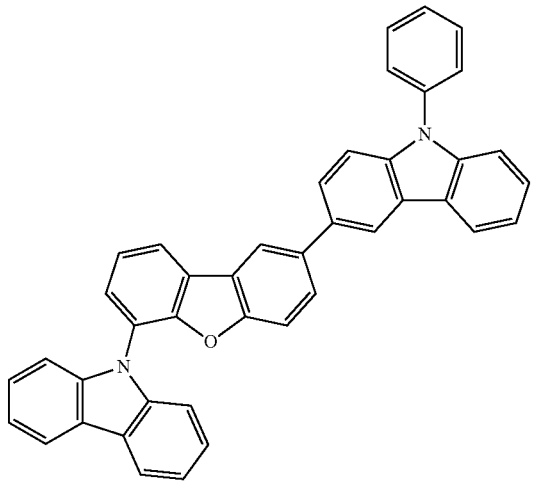

3

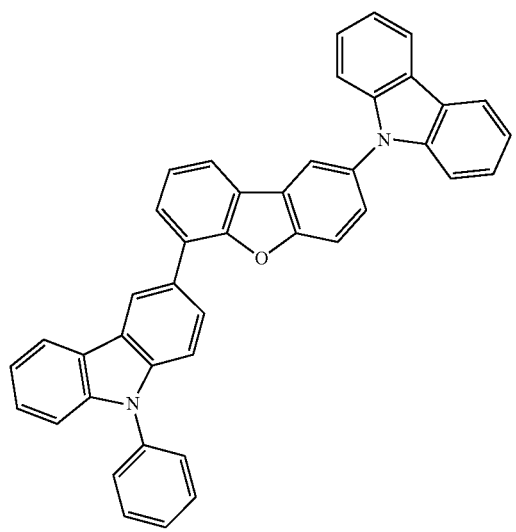

4

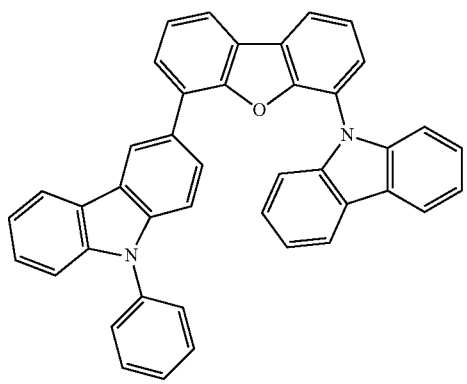

-continued
5
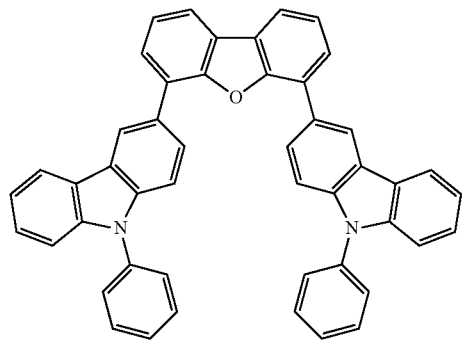
6
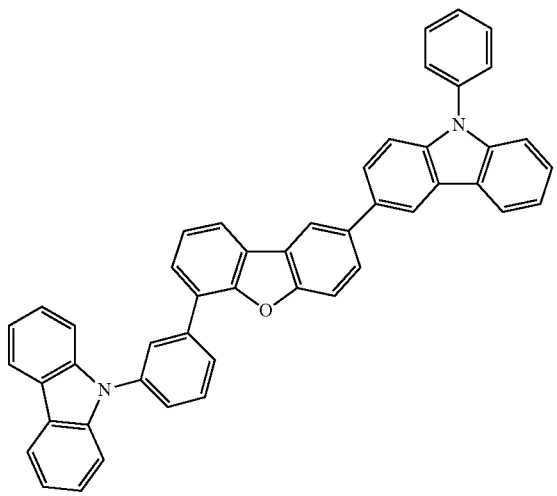
[Chemical Formula 35]
7
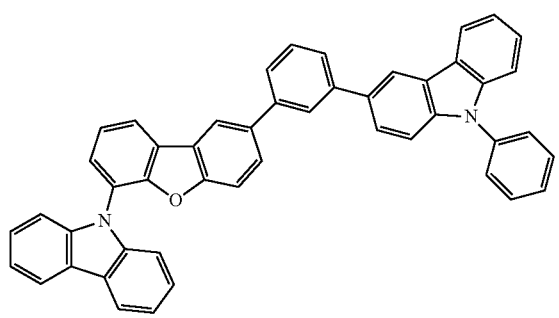
8
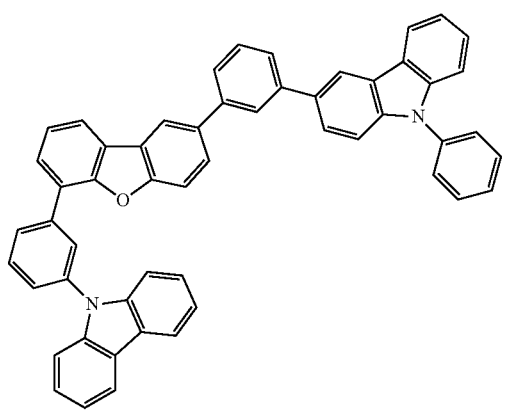
9
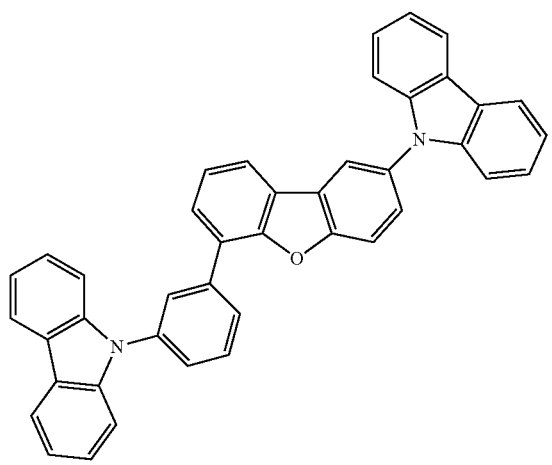
10
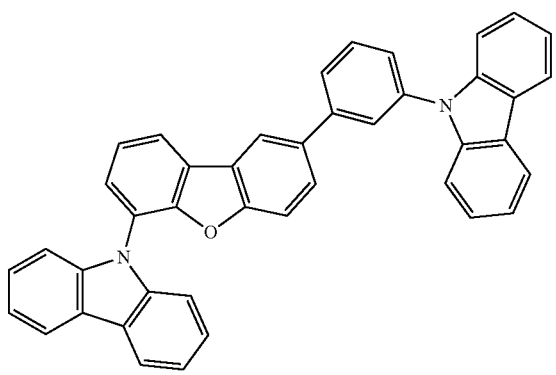

-continued
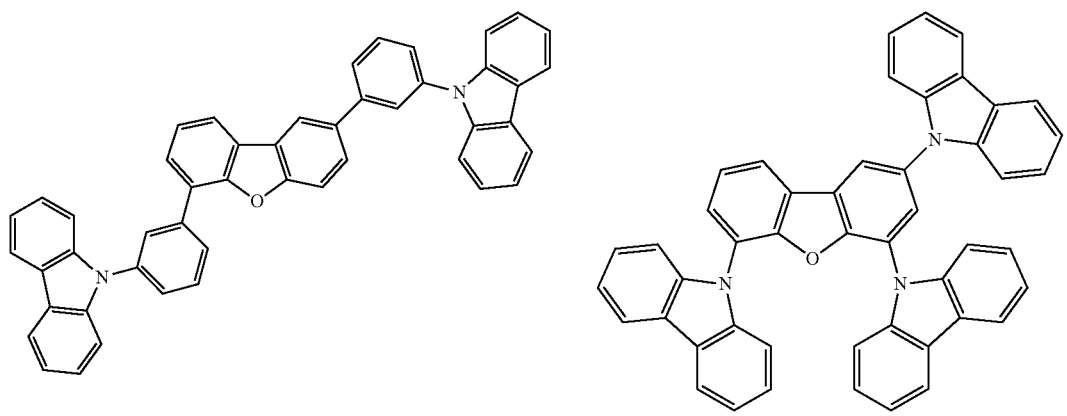
[Chemical Formula 36]
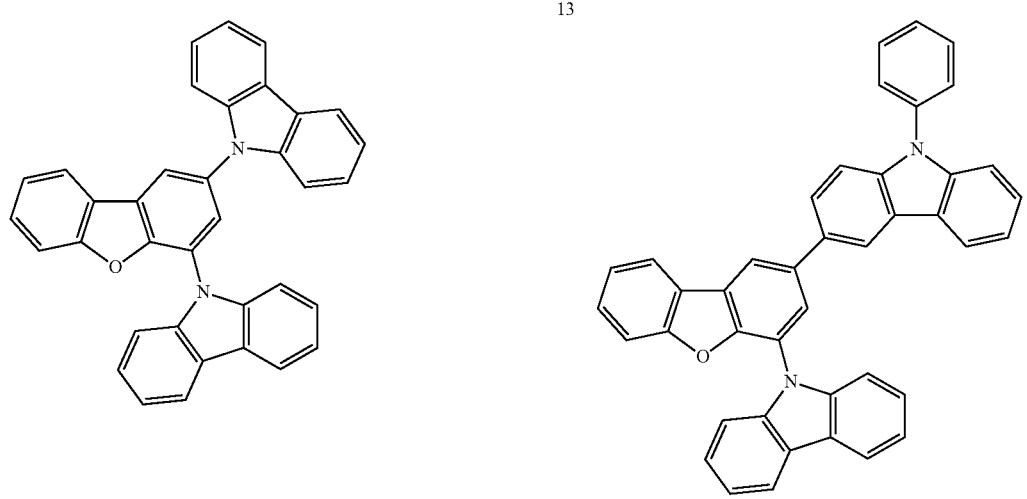
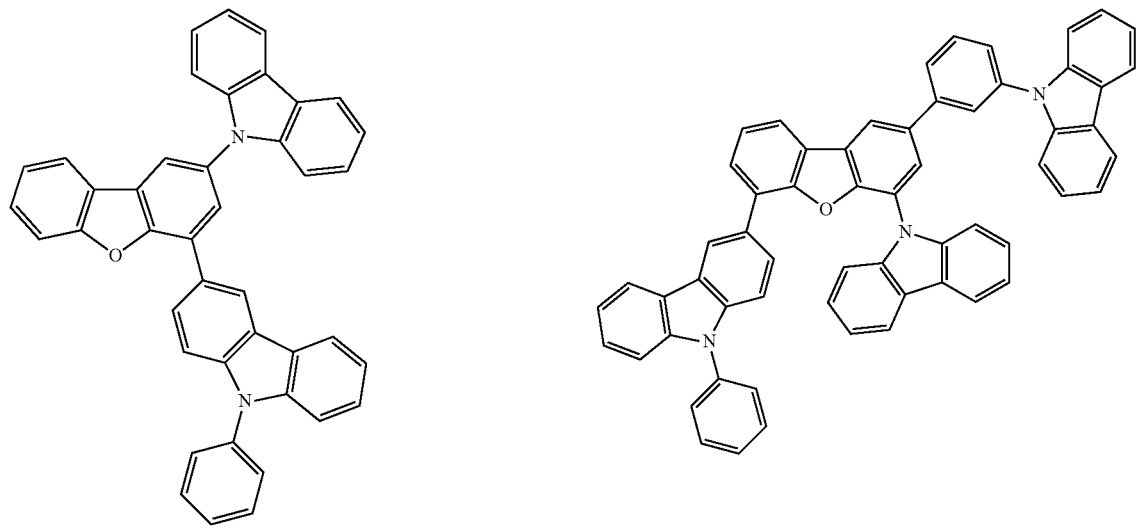

-continued
17
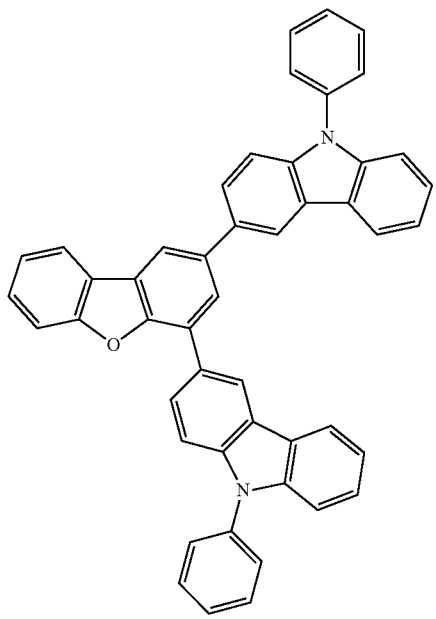
18
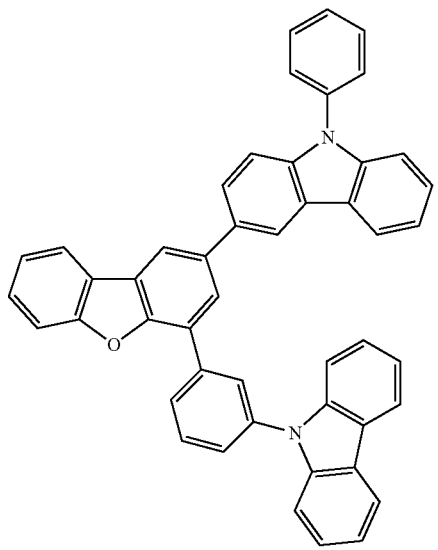
[Chemical Formula 37]
19
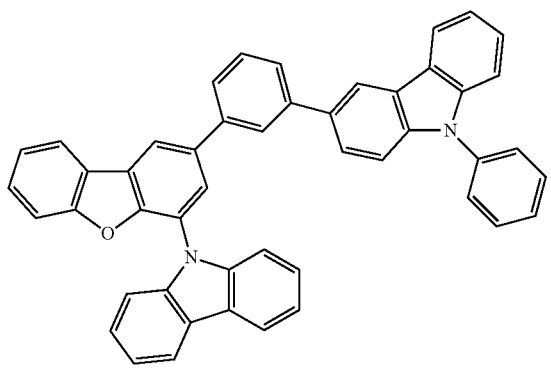
20
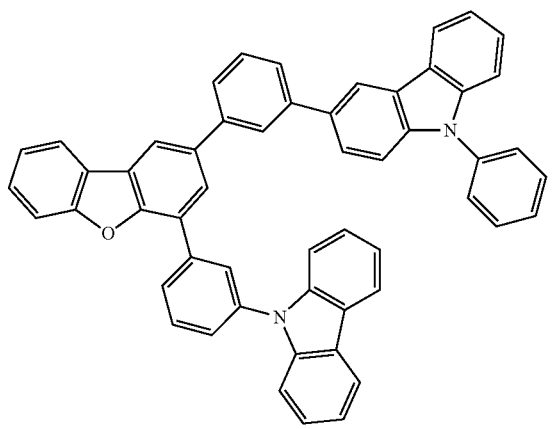
21
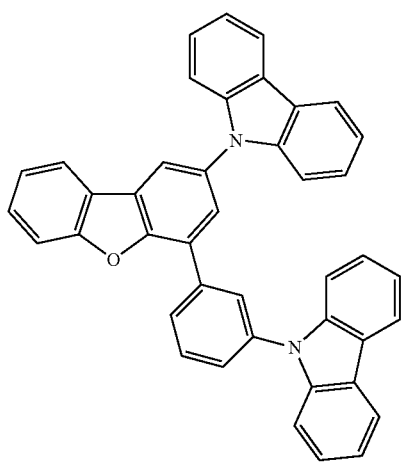
22
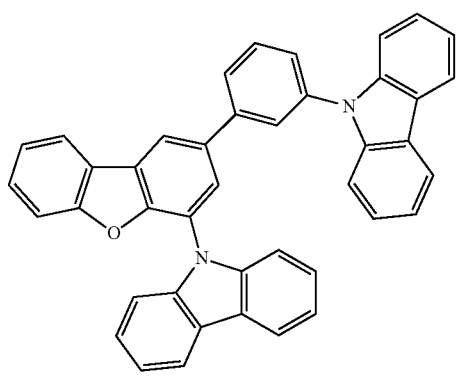

-continued
23
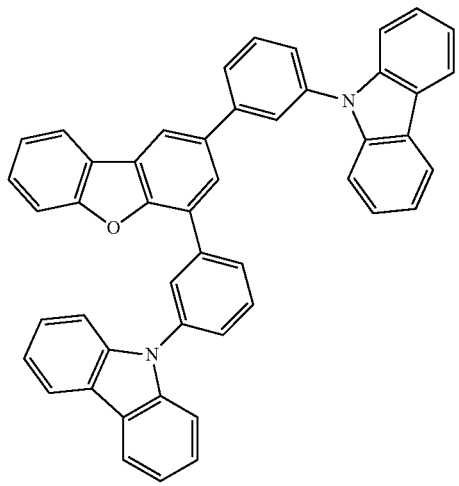
24
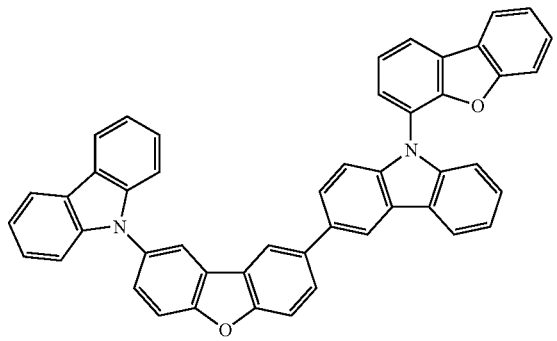
25
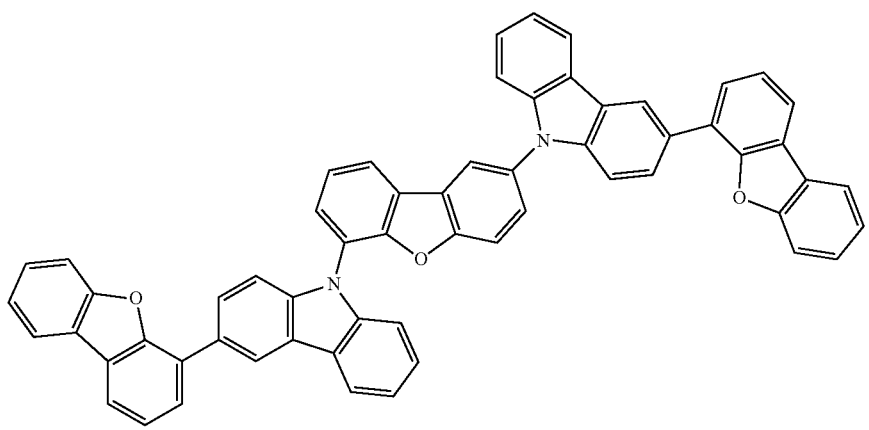
[Chemical Formula 38]
26
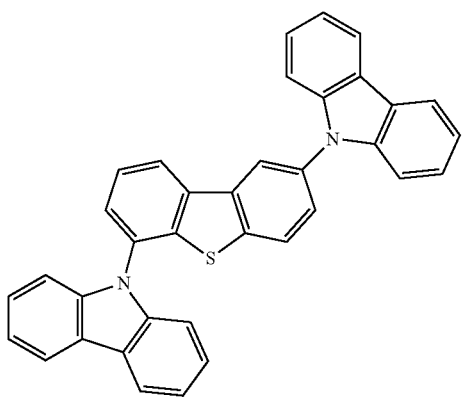

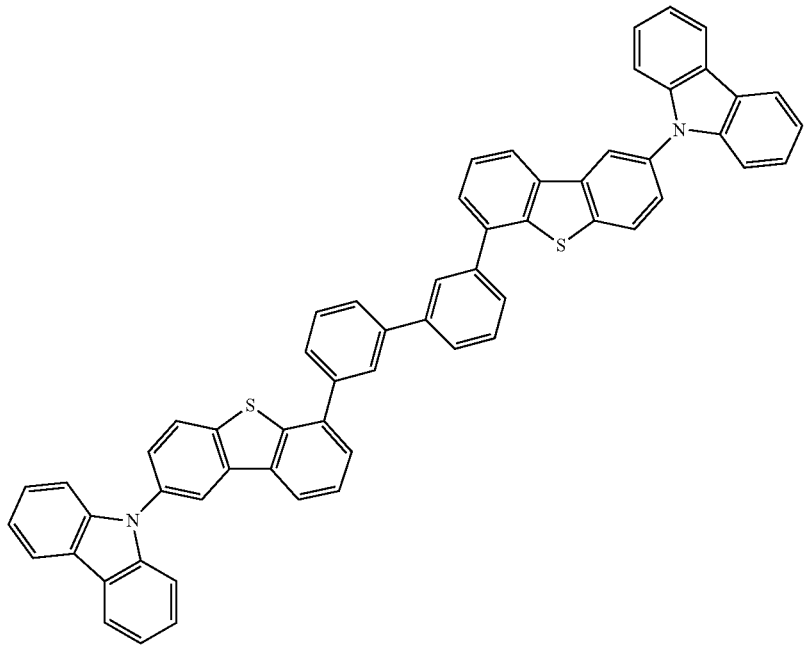
27
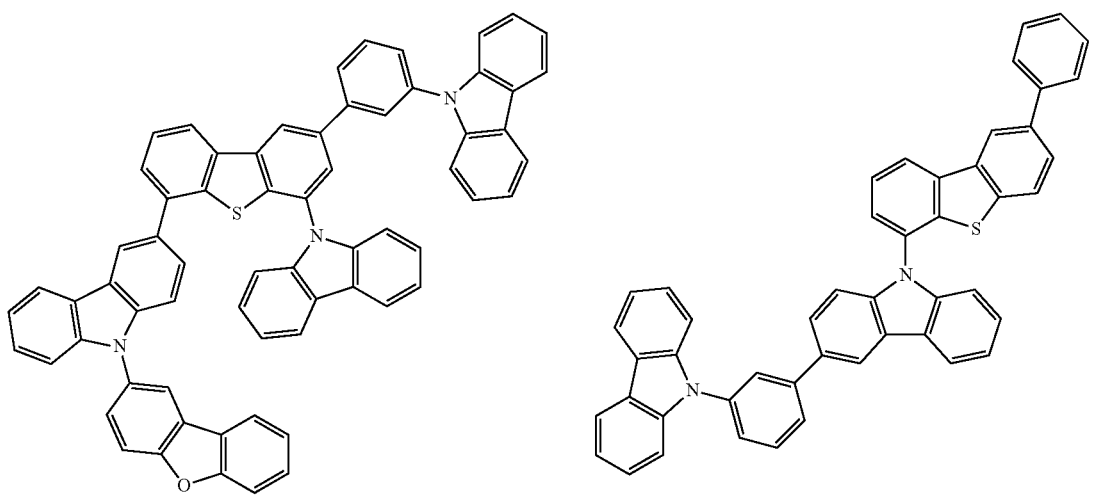
28
29
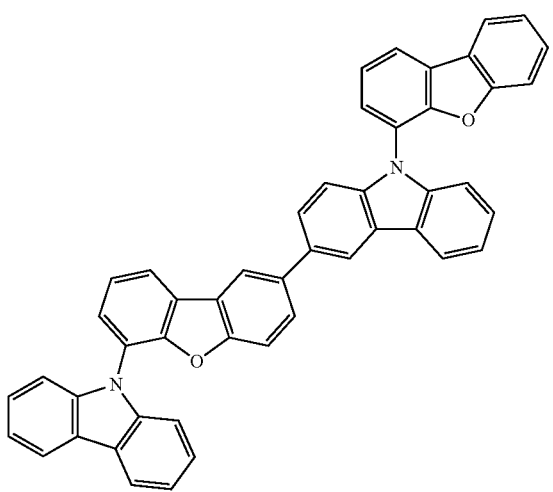
30

-continued
31
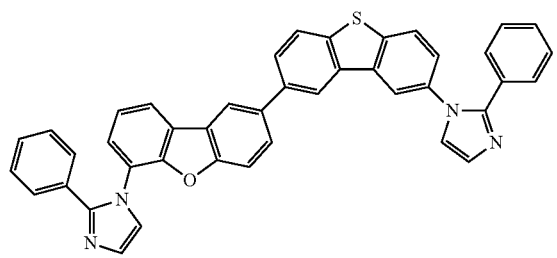
32
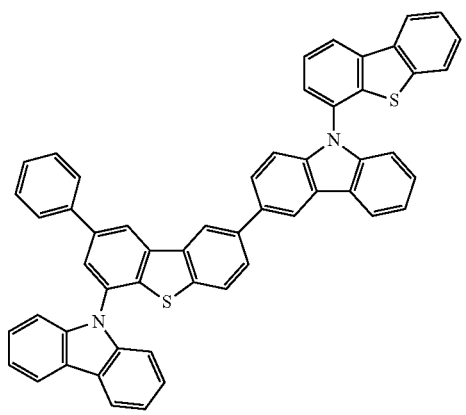
33
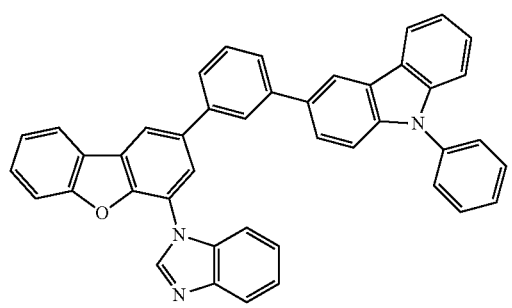
34
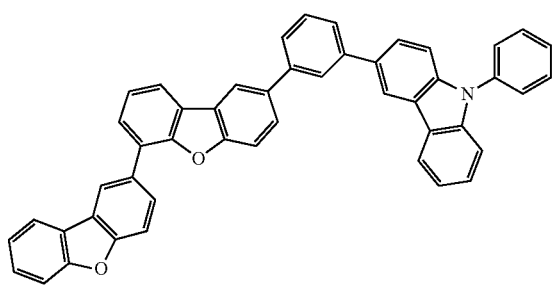
35
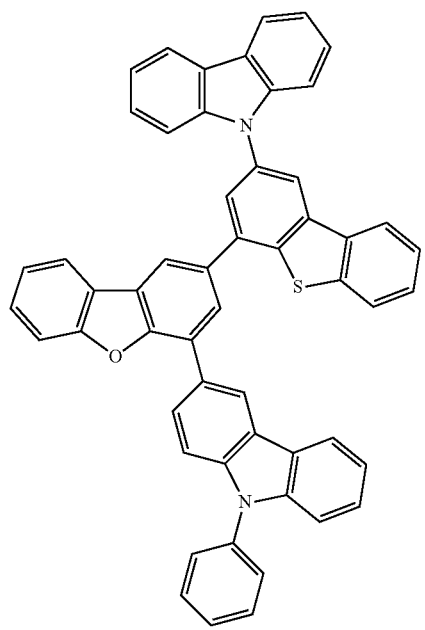
36
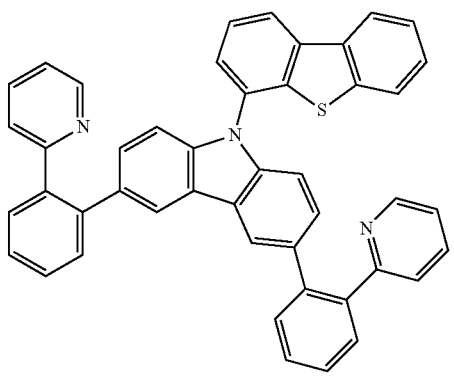

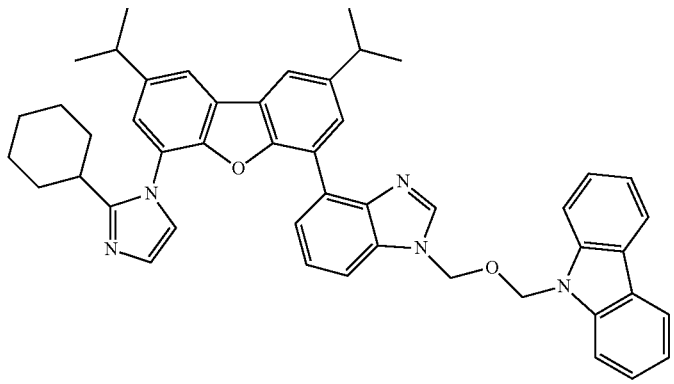
37
[Chemical Formula 40]
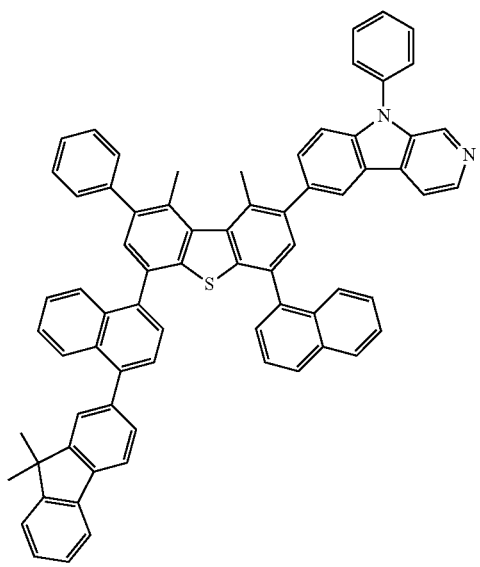
38
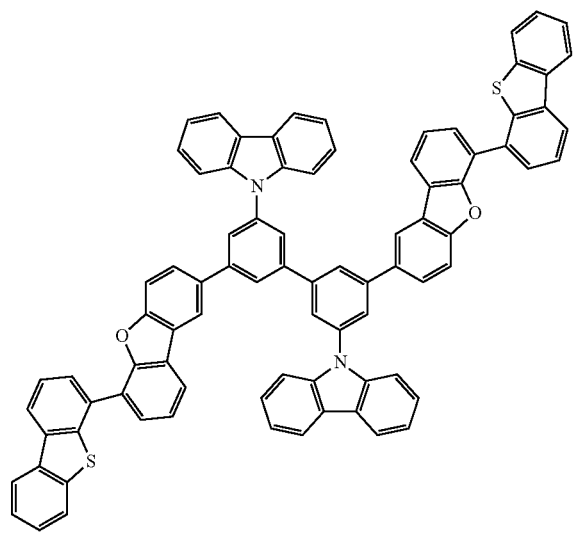
39
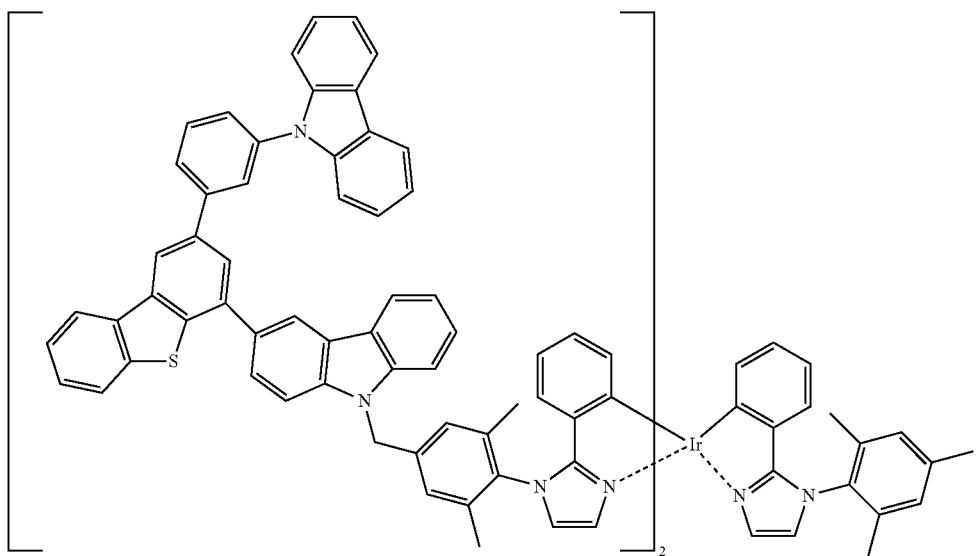
40

[Chemical Formula 41]
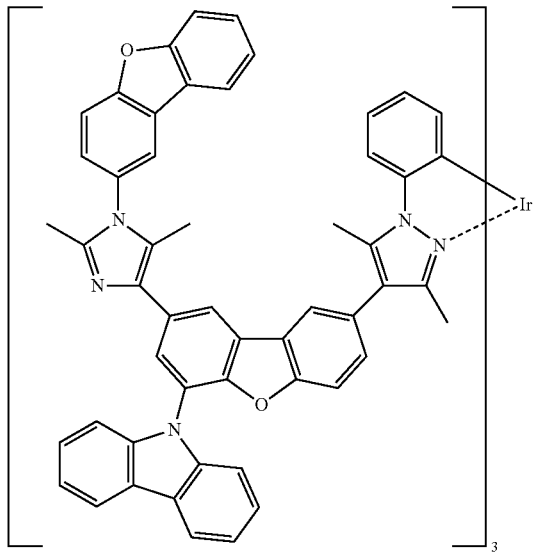
41
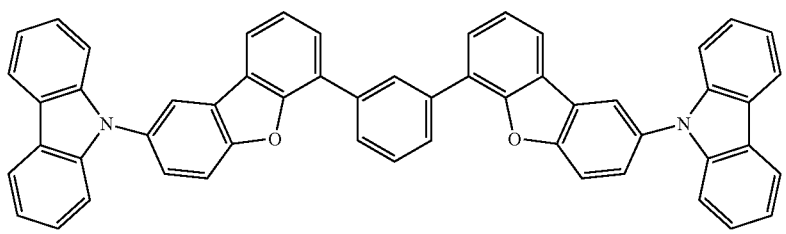
42
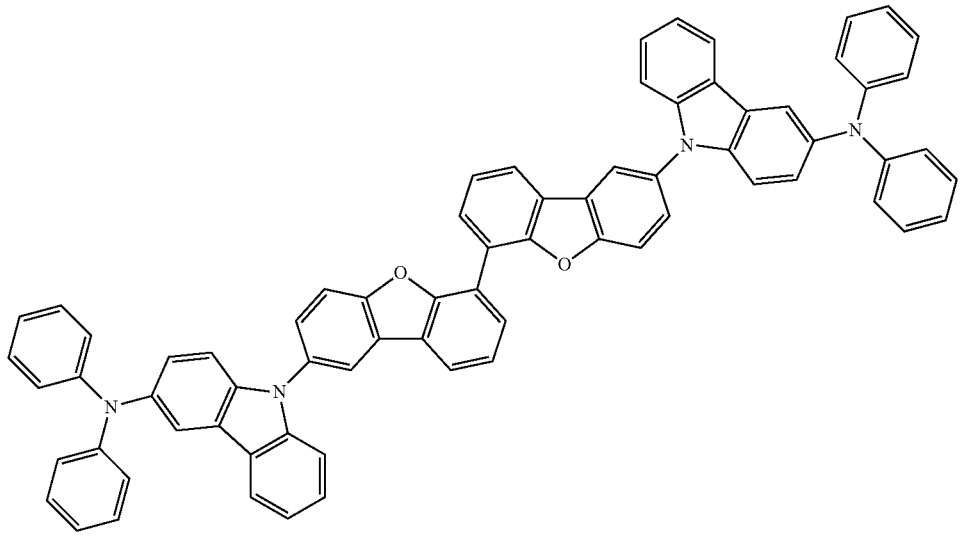
43

[Chemical Formula 42]
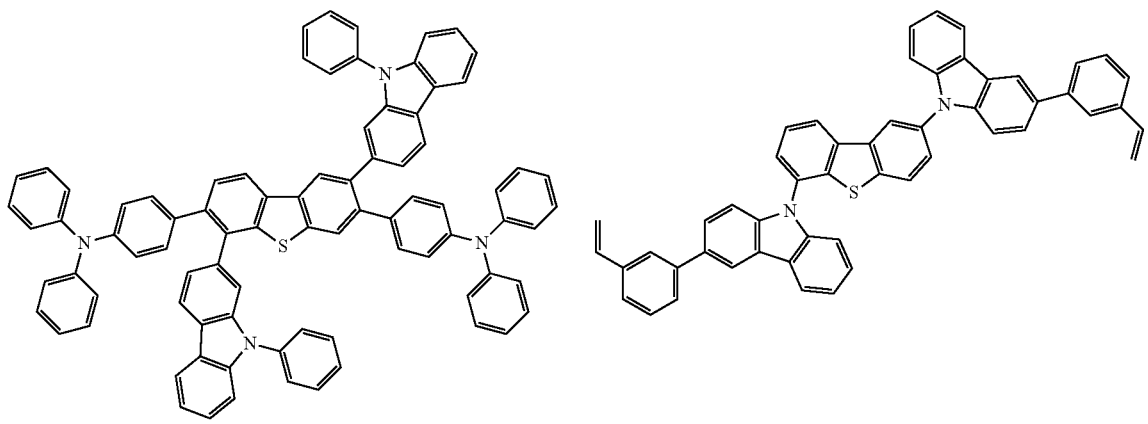
[Chemical Formula 43]
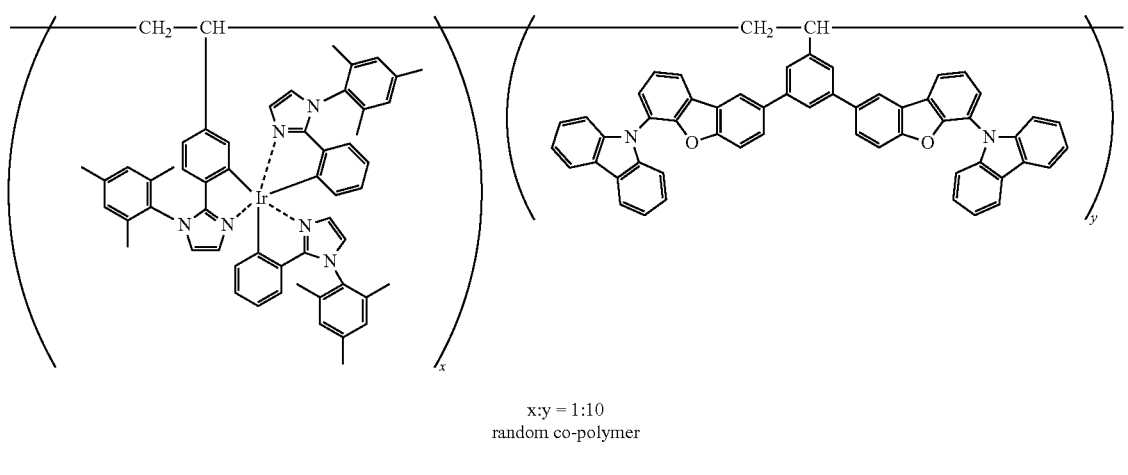
x:y = 1:10
random co-polymer
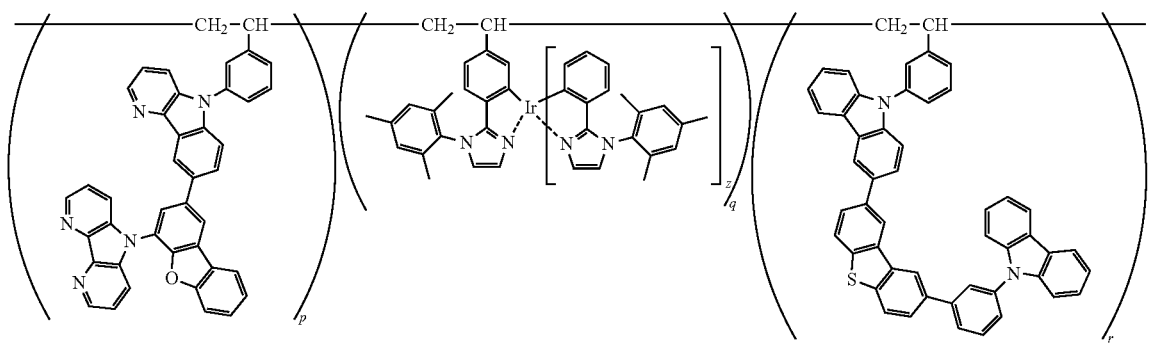

-continued
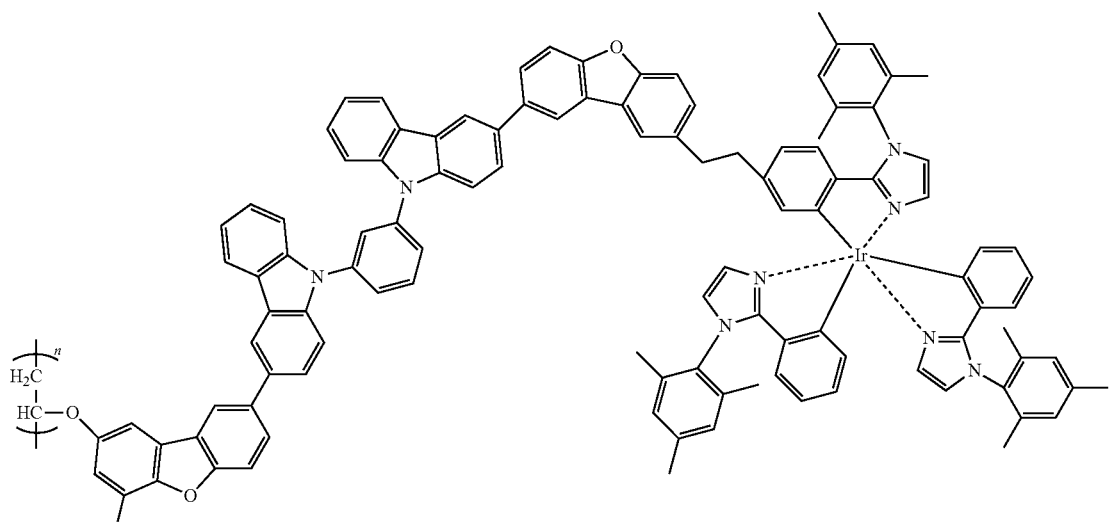
48
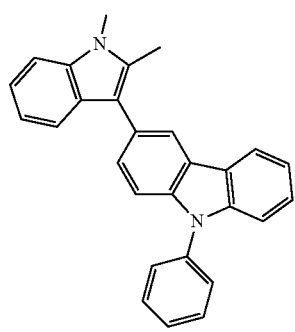
[Chemical Formula 45]
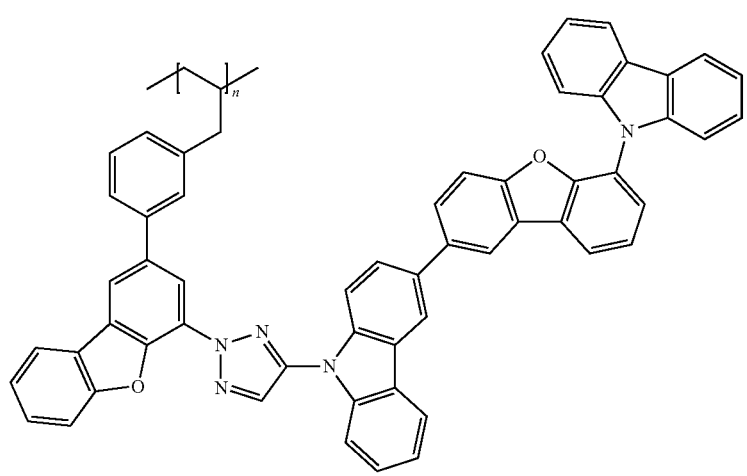
49

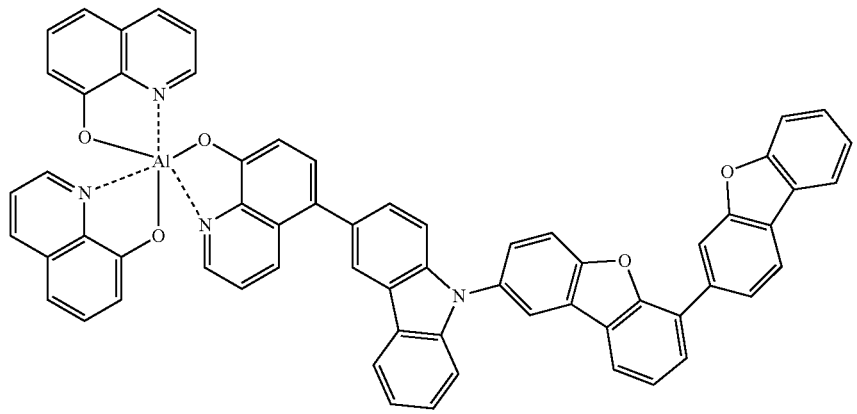
50
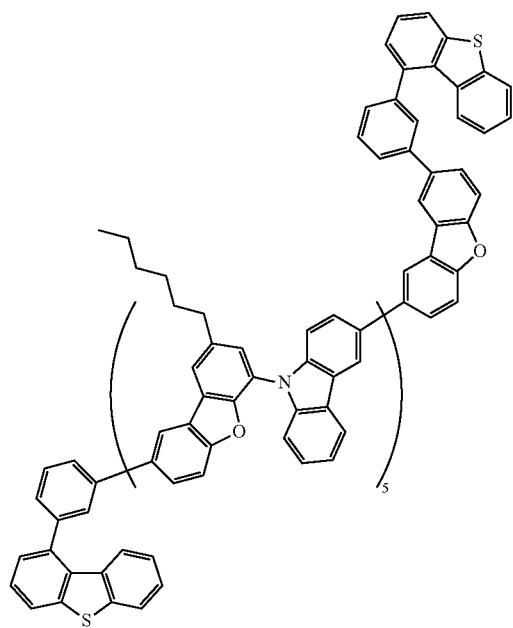
51
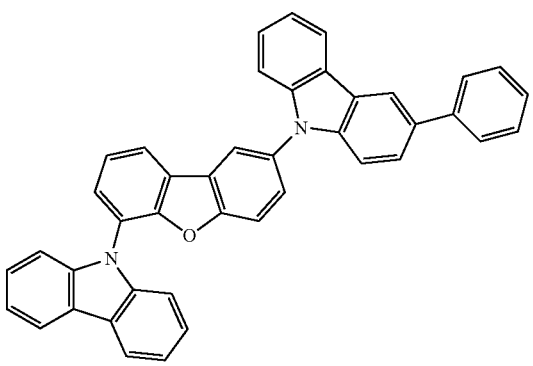
52
[Chemical Formula 46]
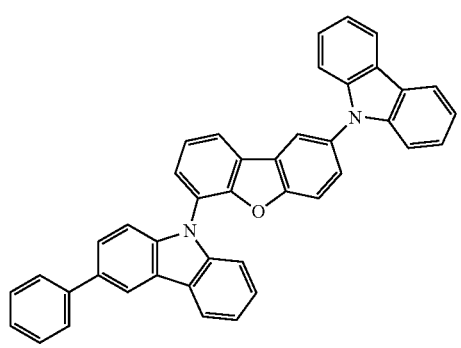
53
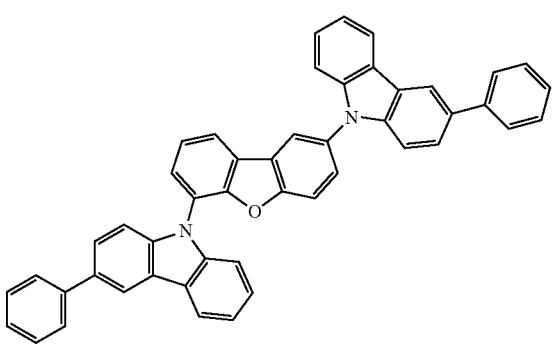
54

-continued
55
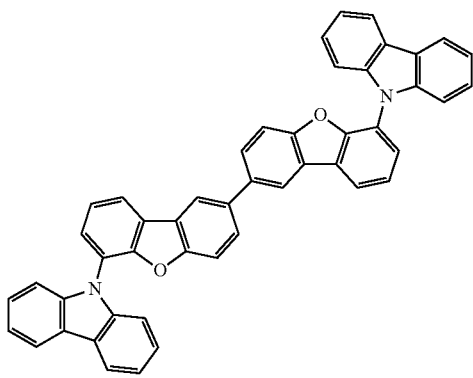
56
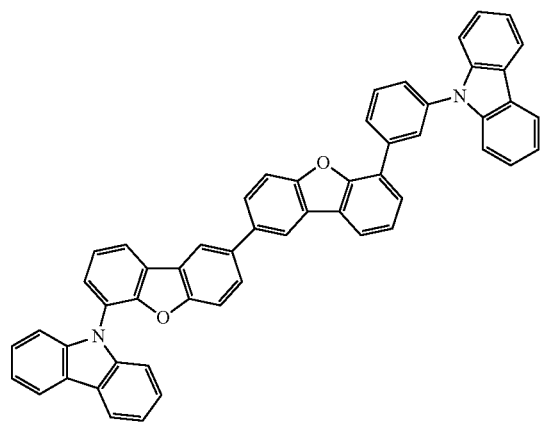
57
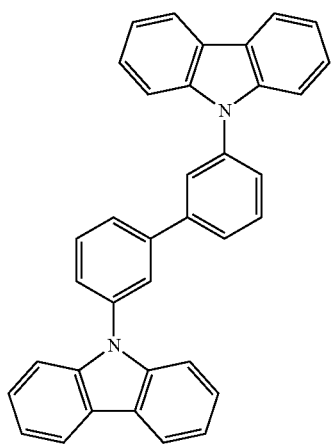
58
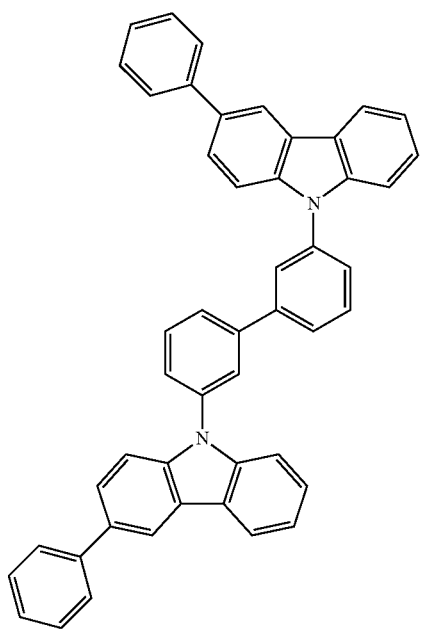
59
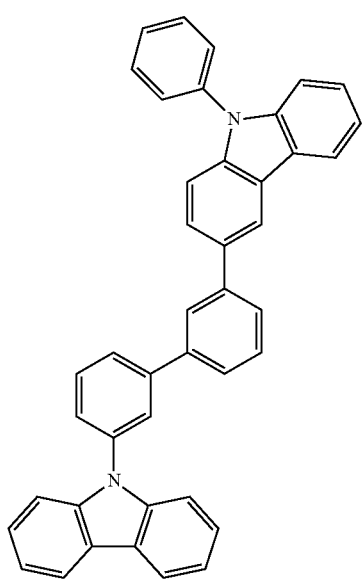

Further, a compound represented by the following general formula (B') is also particularly preferably used as the host compound in the light-emitting layer of the organic EL element according to the present invention.

[Chemical Formula 47]

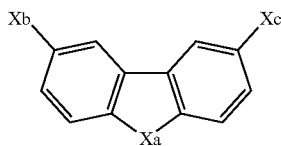

General Formula (B')

In the general formula (B'), Xa is O or S, Xb and Xc are each a substituent group or a group represented by the above general formula (C).

At least one of Xb and Xc is a group represented by the above general formula (C), and Ar in at least one of the groups represented by the general formula (C) is a carbazolyl group.

In the compound represented by the above general formula (B'), Ar in the general formula (C) is preferably a carbazolyl group that may have a substituent group, and Ar in the general formula (C) is more preferably a carbazolyl group that may have a substituent group and is linked to $L_4$ in the general formula (C) at the N position.

Specific examples of the compound represented by the general formula (B') that is preferably used as the host compound in the light-emitting layer of the organic EL element according to the present invention include OC-9, OC-11, OC-12, OC-14, OC-18, OC-29, OC-30, OC-31, and OC-32 that have been shown above as specific examples of the host compound, but the present invention is not limited thereto.

<Electron Transport Layer>

The electron transport layer is made of a material having the function of transporting electrons, and in a broad sense, an electron injection layer and a hole blocking layer are also included in the electron transport layer. The electron transport layer may be a single layer or two or more layers.

The electron transport layer shall have the function of transporting electrons injected from the cathode to the light-emitting layer, and the electron transport layer may also be made of a combination of materials arbitrarily selected from conventionally-known compounds.

Examples of such conventionally-known materials used in the electron transport layer (hereinafter, referred to as electron transport material) include: nitro-substituted fluorene derivatives; diphenylquinone derivatives; thiopyrandioxide derivatives; polycyclic aromatic hydrocarbons such as naphthalene and perylene; heterocyclic tetracarboxylic anhydrides; carbodiimides; fluorenylidenemethane derivatives; anthraquinodimethane and anthrone derivatives; oxadiazole derivatives; carboline derivatives or derivatives having a cyclic structure obtained by substituting, with a nitrogen atom, at least one carbon atom on a hydrocarbon ring constituting the carboline ring of the carboline derivative; and hexaazatriphenylene derivatives.

Further, thiadiazole derivatives obtained by substituting, with a sulfur atom, an oxygen atom on an oxadiazole ring in the oxadiazole derivative and quinoxaline derivatives having a quinoxaline ring known as an electron withdrawing group may be used as the electron transport materials.

Polymer materials having these materials introduced into the polymer chains thereof or polymer materials having these materials as the main chains thereof may also be used.

Further, metal complexes of 8-quinolinol derivatives such as tris(8-quinolinol)aluminum (Alq), tris(5,7-dichloro-8-quinolinol)aluminum, tris (5,7-dibromo-8-quinolinol)aluminum, tris(2-methyl-8-quinolinol)aluminum, tris (5-methyl-8-quinolinol)aluminum, and bis(8-quinolinol) zinc (Znq) and metal complexes obtained by replacing the central metals of these metal complexes with In, Mg, Cu, Ca, Sn, Ga, or Pb may also be used as the electron transport materials.

In addition, metal-free or metal phthalocyanines or those whose terminal is substituted with an alkyl group or a sulfonic acid group may also be used as the electronic transport materials.

Further, inorganic semiconductors such as n-type Si and n-type SiC may also be used as the electron transport materials.

The electron transport layer is preferably formed by forming a thin film of the electron transport material by, for example, a vacuum deposition method or a wet method (also referred to as wet process, and examples thereof include spin coating, casting, die coating, blade coating, roll coating, ink jetting, printing, spray coating, curtain coating, and LB (Langmuir Blodgett) process).

The layer thickness of the electron transport layer is not particularly limited, but is usually about 5 to 5000 nm, preferably 5 to 200 nm. The electron transport layer may have a single-layer structure made of one or two or more of the above materials.

Further, the electron transport layer may be doped with an n-type dopant such as a metal complex or a metal compound such as a metal halide.

Specific examples of the conventionally-known compounds (electron transport materials) preferably used for forming the electron transport layer of the organic EL element according to the present invention will be given below, but the present invention is not limited thereto.

[Chemical Formula 48]
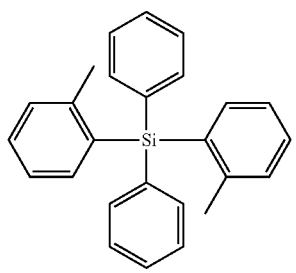
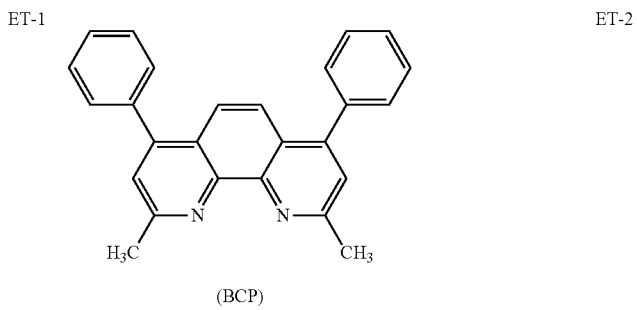
ET-1  ET-2
(BCP)
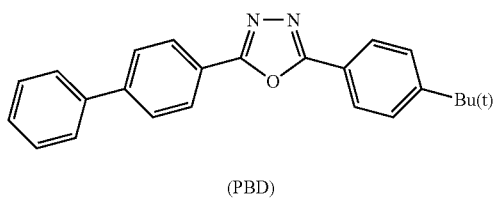
(PBD)
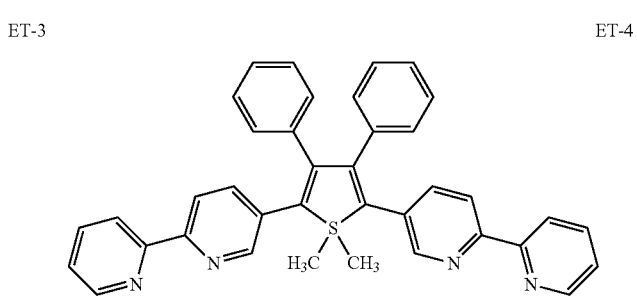
ET-3  ET-4
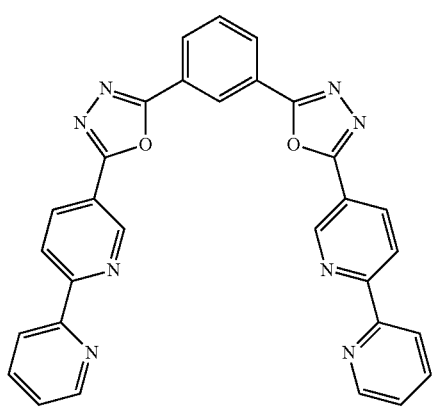
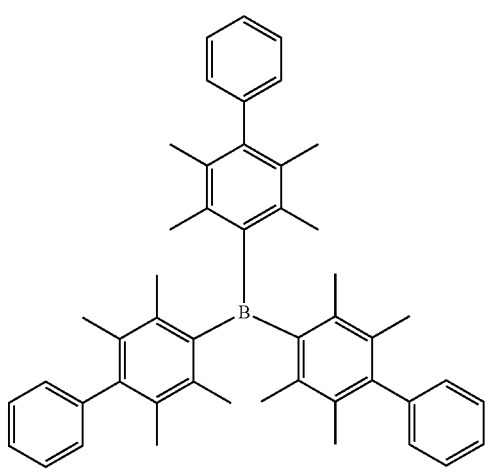
ET-5  ET-6
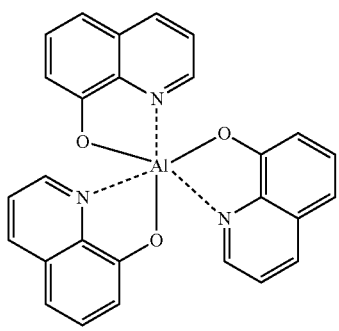
(Alq$_3$)
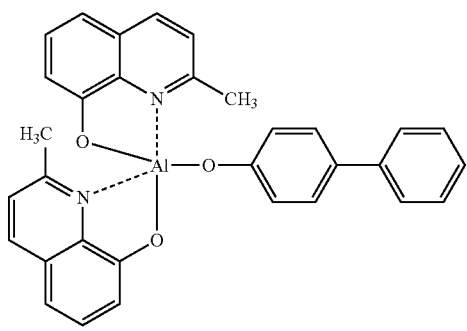
ET-7  ET-8
(BAlq)

[Chemical Formula 49]
ET-9
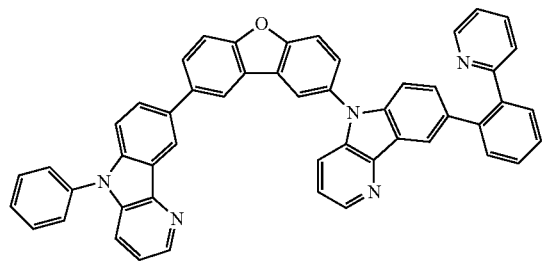
ET-10
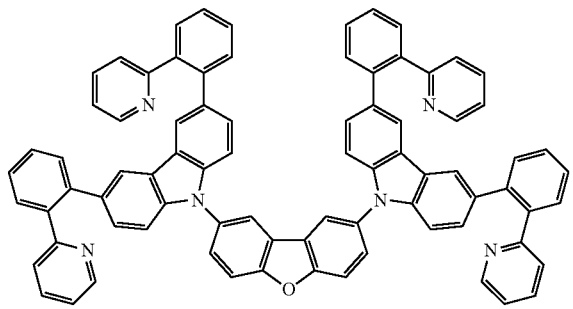
ET-11
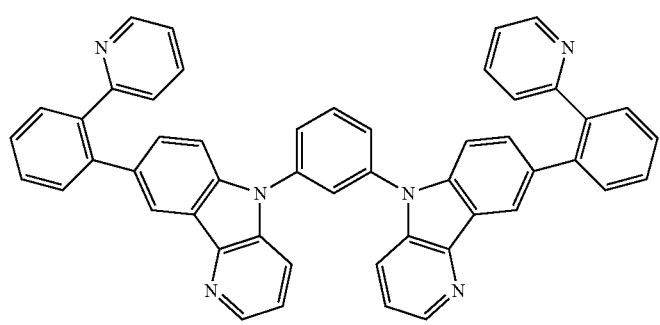
[Chemical Formula 50]
ET-12
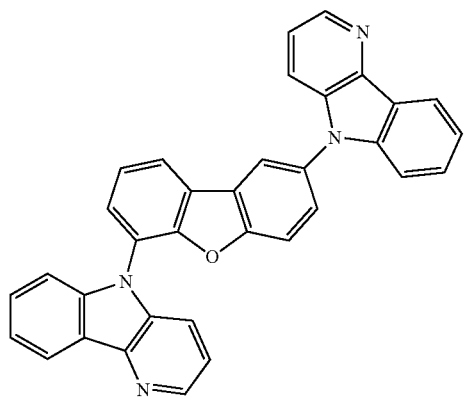
ET-13
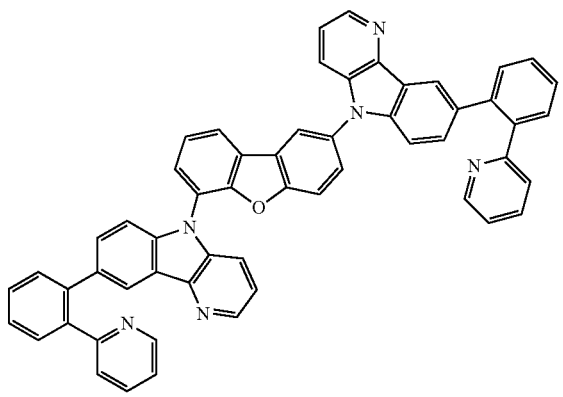

-continued
ET-14
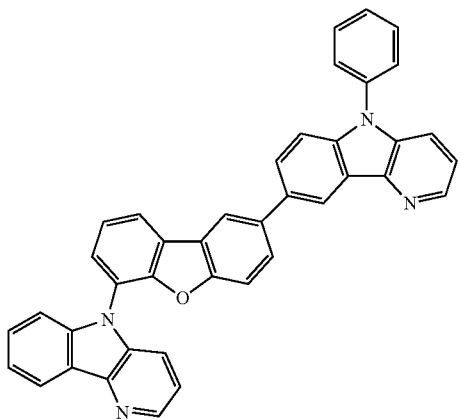
ET-15
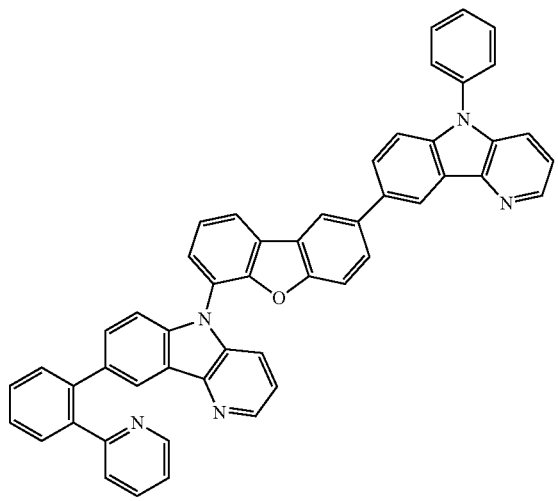
ET-16
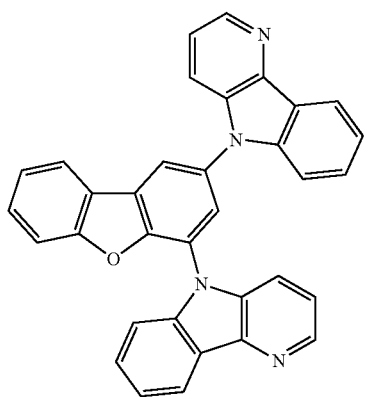
ET-17
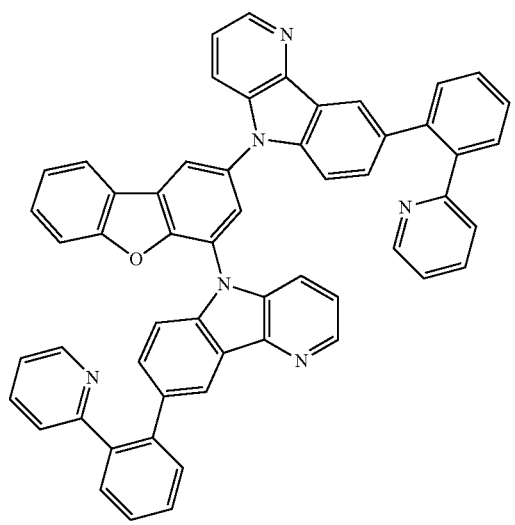
[Chemical Formula 51]
ET-18
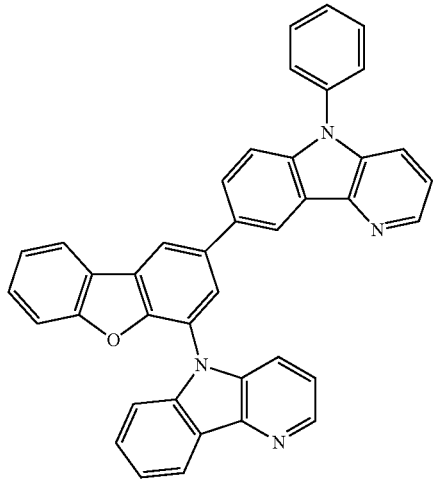
ET-19
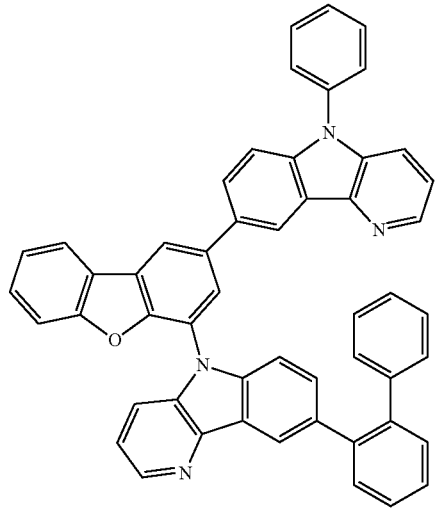

ET-20
ET-21
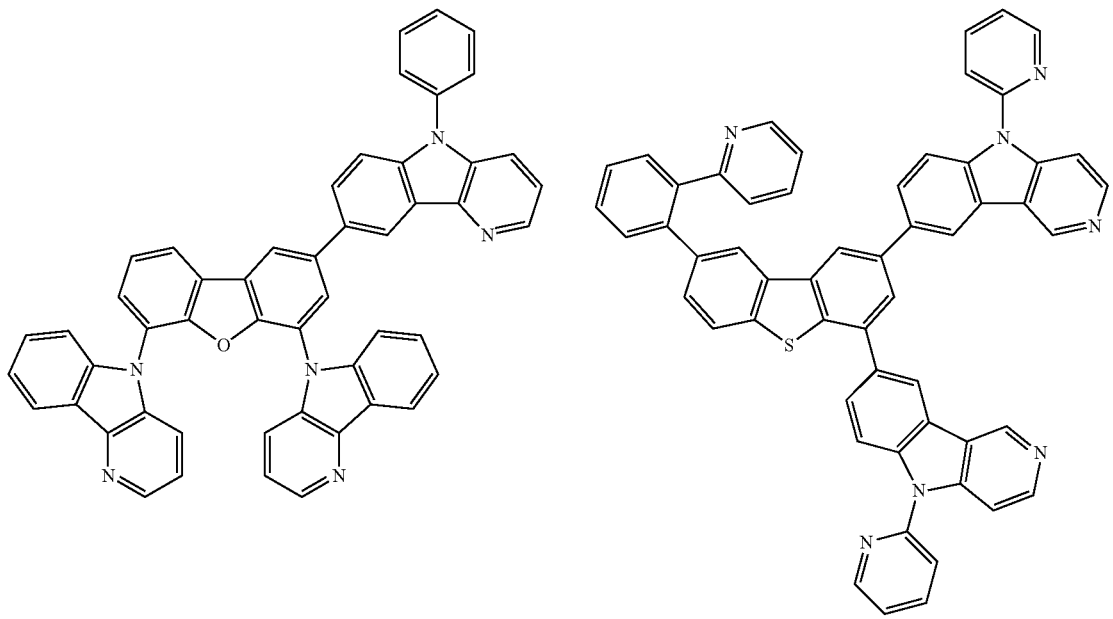
ET-22
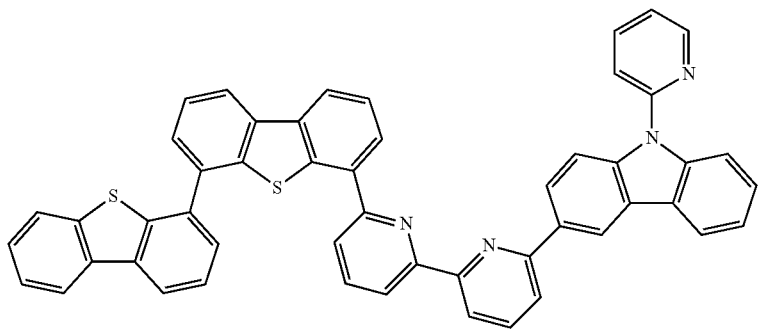
[Chemical Formula 52]
ET-23
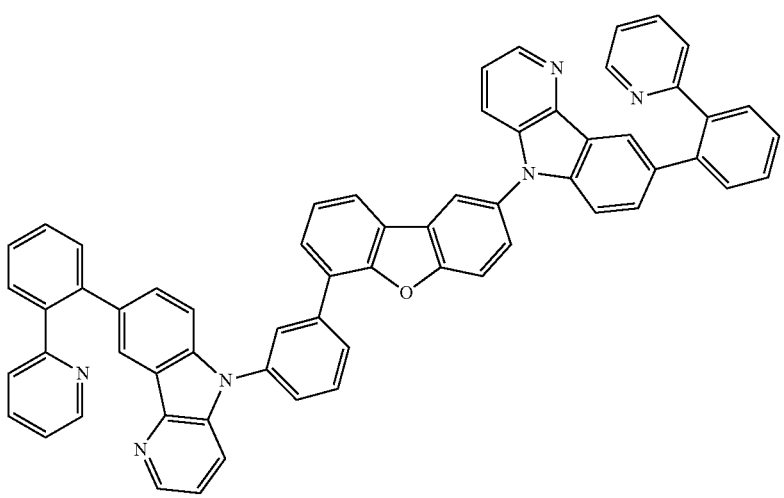

ET-24
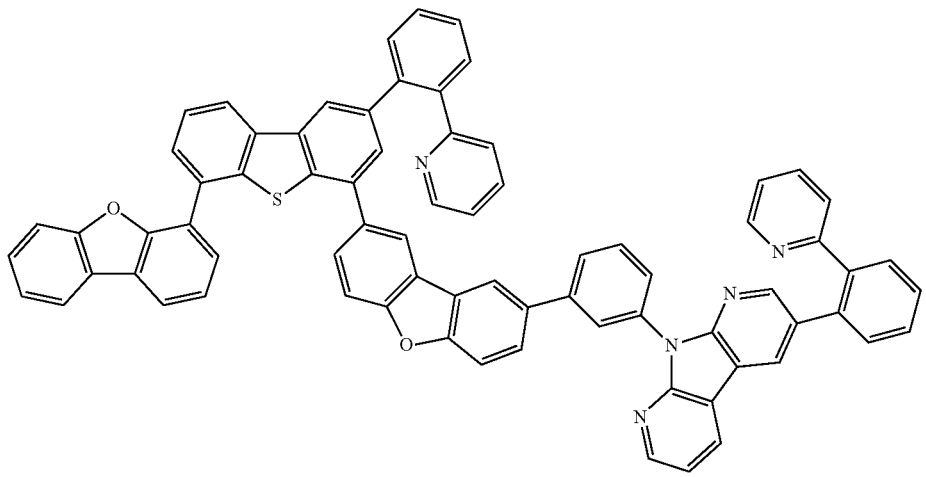
ET-25
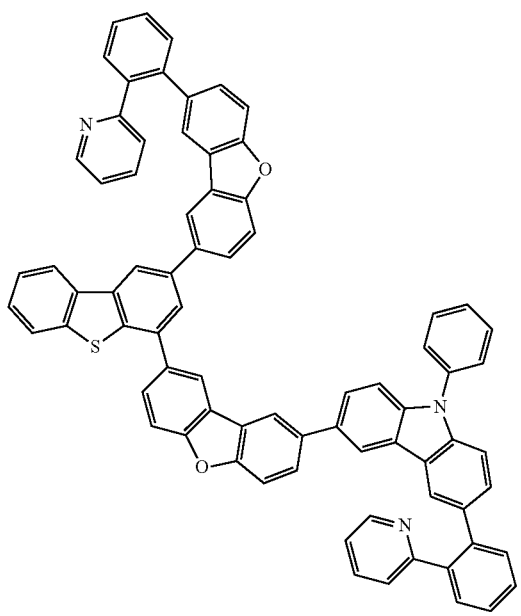
[Chemical Formula 53]
ET-26 ET-27
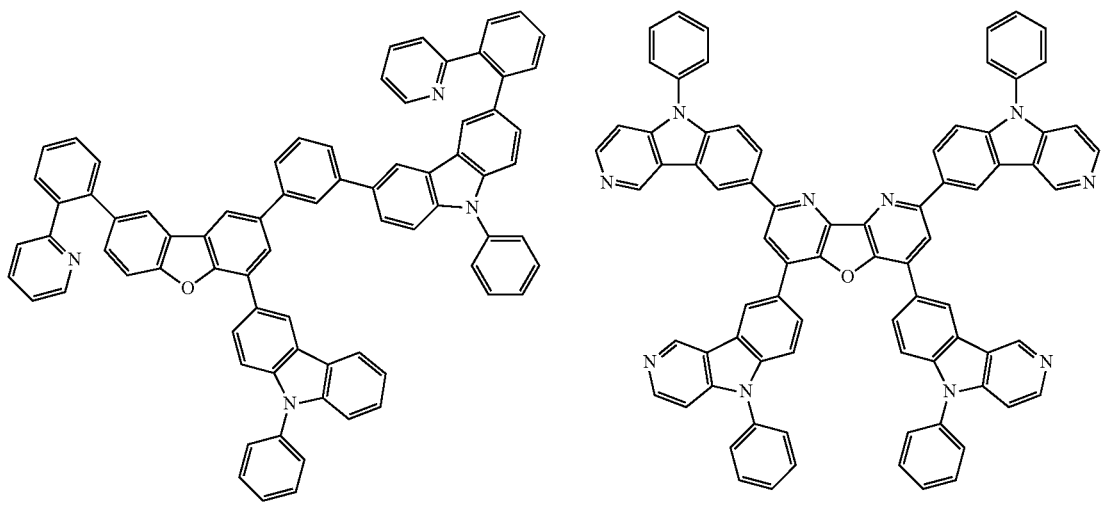

ET-28
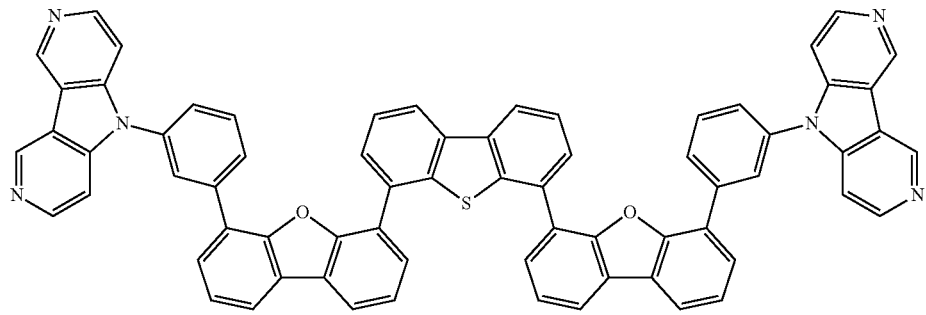
[Chemical Formula 54]
ET-29
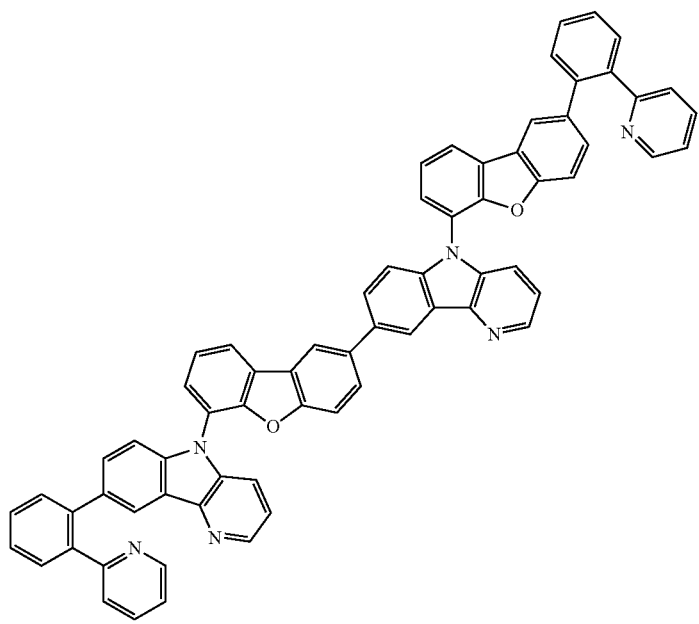
ET-30
ET-31
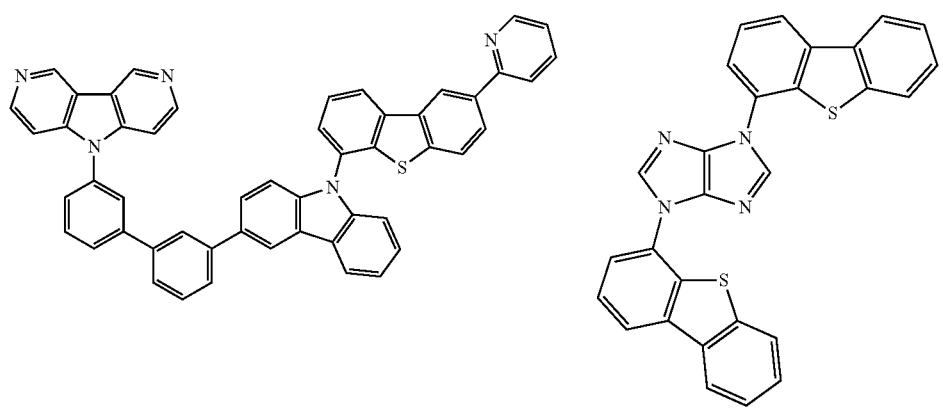

-continued
ET-32
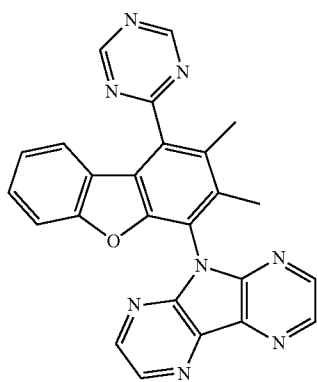
ET-33
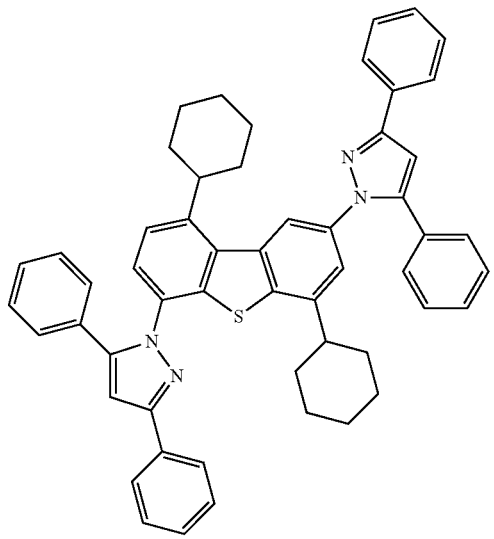
[Chemical Formula 55]
ET-34
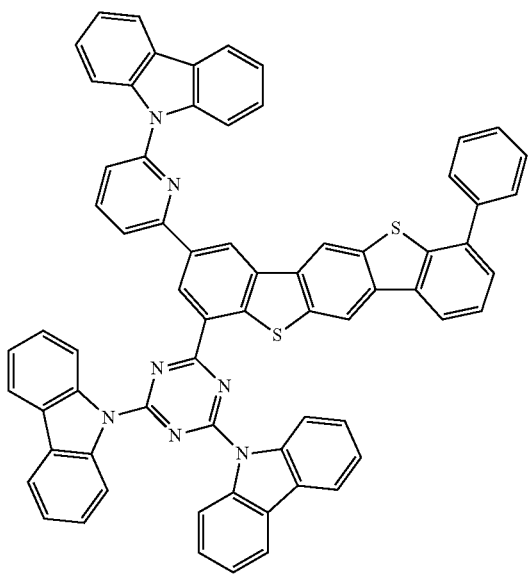
ET-35
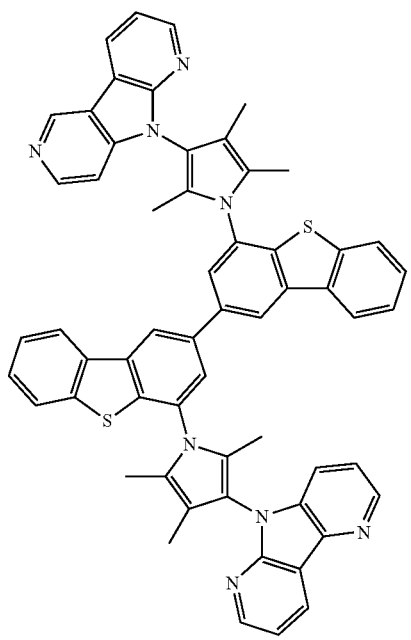
ET-36
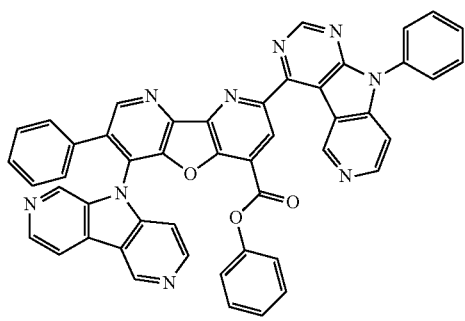
ET-37
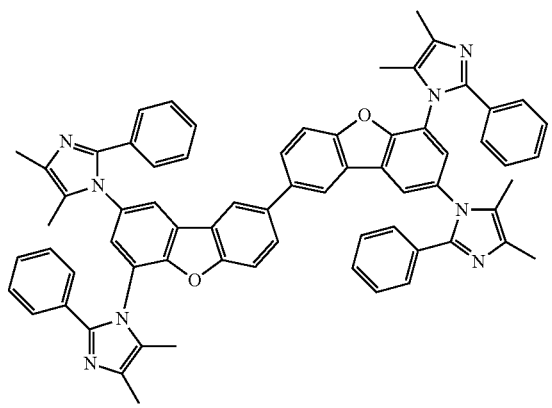

[Chemical Formula 56]
ET-38
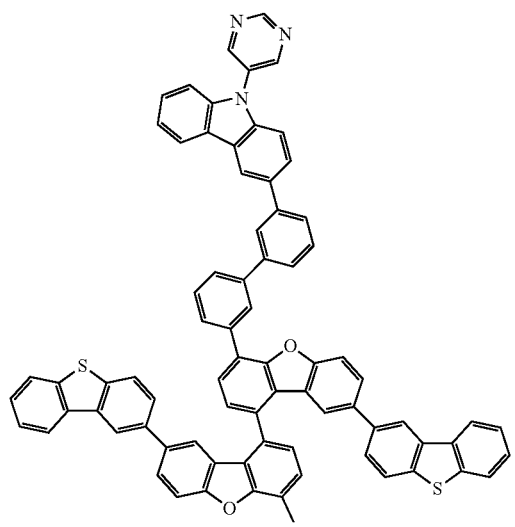
ET-39
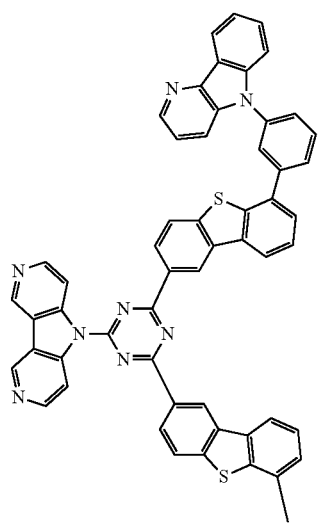
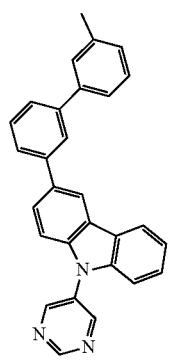
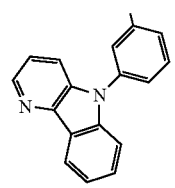
[Chemical Formula 57]
ET-40
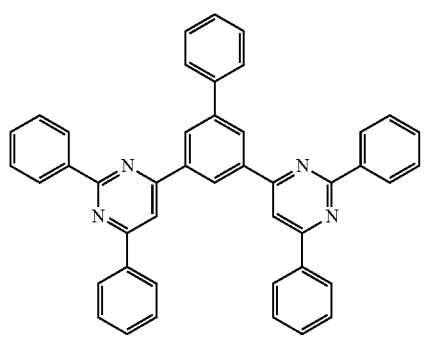
ET-41
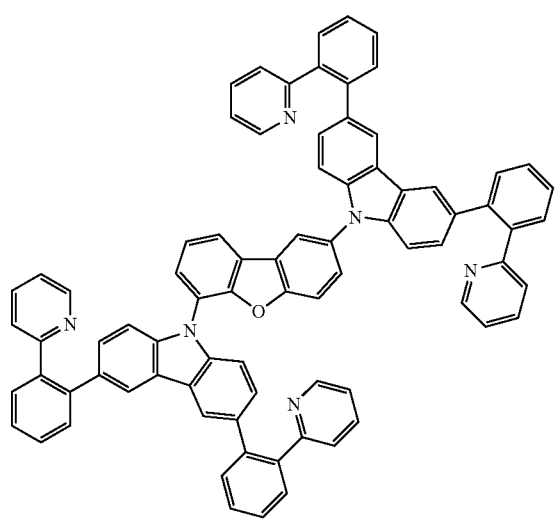

-continued

ET-42

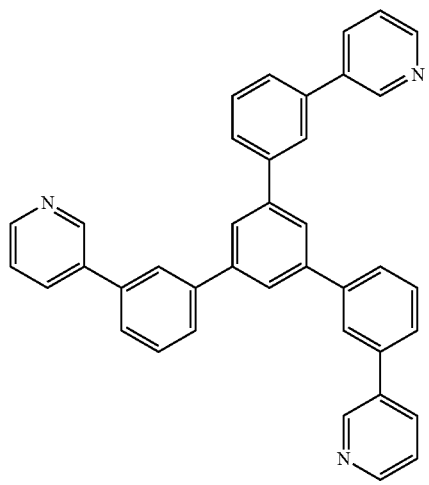

ET-43

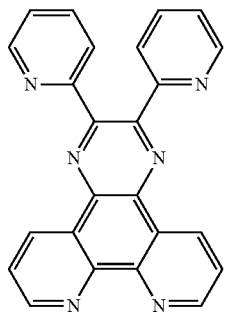

<Cathode>

On the other hand, an electrode to be used as the cathode is made of an electrode material such as a metal (referred to as electron-injecting metal), alloy, or electroconductive compound having a small work function (4 eV or less) or a mixture of two or more of them. Specific examples of such an electrode material include sodium, sodium-potassium alloys, magnesium, lithium, magnesium/copper mixtures, magnesium/silver mixtures, magnesium/aluminum mixtures, magnesium/indium mixtures, aluminum/aluminum oxide ($Al_2O_3$) mixtures, indium, lithium/aluminum mixtures, and rare-earth metals. Among them, from the viewpoint of electron injectability and durability against, for example, oxidation, preferred are mixtures of an electron-injecting metal and a second metal that is a stable metal having a larger work function than the electron-injecting metal, such as magnesium/silver mixtures, magnesium/aluminum mixtures, magnesium/indium mixtures, aluminum/aluminum oxide ($Al_2O_3$) mixtures, lithium/aluminum mixtures, and aluminum.

The cathode can be formed by forming a thin film of such an electrode material by a method such as vapor deposition or sputtering. Further, the cathode preferably has a sheet resistance of several hundred Ω/□ or less, and has a film thickness selected from a range of usually 10 nm to 5 μm, preferably 50 to 200 nm.

It is to be noted that either the anode or the cathode of the organic EL element may be transparent or translucent to transmit emitted light therethrough, which is advantageous in that luminance is increased.

Further, a transparent or translucent cathode can be formed by forming a 1 to 20 nm-thick film of the above metal and then forming thereon an electroconductive transparent material that will be described later with reference to the anode. This can be applied to produce an element whose anode and cathode are both optically transparent.

<Injection Layer: Electron Injection Layer (Cathode Buffer Layer), Hole Injection Layer>

The injection layer is optionally provided and includes an electron injection layer and a hole injection layer. As described above, the injection layer may be provided between the anode and the light-emitting layer or the hole transport layer and between the cathode and the light-emitting layer or the electron transport layer.

The injection layer refers to a layer provided between an electrode and an organic layer to reduce driving voltage or to increase luminance, and the details thereof are described in "The Front Line of Organic EL Elements and Industrialization Thereof (published on Nov. 30, 1998 by NTS Inc.)", Volume 2, Chapter 2 "Electrode Materials" (pp. 123 to 166). The injection layer includes a hole injection layer (anode buffer layer) and an electron injection layer (cathode buffer layer).

The details of the anode buffer layer (hole injection layer) are described also in, for example, JP 9-45479 A, JP 9-260062 A, and JP 8-288069 A. Specific examples of the anode buffer layer include: a phthalocyanine buffer layer typified by copper phthalocyanine; a hexaazatriphenylene derivative buffer layer such as one described in, for example, JP 2003-519432 W or JP 2006-135145 A; an oxide buffer layer typified by vanadium oxide; an amorphous carbon buffer layer; a polymer buffer layer using an electroconductive polymer such as polyaniline (emeraldine) or polythiophene; and an ortho-metalated complex layer typified by, for example, a tris(2-phenylpyridine) iridium complex.

The details of the cathode buffer layer (electron injection layer) are described also in, for example, JP 6-325871 A, JP 9-17574 A, and JP 10-74586. Specific examples of the cathode buffer layer include: a metal buffer layer typified by, for example, strontium or aluminum; an alkali metal compound buffer layer typified by lithium fluoride or potassium fluoride; an alkaline-earth metal compound buffer layer typified by magnesium fluoride or cesium fluoride; and an oxide buffer layer typified by aluminum oxide. The buffer layer (injection layer) is preferably a very thin film, and the film thickness thereof depends on the material thereof, but is preferably in the range of 0.1 nm to 5 μm.

<Blocking Layer: Hole Blocking Layer, Electron Blocking Layer>

The blocking layer is optionally provided in addition to the basic constituent layers of organic compound thin films as described above. As an example of the blocking layer, a hole blocking layer is described in, for example, JP 11-204258 A, JP 11-204359 A, and "The Front Line of Organic EL Elements and Industrialization Thereof (published on Nov. 30, 1998 by NTS Inc.), p. 237.

The hole blocking layer has, in a broad sense, a function as an electron transport layer, and is made of a hole blocking material that has the function of transporting electrons but has a very low ability to transport holes. That is, the hole blocking layer blocks holes while transporting electrons so that the probability of recombination of electrons and holes can be increased.

Further, the constituent described above as the electron transport layer can be used as the hole blocking layer, if necessary.

The hole blocking layer of the organic EL element according to the present invention is preferably provided adjacent to the light-emitting layer.

The hole blocking layer preferably contains a carbazole derivative, a carboline derivative, or a diazacarbazole derivative (here, the diazacarbazole derivative refers to a compound having a nitrogen atom substituting for any one of carbon atoms constituting a carboline ring) mentioned above as the host compound.

On the other hand, the electron blocking layer has, in a broad sense, a function as a hole transport layer, and is made of a material that has the function of transporting holes but has a very low ability to transport electrons. That is, the electron blocking layer blocks electrons while transporting holes so that the probability of recombination of electrons and holes can be increased.

Further, a constituent that will be described later as the hole transport layer can be used as the electron blocking layer, if necessary. The hole blocking layer or the electron transport layer used in the present invention preferably has a layer thickness of 3 to 100 nm, more preferably 5 to 30 nm.

<Hole Transport Layer>

The hole transport layer is made of a hole transport material having the function of transporting holes, and in a broad sense, a hole injection layer and an electron blocking layer are also included in the hole transport layer. The hole transport layer may be a single layer or two or more layers.

The hole transport material has either hole injectability or transportability or electron blockability, and may be either organic or inorganic. Examples of the hole transport material include triazole derivatives, oxadiazole derivatives, imidazole derivatives, polyarylalkane derivatives, pyrazoline derivatives and pyrazolone derivatives, phenylenediamine derivatives, arylamine derivatives, amino-substituted chalcone derivatives, oxazole derivatives, styrylanthracene derivatives, fluorenone derivatives, hydrazone derivatives, stilbene derivatives, silazane derivatives, aniline-based copolymers, and electroconductive polymers/oligomers, especially thiophene oligomers.

Further, azatriphenylene derivatives such as those described in, for example, JP 2003-519432 W and JP 2006-135145 A may also be used as the hole transport materials.

The hole transport material to be used may be any one of the above materials, but a porphyrin compound, an aromatic tertiary amine compound, and a styrylamine compound are preferably used, and an aromatic tertiary amine compound is particularly preferably used.

Typical examples of the aromatic tertiary compound and the styrylamine compound include: N,N,N',N'-tetraphenyl-4,4'-diaminophenyl; N,N'-diphenyl-N,N'-bis(3-methylphenyl)-[1,1'-biphenyl]-4,4'-diamine (TPD); 2,2-bis(4-di-p-tolylaminophenyl)propane; 1,1-bis(4-di-p-tolylaminophenyl)cyclohexane; N,N,N',N'-tetra-p-tolyl-4,4'-diaminobiphenyl; 1,1-bis(4-di-p-tolylaminophenyl)-4-phenylcyclohexane; bis(4-dimethylamino-2-methylphenyl)phenylmethane; bis(4-di-p-tolylaminophenyl)phenylmethane; N,N'-diphenyl-N,N'-di(4-methoxyphenyl)-4,4'-diaminobiphenyl; N,N,N',N'-tetraphenyl-4,4'-diaminodiphenyl ether; 4,4'-bis(diphenylamino) quardriphenyl; N,N,N-tri(p-tolyl)amine; 4-(di-p-tolylamino)-4'-[4-(di-p-tolylamino)styryl]stilbene; 4-N,N-diphenylamino-(2-diphenylvinyl)benzene; 3-methoxy-4'-N,N-diphenylaminostilbene; N-phenylcarbazole; a compound having two fused aromatic rings in its molecule described in U.S. Pat. No. 5,061,569, such as 4,4'-bis[N-(1-naphthyl)-N-phenylamino]biphenyl (NPD); and 4,4',4"-tris[N-(3-methylphenyl)-N-phenylamino]triphenylamine (MTDATA), in which three triphenylamine units are linked in a starburst form, described in JP 4-308688 A.

Further, polymer materials having these materials introduced into the polymer chains thereof or polymer materials having these materials as the main chains thereof may also be used.

Further, inorganic compounds such as p-type Si and p-type SiC can also be used as the hole injection materials or hole transport materials.

Further, so-called p-type hole transport materials such as those described in JP 11-251067 A and a literature written by J. Huang et. al. (Applied Physics Letters 80 (2002), p. 139) may also be used. In the present invention, these materials are preferably used because a light-emitting element having higher efficiency can be obtained.

The hole transport layer can be formed by forming a thin film of the hole transport material by a known method such as vacuum deposition, spin coating, casting, printing including ink jetting, or LB process.

The layer thickness of the hole transport layer is not particularly limited, but is usually about 5 nm to 5 μm, preferably 5 to 200 nm. The hole transport layer may have a single-layer structure made of one or two or more of the above-mentioned materials.

Further, the hole transport layer may be one doped with an impurity to have high p-type properties. Examples of such a hole transport layer include those described in, for example, JP 4-297076 A, JP 2000-196140 A, JP 2001-102175 A, and J. Appl. Phys., 95, 5773 (2004).

In the present invention, such a hole transport layer having good p-type properties is preferably used because a low-power-consumption element can be produced.

<Anode>

The anode used in the organic EL element is preferably made of an electrode material such as a metal, alloy, or electroconductive compound having a high work function (4 eV or more) or a mixture of two or more of them. Specific examples of such an electrode material include metals such as Au and electroconductive transparent materials such as CuI, indium tin oxide (ITO), $SnO_2$, and ZnO.

An amorphous material capable of forming a transparent electroconductive film such as IDIXO($In_2O_3$—ZnO) may also be used. The anode may be formed by forming a thin film of such an electrode material by a method such as vapor deposition or sputtering and then by subjecting the thin film to photolithography to form a desired pattern. Alternatively, when high pattern accuracy is not required (about 100 μm or more), patterning may be performed using a mask having a desired pattern when a thin film of the electrode material is formed by vapor deposition or sputtering.

Alternatively, a coatable material such as an organic electroconductive compound is used, a wet film-forming method such as printing or coating may also be used. When luminescence is extracted through this anode, the anode preferably has a transmittance of greater than 10% and a sheet resistance of several hundred Ω/□ or less. The film thickness of the anode depends on the type of material used, but is selected from a range of usually 10 to 1000 nm, preferably 10 to 200 nm.

<Supporting Substrate>

The type of a supporting substrate (hereinafter, also referred to as base, substrate, base material, or support) that can be used in the organic EL element according to the present invention is not particularly limited and may be, for example, glass or plastic, and the supporting substrate may be either transparent or opaque. When light is extracted from the supporting substrate side, the supporting substrate is preferably transparent. Preferred examples of the transparent supporting substrate include glass, quartz, and transparent resin films. The supporting substrate is particularly preferably a resin film capable of imparting flexibility to the organic EL element.

Examples of such a resin film include: polyesters such as polyethylene terephthalate (PET) and polyethylene naphthalate (PEN); polyethylene; polypropylene; cellophane; cellulose esters such as cellulose diacetate, cellulose triacetate (TAC), cellulose acetate butyrate, cellulose acetate propionate (CAP), cellulose acetate phthalate, and cellulose nitrate or derivatives thereof; polyvinylidene chloride; polyvinyl alcohol; polyethylenevinyl alcohol; syndioctatic polystyrene; polycarbonate; norbornene resins; polymethylpentene; polyether ketone; polyimide; polyether sulfone (PES); polyphenylene sulfide; polysulfones; polyetherimide; polyetherketoneimide; polyamide; fluorine resins; nylon; polymethyl methacrylate; acrylics or polyarylates; and cycloolefin-based resins such as ARTON (trade name, manufactured by JSR Corporation) and APEL (trade name, manufactured by Mitsui Chemicals, Inc.).

The surface of the resin film may be coated with an inorganic or organic film or a hybrid film of both inorganic and organic materials. The resin film is preferably a barrier film whose water vapor transmission rate (25±0.5° C., relative humidity: (90±2) % RH) as measured by a method in accordance with JIS K 7129-1992 is 0.01 g/m$^2$·24 h or less, more preferably a high barrier film whose oxygen transmission rate as measured by a method in accordance with JIS K 7126-1987 is $10^{-3}$ mL/m$^2$·24 h·atm or less and whose water vapor transmission rate is $10^{-5}$ g/m$^2$·24 h or less.

The barrier film may be made of any material having the function of inhibiting infiltration of a substance, such as moisture or oxygen, that deteriorates the element. As such a material, for example, silicon oxide, silicon dioxide, or silicon nitride can be used. Further, in order to improve the brittleness of the film, the film more preferably has a laminate structure including such an inorganic layer and a layer made of an organic material. The inorganic layer and the organic layer can be stacked in any order, but both the inorganic and organic layers are preferably stacked alternately two or more times.

A method for forming the barrier film is not particularly limited, and examples of the method include vacuum vapor deposition, sputtering, reactive sputtering, molecular beam epitaxy, cluster ion beam deposition, ion plating, plasma polymerization, atmospheric-pressure plasma polymerization, plasma CVD, laser CVD, thermal CVD, and coating. However, atmospheric-pressure plasma polymerization such as one described in JP 2004-68143 A is particularly preferred.

Examples of the opaque supporting substrate include: metal plates such as aluminum and stainless steel; films; opaque resin substrates; and ceramic substrates.

The light extraction efficiency of the organic EL element according to the present invention at room temperature is preferably 1% or more, more preferably 5% or more.

Extraction quantum efficiency (%)=number of photons emitted out from organic EL element/number of electrons passing through organic El element×100

Further, a hue improving filter such as a color filter may also be used, or a color conversion filter may also be used which uses fluorescent materials to convert the color of light emitted from the organic EL element to multiple colors. When such a color conversion filter is used, the λmax of light emitted from the organic EL element is preferably 480 nm or less.

<Method for Producing Organic EL Element>

An example of a method for producing the organic EL element will be described with reference to a case where the element has a structure of anode/hole injection layer/hole transport layer/light-emitting layer/hole blocking layer/electron transport layer/cathode buffer layer (electron injection layer)/cathode.

First, a thin film made of a desired electrode material, for example, an anode material is formed on an appropriate base to have a thickness of 1 μm or less, preferably 10 to 200 nm to form an anode.

Then, organic compound-containing thin films such as a hole injection layer, a hole transport layer, a light-emitting layer, a hole blocking layer, an electron transport layer, and a cathode buffer layer are formed as element materials on the anode.

The thin films can be formed by, for example, a vacuum vapor deposition method or a wet method (also referred to as wet process).

Examples of the wet method include spin coating, casting, die coating, blade coating, roll coating, ink jetting, printing, spray coating, curtain coating, and LB process. From the viewpoint that a thin film can be precisely formed and high productivity is achieved, a method having high adaptability to a roll-to-roll system is preferred, such as die coating, roll coating, ink jetting, or spray coating. Different film-forming methods may be applied to different layers.

Examples of a liquid medium for dissolving or dispersing an organic EL material, such as a luminescent dopant, used in the present invention include: organic solvents such as ketones such as methyl ethyl ketone and cyclohexanone, aliphatic acid esters such as ethyl acetate, halogenated hydrocarbons such as dichlorobenzene, aromatic hydrocarbons such as toluene, xylene, mesitylene, and cyclohexylbenzene, aliphatic hydrocarbons such as cyclohexane, decaline, and dodecane, dimethylformamide (DMF), and DMSO.

The organic EL material can be dispersed by a method such as ultrasonic dispersion, high shearing dispersion, or medium dispersion.

After these layers are formed, a thin film made of a cathode material is formed thereon to have a thickness in the range of 1 μm or less, preferably 50 to 200 nm to provide a cathode. In this way, a desired organic EL element can be obtained.

Alternatively, the organic EL element may be produced by reversing the order of the above processes so that a cathode, a cathode buffer layer, an electron transport layer, a hole blocking layer, a light-emitting layer, a hole transport layer, a hole injection layer, and an anode are formed in this order.

The organic EL element according to the present invention is preferably produced without stopping evacuation during formation of the layers from the hole injection layer to the cathode, but the organic EL element may be taken out on the way to perform another film-forming method. At this time, the operation is preferably performed in a dry inert gas atmosphere.

<Sealing>

An example of a sealing means used in the present invention includes bonding of a sealing member, the electrode, and the supporting substrate with an adhesive.

The sealing member may have either a recessed plate shape or a flat plate shape as long as the sealing member is provided so as to cover the display region of the organic EL element. It does not matter whether the sealing member is transparent or whether the sealing member is electrically insulating.

Specific examples of the sealing member include a glass plate, a polymer plate•film, and a metal plate•film. Examples of the glass plate include soda-lime glass, barium•strontium-containing glass, lead glass, aluminosilicate glass, borosilicate glass, barium borosilicate glass, and quartz.

Examples of the polymer plate include plates made of, for example, polycarbonate, acrylic, polyethylene terephthalate, polyether sulfide, and polysulfone.

Examples of the metal plate include plates made of at least one metal selected from the group consisting of stainless steel, iron, copper, aluminum, magnesium, nickel, zinc, chromium, titanium, molybdenum, silicon, germanium, and tantalum or an alloy thereof.

In the present invention, from the viewpoint of reducing the thickness of the element, a polymer film or a metal film can be preferably used.

Further, the polymer film preferably has an oxygen transmission rate of $1 \times 10^{-3}$ mL/m$^2 \cdot$24 h·atm or less as measured by a method in accordance with JIS K 7126-1987 and a water vapor transmission rate (25±0.5° C., relative humidity: (90±2)% RH) of $1 \times 10^{-3}$ g/m$^2 \cdot$24 h or less as measured by a method in accordance with JIS K 7129-1992.

When the sealing member is processed to form a recess, for example, sand blasting or chemical etching is employed.

Specific examples of the adhesive include: photo-curable or heat-curable adhesives having a reactive vinyl group such as an acrylic oligomer or a methacrylic oligomer; and moisture-curable adhesives such as 2-cyanoacrylate. Other examples of the adhesive include heat- or chemically-curable (two-component type) adhesives such as epoxy-based adhesives. Other examples of the adhesive include hot melt-type polyamides, polyesters, and polyolefins. Other examples of the adhesive include cation curable-type UV-curable epoxy resin adhesives.

It is to be noted that there is a case where the organic EL element is deteriorated by heat treatment, and therefore the adhesive is preferably curable at a temperature in the range of room temperature to 80° C. Further, the adhesive may contain a drying agent dispersed therein. Application of the adhesive to a sealing area may be performed by a commercially-available dispenser or by printing such as screen printing.

It is also preferred that an inorganic or organic layer may be formed as a sealing film on the outer side of the electrode located on the opposite side of the organic layer(s) from the supporting substrate so that the inorganic or organic layer covers the electrode and the organic layer and is in contact with the supporting substrate. In this case, the film may be made of any material having the function of inhibiting infiltration of a substance, such as moisture or oxygen, that deteriorates the element. As such a material, for example, silicon oxide, silicon dioxide, or silicon nitride can be used.

Further, in order to improve the brittleness of the film, the film preferably has a laminate structure including such an inorganic material layer and a layer made of an organic material. A method for forming these films is not particularly limited, and examples thereof include vacuum deposition, sputtering, reactive sputtering, molecular beam epitaxy, cluster ion beam deposition, ion plating, plasma polymerization, atmospheric plasma polymerization, plasma CVD, laser CVD, thermal CVD, and coating.

A space between the sealing member and the display region of the organic EL element is preferably filled with an a vapor phase such as an inert gas, e.g., nitrogen or argon or a liquid phase such as an inert liquid, e.g., fluorohydrocarbon or silicone oil. Alternatively, the space may be a vacuum. Further, a hygroscopic compound may be enclosed in the interior of the sealing member.

Examples of the hygroscopic compound include: metal oxides (e.g., sodium oxide, potassium oxide, calcium oxide, barium oxide, magnesium oxide, aluminum oxide); sulfates (e.g., sodium sulfate, calcium sulfate, magnesium sulfate, cobalt sulfate); metal halides (e.g., calcium chloride, magnesium chloride, cesium fluoride, tantalum fluoride, cerium bromide, magnesium bromide, barium iodide, magnesium iodide); perchlorates (e.g., barium perchlorate, magnesium perchlorate). Among them, sulfates, metal halides, and perchlorates are preferably used in the form of anhydrous salt.

<Protective Film, Protective Plate>

A protective film or a protective plate may be provided on the outer side of the sealing film or the film for sealing on the opposite side of the organic layer (s) from the supporting substrate to increase the mechanical strength of the element. Particularly, when sealing is performed using the sealing film, the mechanical strength thereof is not necessarily high, and therefore such a protective film or protective plate is preferably provided. Examples of a material that can be used for the protective film or protective plate include the same glass plate, polymer plate•film, and metal plate•film as those used for sealing described above. However, from the viewpoint of reducing weight and thickness, a polymer film is preferably used.

<Light Extraction>

It is generally said that an organic EL element emits light inside a layer having a higher refractive index (about 1.7 to 2.1) than air, and only about 15% to 20% of light generated in a light-emitting layer can be extracted. This is because light entering an interface (interface between a transparent substrate and air) at an angle θ equal to or larger than the critical angle is totally reflected and therefore cannot be extracted out of the element, or light is totally reflected at the interface between a transparent electrode or the light-emitting layer and the transparent substrate and guided through the transparent electrode or the light-emitting layer, and as a result, escapes in a direction toward the side face of the element.

Examples of a technique for increasing such light extraction efficiency include a method in which a transparent substrate is formed to have surface irregularities to prevent total reflection at the interface between the transparent substrate and air (U.S. Pat. No. 4,774,435), a method in which light-harvesting properties are imparted to a substrate to increase efficiency (JP 63-314795 A), a method in which reflective surfaces are formed on, for example, the side surfaces of an element (JP 1-220394 A), a method in which a flat layer having an intermediate refractive index is introduced between a substrate and a light emitter to form an antireflective film (JP 62-172691 A), a method in which a flat layer having a lower refractive index than a substrate is introduced between a substrate and a light emitter (JP 2001-202827 A), and a method in which a diffraction grating is formed between any layers selected from a substrate, a transparent electrode layer, and a light-emitting layer (the interface between a substrate and an external space is also included) (JP 11-283751 A).

In the present invention, these methods can be used in combination with the organic EL element according to the present invention, but the method in which a flat layer having a lower refractive index than a substrate is introduced between a substrate and a light emitter or the method in which a diffraction grating is formed between any layers selected from a substrate, a transparent electrode layer, and a light-emitting layer (the interface between a substrate and an external space is included) can be preferably used.

In the present invention, an element having higher luminance or higher durability can be obtained by combining these techniques.

When a medium having a low refractive index is formed between a transparent electrode and a transparent substrate so as to have a thickness larger than the wavelength of light, the lower the refractive index of the medium is, the higher the extraction efficiency of light from the transparent electrode is.

Examples of the low-refractive index layer include aerogel, porous silica, magnesium fluoride, and fluorine-based polymers. The refractive index of the transparent substrate is generally about 1.5 to 1.7, and therefore the refractive index of the low-refractive index layer is preferably about 1.5 or less, more preferably 1.35 or less.

Further, the thickness of the low-refractive index medium is preferably twice or more the wavelength of light in the medium. This is because if the low-refractive index medium has a thickness comparable to the wavelength of light, electromagnetic waves exuding as evanescent waves penetrate into the substrate so that the effect of the low-refractive index layer is reduced.

The method in which a diffraction grating is introduced at an interface that causes total reflection or in any of media is effective at increasing light extraction efficiency. This method utilizes the property of a diffraction grating that it can change the direction of light to a specific direction different from the direction of refraction by so-called Bragg diffraction such as primary diffraction or secondary diffraction, and is directed to extract light that is generated in a light-emitting layer but cannot come outside due to, for example, total reflection at the interface between layers by introducing a diffraction grating between any layers or in a medium (in a transparent substrate or in a transparent electrode) to diffract light.

The diffraction grating to be introduced preferably has a two-dimensional periodic refraction index. This is because light generated in a light-emitting layer is emitted randomly in all directions, and therefore a general one-dimensional diffraction grating having a periodic refraction index distribution only in a specific direction can diffract only light traveling in a specific direction and therefore cannot greatly increase light extraction efficiency.

However, a diffraction grating having a two-dimensional refractive index distribution can diffract light traveling in all directions and therefore can increase light extraction efficiency.

As described above, the diffraction grating may be introduced between any layers or in any medium (in a transparent substrate or in a transparent electrode). However, the diffraction grating is preferably introduced in the vicinity of an organic light-emitting layer where light is generated.

At this time, the period of the diffraction grating is preferably about ½ to 3 times the wavelength of light in the medium.

The pattern of the diffraction grating is preferably a two-dimensional repetitive pattern, such as a square lattice pattern, a triangular lattice pattern, or a honeycomb lattice pattern.

<Light-Condensing Sheet>

The organic EL element according to the present invention can increase its luminance in a specific direction by providing, for example, a micro-lens array structure on the light extraction side of the substrate or by combining the element with a so-called light-condensing sheet so that light is condensed in a specific direction, for example, in a direction toward the front side of the light-emitting surface of the element.

The micro-lens array is provided by, for example, two-dimensionally arranging, on the light extraction side of the substrate, square pyramids each having a side length of 30 μm and an apical angle of 90 degrees. The side length is preferably 10 to 100 μm. If the side length is less than the lower limit, coloration occurs due to the effect of diffraction, and if the side length is too large, the thickness of the element is undesirably increased.

As the light condensing sheet, for example, one practically used in LED backlights for liquid crystal display devices can be used. An example of such a sheet includes a brightness enhancing film (BEF) manufactured by Sumitomo 3M Ltd.

The prism sheet may have a structure in which, for example, Δ-shaped stripes having an apical angle of 90 degrees are formed with a pitch of 50 μm in a base material. The stripes may have a rounded apex, or may be provided with a pitch randomly changed, or may have another shape.

Further, in order to control the emission angle of light from the light-emitting element, the light-condensing sheet may be used in combination with a light diffuser plate•film. For example, a light diffusion film (LIGHT-UP) manufactured by KIMOTO Co., Ltd. can be used.

<Applications>

The organic EL element according to the present invention can be used as an electronic device, a display device, a display, or any type of light-emitting device. Examples of the light-emitting device include, but are not limited to, lighting devices (home lighting, car lighting), backlights for watches or liquid crystal displays, billboards, traffic lights, light sources for optical storage media, light sources for electrophotographic copiers, light sources for optical communication processors, and light sources for optical sensors. The organic EL element according to the present invention can be particularly effectively used as a backlight for liquid crystal display devices or a light source for lighting.

In production of the organic EL element according to the present invention, patterning may be performed by, for example, using a metal mask or ink-jet printing during film formation, if necessary. When patterning is performed, only the electrodes may be patterned, the electrodes and the light-emitting layer may be patterned, or all the layers of the element may be patterned. The element can be produced using a conventionally-known method.

Figure 7:
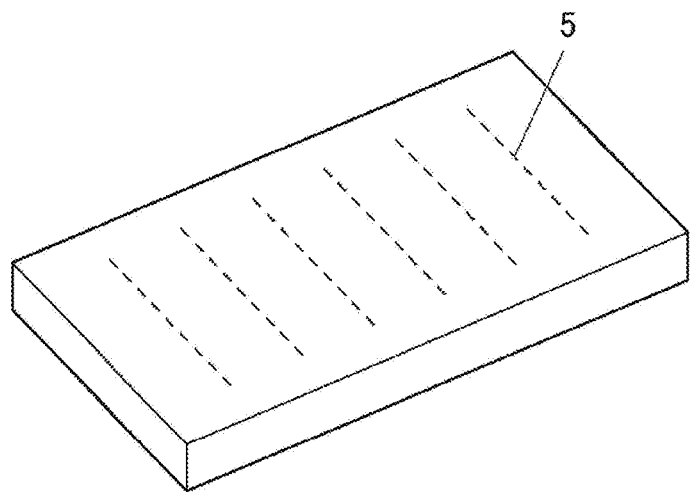
FIG. 7 is a schematic diagram of a full-color passive matrix-type display device.
Figure 7:
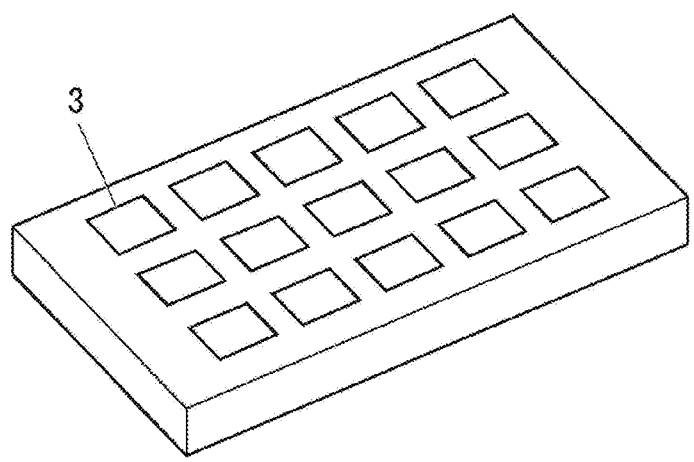
Figure 7:
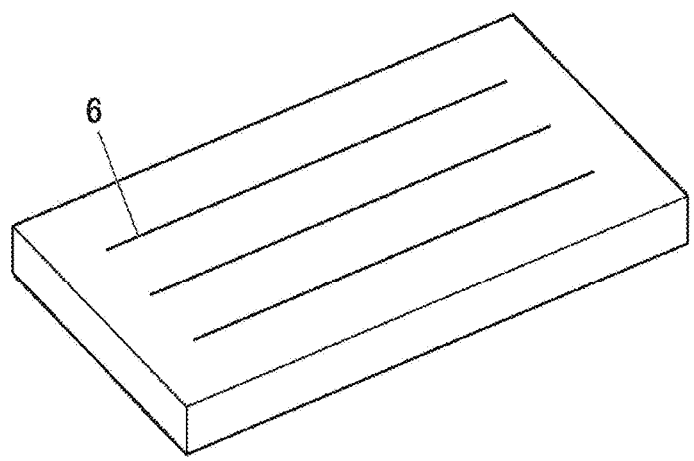

The color of light emitted from the organic EL element according to the present invention or from the compound according to the present invention is determined by applying a result measured by a spectroradiometer CS-1000 (manufactured by KONICA MINOLTA, Inc.) to the CIE chromaticity coordinate shown in FIG. 7. 16 in page 108 in "New Version of Handbook of Color Science" (The Color Science Association of Japan, University of Tokyo Press, 1985).

Further, when the organic EL element according to the present invention is a white element, white means that when the front luminance of light at a viewing angle of 2 degrees is measured by the above method, the chromaticity of the light is within a region of X=0.33±0.07 and Y=0.33±0.1 in the CIE 1931 color system at 1000 cd/m$^2$.

<Display Device>

A display device according to the present invention will be described. The display device according to the present invention includes the organic EL element according to the present invention. The display device according to the present invention may be either monochromatic or multichromatic, but will be described here with reference to a case where it is a multichromatic display device.

In the case of a multichromatic display device, a shadow mask is provided only when the light-emitting layer is formed, and films can be formed on the entire surface by vapor deposition, casting, spin coating, ink jetting, printing, or the like.

When only the light-emitting layer is patterned, patterning can be performed by any method, but is preferably performed by vapor deposition, ink jetting, spin coating, or printing.

The structure of the organic EL element provided in the display device is appropriately selected from the above structural examples of the organic EL element.

Further, the organic EL element is produced by the method described above as one aspect of production of the organic EL element according to the present invention.

When a direct voltage is applied to the thus obtained multichromatic display device, light emission can be observed through the application of a voltage of about 2 to 40 V by setting the polarity of the anode to + and the polarity of the cathode to −. Further, even when a voltage is applied in reverse polarity, no electric current flows and light is not emitted at all. When an alternating voltage is applied, light is emitted only when the polarity of the anode is + and the polarity of the cathode is −. It is to be noted that the alternating voltage applied may have any waveform.

The multichromatic display device can be used as a display device, a display, or any type of light emission source. The display device or the display can achieve full-color display by using three kinds of organic EL elements that emit blue light, red light, and green light.

Examples of the display device and the display include TV sets, personal computers, mobile devices, AV devices, teletext displays, and in-vehicle information displays. Particularly, the display device and the display may be used as display devices for reproducing still images or moving images. When the display device and the display are used as display devices for reproducing moving images, the driving system thereof may be either a simple matrix (passive matrix) system or an active matrix system.

Examples of the light source include home lighting, in-vehicle lighting, backlights for watches or liquid crystal displays, billboards, traffic lights, light sources for optical recording media, light sources for electrophotographic copiers, light sources for optical communication processors, and light sources for optical sensors. However, the present invention is not limited thereto.

Hereinbelow, an example of the display device having the organic EL element according to the present invention will be described based on a drawing.

Figure 4:
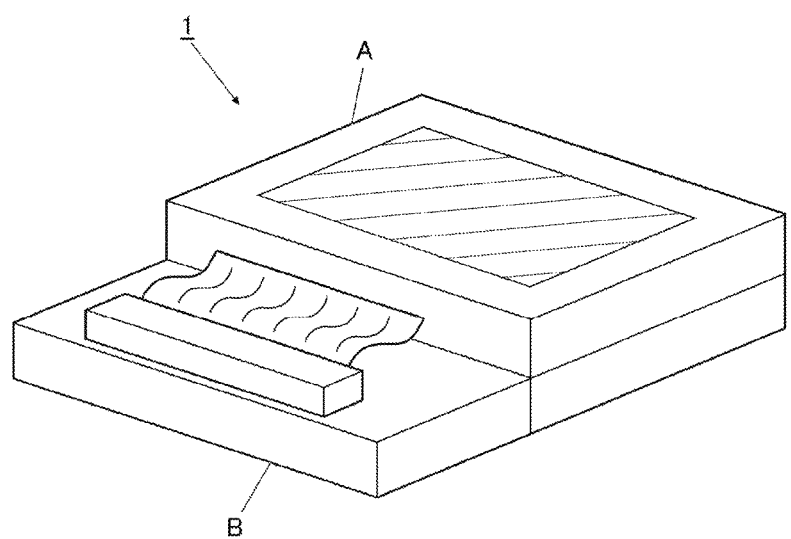
FIG. 4 is a schematic diagram of one example of a display device including an organic EL element.

FIG. 4 is a schematic diagram of one example of a display device including an organic EL element. More specifically, FIG. 4 is a schematic diagram of a display for, for example, a mobile phone that displays image information by means of light emission from an organic EL element.

A display 1 includes a display unit A having a plurality of pixels and a control unit B that performs image scanning of the display unit A based on image information.

The control unit B is electrically connected to the display unit A and sends a scan signal and an image data signal to each of the pixels based on external image information. The pixels of each scan line receive a scan signal and sequentially emit light based on an image data signal so that image information is displayed on the display unit A by image scanning.

Figure 5:
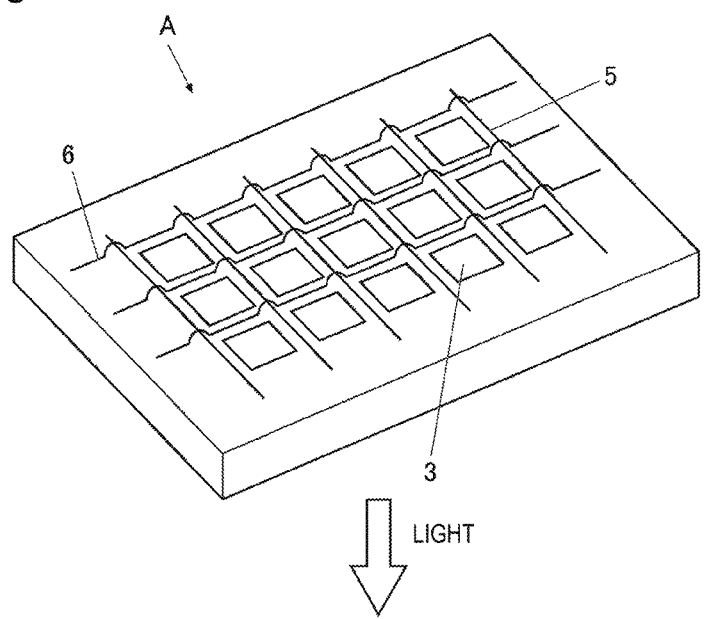
FIG. 5 is a schematic diagram of a display unit A.

FIG. 5 is a schematic diagram of the display unit A.

The display unit A has a wiring part including a plurality of scan lines 5 and data lines 6, a plurality of pixels 3, etc. on a substrate. Primary members of the display unit A will be described below.

FIG. 5 shows a case where light emitted from the pixels 3 is extracted in a direction indicated by a white arrow (downward direction).

The scan lines 5 and data lines 6 of the wiring part are each made of a electroconductive material. The scan lines 5 and the data lines 6 are perpendicular to each other to form a grid pattern, and are connected to the pixels 3 at their intersections (details are not shown in FIG. 5).

When a scan signal is applied from the scan line 5, the pixels 3 receive an image data signal from the data lines 6 and emit light based on the received image data.

Full-color display can be achieved by appropriately arranging pixels that emit light in a red region, pixels that emit light in a green region, and pixels that emit light in a blue region on the same substrate.

Figure 6:
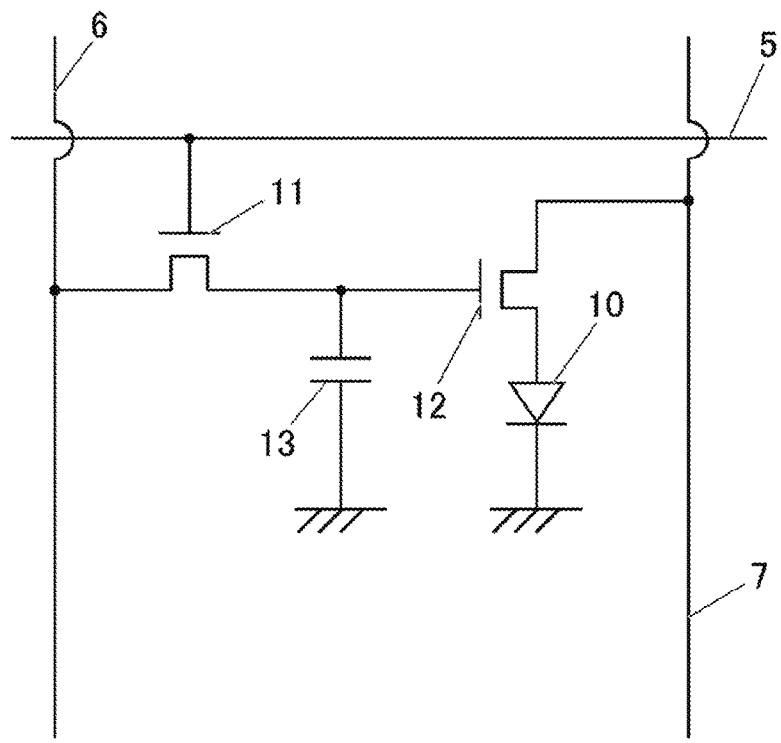
FIG. 6 is a circuit diagram of a pixel.

Next, the light emission process of the pixel will be described. FIG. 6 is a circuit diagram of the pixel.

The pixel includes an organic EL element 10, a switching transistor 11, a driving transistor 12, a capacitor 13, etc. Full-color display can be achieved by using organic EL elements that emit red light, green light, and blue light as the organic EL elements 10 in the pixels and arranging them on the same substrate.

In FIG. 6, an image data signal is applied to the drain of the switching transistor 11 through the data line 6 from the control unit B. Then, when a scan signal is applied to the gate of the switching transistor 11 through the scan line 5 from the control unit B, the switching transistor 11 is turned on, and the image data signal applied to the drain is transmitted to the capacitor 13 and the gate of the driving transistor 12.

As a result of the transmission of the image data signal, the capacitor 13 is charged according to the electric potential of the image data signal and the driving transistor 12 is turned on. The drain of the driving transistor 12 is connected to a power supply line 7, and the source of the driving transistor 12 is connected to the electrode of the organic EL element 10 to supply electric current to the organic EL element 10 from the power supply line 7 according to the electric potential of the image data signal applied to the gate.

When the scan signal is transferred to the next scan line 5 by the progressive scanning of the control unit B, the switching transistor 11 is turned off. However, even when the switching transistor 11 is turned off, the capacitor 13 keeps the charged electric potential of the image data signal, and therefore the driving transistor 12 is kept turned on and the organic EL element 10 continues to emit light until the next scan signal is applied. When the next scan signal is applied by progressive scanning, the driving transistor 12 is driven according to the electric potential of the next image data signal synchronized with the scan signal so that the organic EL element 10 emits light.

That is, light emission from the organic EL element 10 of each of the pixels 3 is achieved by providing the switching transistor 11 and the driving transistor 12 as active elements for the organic EL element 10 of each of the pixels 3. Such a light emission process is called active matrix system.

Here, light emitted from the organic EL element 10 may be multi-level light achieved by a multivalued image data signal having a multi-level electric potential or may be light of predetermined intensity turned on or off based on a binary image data signal. Further, the electric potential of the capacitor 13 may be kept until the next scan signal is applied, or may be discharged just before the next scan signal is applied.

The present invention is not limited to the above active matrix system, and light emission may be driven by a passive matrix system in which the organic EL elements emit light based on a data signal only when a scan signal is scanned.

FIG. 7 is a schematic diagram of a passive matrix-type display device. In FIG. 7, a plurality of scan lines 5 and a plurality of image data lines 6 are provided in a grid pattern so that pixels 3 are interposed between the opposed scan lines 5 and between the opposed image data lines 6.

When a scan signal is applied to the scan line 5 by progressive scanning, the pixels 3 connected to the scan line 5 emit light based on an image data signal.

Such a passive matrix system has no active elements in the pixels 3, which results in a reduction in production cost.

<Lighting Device>

A lighting device according to the present invention will be described. The lighting device according to the present invention has the above organic EL element.

The organic EL element according to the present invention may be applied to an organic EL element having a resonator structure. Example of the intended use of such an organic EL element having a resonator structure include, but not limited to, light sources for optical recording media, light sources for electrophotographic copiers, light sources for optical transmission processors, and light sources for optical sensors. Alternatively, the organic EL element may be used for the above applications by laser oscillation.

Further, the organic EL element according to the present invention may be used as a kind of lamp such as a light source for lighting or an exposing source, or may be used as a projection device of a type that projects images or a display device (display) of a type that directly visualizes still images or moving images.

The driving system of the display device for reproducing moving images may be either a simple matrix (passive matrix) system or an active matrix system. Further, a full-color display device can be produced by using two or more kinds of the organic EL elements according to the present invention different in emission color.

Further, the iridium complex according to the present invention can be applied to an organic EL element used as a lighting device that emits substantially white light. White light is obtained by mixing light of different emission colors simultaneously emitted from two or more luminescent materials. A combination of two or more emission colors may be a combination containing three maximum emission wavelengths of three primary colors of red, green, and blue or a combination containing two maximum emission wavelengths utilizing a relationship between complementary colors such as blue and yellow or blue green and orange.

Further, a combination of luminescent materials for obtaining two or more emission colors may be either a combination of two or more materials that emit phosphorescence or fluorescence or a combination of a luminescent material that emits fluorescence or phosphorescence and a dye material that emits light using light from the luminescent material as excitation light.

A mask is provided only when the light-emitting layer, the hole transport layer, or the electron transport layer is formed, and these layers can be formed simply by selectively forming a film using the mask. Other layers are common, and therefore patterning using a mask or the like is unnecessary. For example, an electrode film can be formed on the entire surface by vapor deposition, casting, spin coating, ink jetting, or printing, which improves productivity.

When an element is produced by this method, unlike a white organic EL device in which light-emitting elements of different colors are arranged in parallel in an array, the element itself emits white light.

The luminescent material used for the light-emitting layer is not particularly limited. For example, in the case of a backlight for liquid crystal display elements, white light may be obtained by combining any materials selected from the metal complexes according to the present invention and known luminescent materials so as to satisfy a wavelength range corresponding to CF (color filter) characteristics.

<One Aspect of Lighting Device of Present Invention>

One aspect of the lighting device according to the present invention including the organic EL element according to the present invention will be described.

A lighting device such as one shown in FIG. 8 or 9 can be formed by covering the non-light emitting surface of the organic EL element according to the present invention with a glass case in the following manner. A glass substrate having a thickness of 300 µm is used as a sealing substrate. An epoxy-based photo-curable adhesive (LC0629B LUX-TRAK manufactured by TOA GOSEI Co., Ltd.) is applied as a sealing material to the periphery of the glass case, and the glass case is placed over the cathode and adhered to the transparent supporting substrate. Then, the adhesive is cured by irradiation with UV light from the glass substrate side to seal the organic EL element.

Figure 8:
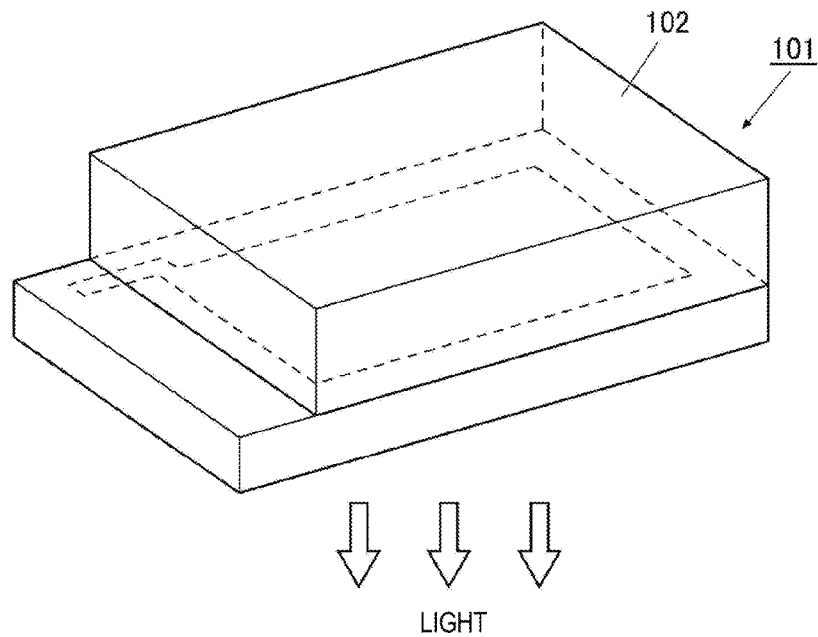
FIG. 8 is a schematic diagram of a lighting device.

FIG. 8 is a schematic diagram of a lighting device. The organic EL element according to the present invention (organic EL element 101 in the lighting device) is covered with a glass cover 102 (it is to be noted that sealing with the glass cover was performed in a glove box filled with a nitrogen atmosphere without exposing the organic EL element 101 to air (in an atmosphere of high-purity nitrogen gas with a purity of 99.999% or more).

Figure 9:
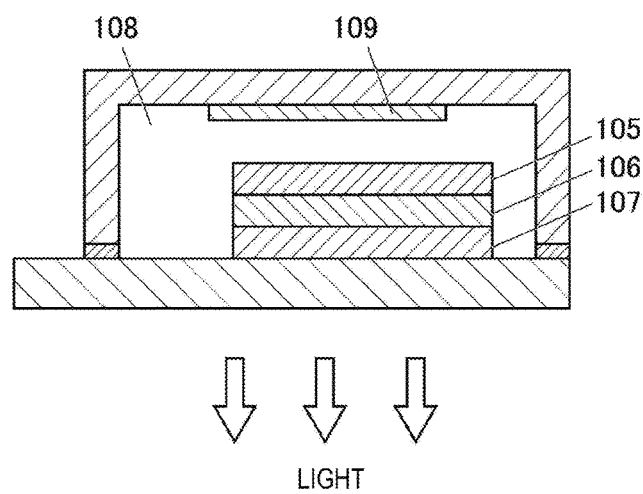
FIG. 9 is a schematic diagram of a lighting device.

FIG. 9 is a cross-sectional diagram of the lighting device, wherein reference numerals 105, 106, and 107 represent a cathode, an organic EL layer, and a glass substrate with transparent electrode. It is to be noted that the interior of the glass cover 102 is filled with nitrogen gas 108 and provided with a moisture capturing agent 109.

EXAMPLES

Hereinbelow, the present invention will be described in detail with reference to examples, but the present invention is not limited thereto.

Example 1

<Production of Thin Film 1-1>

On a quartz substrate of 100 mm×100 mm×1.1 mm, a thin film having a thickness of 30 nm was formed in the atmosphere by spin coating using a butyl acetate solution of a host compound 1 and (A)-R1 as a dopant compound.

<Production of Thin Films 1-2 to 1-11>

Thin films 1-2 to 1-11 were each produced in the same manner as in the production of the thin film 1-1 except that the host compound and the dopant compound were changed to compounds shown in Table 5.

TABLE 5

| Organic EL Element No. | Dopant Compound | Host Compound | PL Quantum Efficiency (Relative Value) | Note |
|---|---|---|---|---|
| 1-1 | (A)-R1 | 1 | 69 | Comparative Example |
| 1-2 | (A)-R3 | 1 | 628 | Present Invention |
| 1-3 | (B)-R2 | 1 | 66 | Comparative Example |
| 1-4 | (B)-R4 | 1 | 604 | Present Invention |
| 1-5 | (C)-R6 | 1 | 100 | Comparative Example |
| 1-6 | (C)-R11 | 1 | 794 | Present Invention |
| 1-7 | (D)-R1 | 1 | 67 | Comparative Example |
| 1-8 | (D)-R8 | 1 | 697 | Present Invention |
| 1-9 | (E)-R2 | 1 | 61 | Comparative Example |
| 1-10 | (F)-R1 | 1 | 90 | Comparative Example |
| 1-11 | (F)-R3 | 1 | 652 | Present Invention |

<Evaluation of Thin Films 1-1 to 1-11>

The PL (Photo Luminescence) quantum efficiency (%) of the iridium complex (dopant compound) was calculated based on the following method.

[Calculation of Quantum Efficiency (PLQE)]

An emission spectrum was measured at an excitation wavelength of 320 nm using a spectrofluorophotometer F-4500 (Hitachi High-Technologies Corporation), and the emission area thereof was determined. Further, an absorption spectrum was measured using a spectrophotometer U-3300 (Hitachi High-Technologies Corporation) to determine an absorbance at 320 nm.

Further, the value of emission area/absorbance (320 nm) of each of the thin films 1-1 to 1-11 was determined as PL quantum efficiency (relative value) by regarding the value of emission area/absorbance (320 nm) of the thin film 1-5 as 100.

As can be seen from Table 5, the thin films using the iridium complex according to the present invention had higher PL quantum efficiency than the thin films of comparative examples.

Example 2

<Production of Organic EL Element 2-1>

A substrate (NA45 manufactured by NH Techno Glass Corporation) obtained by forming an ITO (Indium Tin Oxide) film having a thickness of 100 nm as an anode on a glass substrate of 100 mm×100 mm×1.1 mm was subjected to patterning, and then the transparent support substrate provided with the ITO transparent electrode was ultrasonically washed with isopropyl alcohol, dried with dry nitrogen gas, and subjected to UV ozone cleaning for 5 minutes.

On the transparent support substrate, a thin film was formed by spin coating under conditions of 3000 rpm and 30 seconds using a solution obtained by diluting poly(3,4-ethylenedioxythiophene)-polystyrenesulfonate (PEDOT/PSS manufactured by Bayer, Baytron P Al 4083) with pure water to 70%, and was then dried at 200° C. for 1 hour to provide a first hole transport layer having a thickness of 20 nm.

This transparent support substrate was fixed to a substrate holder of a commercially-available vacuum deposition apparatus. On the other hand, a molybdenum resistance heating boat containing 200 mg of α-NPD (4,4'-bis[N-(1-naphthyl)-N-phenylamino]biphenyl), another molybdenum resistance heating boat containing 200 mg of a host compound OC-3, another molybdenum resistance heating boat containing 200 mg of a dopant compound (A)-R2, and another molybdenum resistance heating boat containing 200 mg of BCP were attached to the vacuum deposition apparatus.

Then, the pressure in a vacuum chamber was reduced to $4 \times 10^{-4}$ Pa, and then the heating boat containing α-NPD was heated by the passage of electric current to perform vapor deposition at a deposition rate of 0.1 nm/sec to provide a 30 nm-thick hole transport layer on the first hole transport layer.

Further, the heating boat containing the host compound OC-3 and the heating boat containing (A)-R2 were heated by the passage of electric current to perform co-vapor deposition at deposition rates of 0.1 nm/sec and 0.010 nm/sec, respectively to provide a 40 nm-thick light emitting layer on the hole transport layer.

Further, the heating boat containing BCP was heated by the passage of electric current to perform vapor deposition at a deposition rate of 0.1 nm/sec to provide a 30 nm-thick electron transport layer on the light emitting layer.

Then, lithium fluoride was vapor-deposited to form a cathode buffer layer having a thickness of 0.5 nm, and aluminum was further vapor-deposited to forma cathode having a thickness of 110 nm. In this way, an organic EL element 2-1 was produced.

<Production of Organic EL Elements 2-2 to 2-55>

Organic EL elements 2-2 to 2-55 were produced in the same manner as in the production of the organic EL element 2-1 except that the dopant compound and the host compound were changed to compounds shown in Tables 6 and 7.

TABLE 6

| Organic EL Element No. | Dopant Compound | Host Compound | Rate of Change of Resistance Value (Relative Ratio) | Note |
|---|---|---|---|---|
| 2-1 | (A)-R2 | OC-3 | 100 | Comparative Example |
| 2-2 | (B)-R1 | OC-3 | 102 | Comparative Example |
| 2-3 | (A)-R3 | OC-4 | 22 | Present Invention |
| 2-4 | (A)-R4 | OC-10 | 23 | Present Invention |
| 2-5 | (A)-R4 | OC-27 | 9 | Present Invention |
| 2-6 | (A)-R8 | OC-12 | 10 | Present Invention |
| 2-7 | (A)-R9 | OC-4 | 21 | Present Invention |
| 2-8 | (A)-R9 | OC-11 | 20 | Present Invention |
| 2-9 | (A)-R10 | OC-20 | 19 | Present Invention |
| 2-10 | (A)-R10 | 9 | 22 | Present Invention |
| 2-11 | (A)-R11 | OC-24 | 20 | Present Invention |
| 2-12 | (A)-R25 | OC-24 | 14 | Present Invention |
| 2-13 | (B)-R3 | OC-27 | 22 | Present Invention |
| 2-14 | (B)-R4 | OC-30 | 19 | Present Invention |
| 2-15 | (B)-R11 | OC-32 | 13 | Present Invention |
| 2-16 | (B)-R12 | OC-30 | 26 | Present Invention |
| 2-17 | (B)-R14 | OC-32 | 27 | Present Invention |
| 2-18 | (C)-R3 | 1 | 30 | Present Invention |
| 2-19 | (C)-R4 | 6 | 29 | Present Invention |
| 2-20 | (C)-R8 | 9 | 11 | Present Invention |
| 2-21 | (C)-R10 | 13 | 31 | Present Invention |
| 2-22 | (C)-R11 | 19 | 14 | Present Invention |
| 2-23 | (D)-R3 | 26 | 17 | Present Invention |

TABLE 6-continued

| Organic EL Element No. | Dopant Compound | Host Compound | Rate of Change of Resistance Value (Relative Ratio) | Note |
|---|---|---|---|---|
| 2-24 | (D)-R8 | | 30 | 10 | Present Invention |
| 2-25 | (E)-R3 | | 34 | 18 | Present Invention |
| 2-26 | (E)-R4 | | 53 | 19 | Present Invention |
| 2-27 | (E)-R9 | | 57 | 25 | Present Invention |
| 2-28 | (E)-R10 | | 52 | 23 | Present Invention |
| 2-29 | (E)-R11 | OC-4 | 12 | Present Invention |

TABLE 7

| Organic EL Element No. | Dopant Compound | Host Compound | Rate of Change of Resistance Value (Relative Ratio) | Note |
|---|---|---|---|---|
| 2-30 | (F)-R3 | | 53 | 19 | Present Invention |
| 2-31 | (F)-R4 | OC-11 | 21 | Present Invention |
| 2-32 | (F)-R8 | OC-12 | 11 | Present Invention |
| 2-33 | (F)-R9 | OC-4 | 25 | Present Invention |
| 2-34 | (F)-R10 | OC-32 | 13 | Present Invention |
| 2-35 | (F)-R12 | | 1 | 20 | Present Invention |
| 2-36 | (F)-R14 | OC-24 | 32 | Present Invention |
| 2-37 | (F)-R18 | | 19 | 15 | Present Invention |
| 2-38 | (F)-R25 | OC-27 | 13 | Present Invention |
| 2-39 | (G)-R3 | | 30 | 11 | Present Invention |
| 2-40 | (G)-R4 | | 34 | 12 | Present Invention |
| 2-41 | (G)-R26 | | 53 | 14 | Present Invention |
| 2-42 | (H)-R8 | | 52 | 11 | Present Invention |
| 2-43 | (H)-R9 | | 6 | 19 | Present Invention |
| 2-44 | (H)-R15 | | 57 | 10 | Present Invention |
| 2-45 | (H)-R26 | OC-27 | 29 | Present Invention |
| 2-46 | (I)-R8 | OC-30 | 12 | Present Invention |
| 2-47 | (I)-R10 | | 13 | 18 | Present Invention |
| 2-48 | (J)-R25 | OC-32 | 13 | Present Invention |
| 2-49 | (J)-R2 | OC-20 | 30 | Present Invention |
| 2-50 | (J)-R3 | | 9 | 12 | Present Invention |
| 2-51 | (K)-R9 | OC-24 | 15 | Present Invention |
| 2-52 | (L)-R7 | | 13 | 27 | Present Invention |
| 2-53 | (M)-R3 | | 19 | 15 | Present Invention |
| 2-54 | (O)-R3 | | 19 | 13 | Present Invention |
| 2-55 | (Q)-R2 | OC-27 | 15 | Present Invention |

<Evaluation of Organic EL Elements 2-1 to 2-55>

In order to evaluate each of the obtained organic EL elements, a lighting device such as one shown in FIG. 8 or 9 was produced in the following manner after production of the organic EL element. The non-light emitting surface of the organic EL element was covered with a glass cover. Then, an epoxy-based photo-curable adhesive (LC0629B LUXTRAK manufactured by TOA GOSEI Co., Ltd.) was applied as a sealing agent to the periphery of the glass cover to be brought into contact with the glass substrate on which the organic EL element was produced. Then, the glass cover was placed over the cathode-side of the organic EL element so as to be brought into close contact with the transparent support substrate. Then, a portion other than the organic EL element was irradiated with UV light from the glass substrate side to cure the adhesive to seal the organic EL element. The resistance value of the light-emitting layer was measured by an impedance spectrometer.

[Measurement of Rate of Change of Resistance Value of Light-Emitting Layer of Organic EL Element by Impedance Spectrometry]

Based on a measurement method described in pages 423 to 425 of "Handbook of Thin Film Characterization Technology" published by Technosystem Co., Ltd., the resistance value of light-emitting layer of the produced organic EL element was measured using Impedance Analyzer 1260 and Dielectric Interface 1296 manufactured by Solartron.

The resistance values of the light-emitting layer were measured before and after the organic EL element was driven for 1000 hours under conditions of room temperature (25° C.) and a constant current of 2.5 mA/cm$^2$, and the rate of change of the resistance value was determined from the measurement results by calculation using the following calculating formula. Tables 6 and 7 show relative ratios determined by taking the rate of change of the resistance value of the organic EL element 2-1 as 100.

Rate of change of resistance value before and after driving=|(resistance value after driving/resistance value before driving)−1|×100

The closer to 0 the value of the rate of change is, the smaller the rate of change before and after driving is.

As can be seen from Tables 6 and 7, the organic EL elements using the iridium complex according to the present invention had a smaller rate of change of the resistance value of the light-emitting layer and a longer emission lifetime than the organic EL elements of comparative examples.

REFERENCE SIGNS LIST

1 Display
3 Pixel
5 Scan line
6 Data line
7 Power-supply line
10 Organic EL Element
11 Switching transistor
12 Driving transistor
13 Capacitor
101 Organic EL element in lighting device
102 Glass cover
105 Cathode
106 Organic EL layer
107 Glass substrate with transparent electrode
108 Nitrogen gas
109 Moisture capturing agent 201 Glass substrate
202 ITO transparent electrode
203 Partition wall
204 Hole injection layer
205B, 205G, 205R Light-emitting layer
206 Cathode
A Display unit
B Control unit

The invention claimed is:

1. An iridium complex having a coefficient of external influence of 0.73 Å²/MW or less as defined by the following definition equation:

Coefficient of external influence (Svdw)=Van der Waals surface area [Å²]/molecular weight (MW), and the iridium complex having a partial structure represented by General Formula (2):

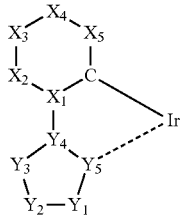

wherein a carbon atom and $X_1$ to $X_5$ are a group of atoms forming a 6-membered aromatic ring selected from a benzene ring or a pyridine ring,
each of $X_1$, $X_2$, $X_4$, and $X_5$ is a carbon atom,
$X_3$ is a carbon atom or a nitrogen atom,
$Y_1$ to $Y_5$ are a group of atoms forming a nitrogen atom-containing 5-membered aromatic ring selected from an imidazole ring or a pyrazole ring,
$Y_1$ to $Y_4$ are carbon atoms or nitrogen atoms, and $Y_5$ is a nitrogen atom,
when $X_3$ is a nitrogen atom, $Y_4$ is a carbon atom,
when $Y_4$ is a nitrogen atom, $X_3$ is a carbon atom,
when $X_3$ is a nitrogen atom, $Y_3$ is a nitrogen atom and unsubstituted, and
at least one of $X_5$ and $Y_1$ is a carbon atom or nitrogen atom having a substituent R3:

when $X_3$ is a nitrogen atom, $Y_1$, $Y_2$, and $Y_4$ are carbon atoms, and $Y_3$ and $Y_5$ are nitrogen atoms, $Y_1$ is unsubstituted with $CF_3$.

2. The iridium complex according to claim 1, wherein in the general formula (2), at least one of the atoms represented by $X_5$ and $Y_1$ is a carbon atom having a substituent group, and wherein the substituent group is a trifluoromethyl group.

3. A method for producing the iridium complex according to claim 1, comprising synthesizing the iridium complex by a solvent-free reaction using, as an alternative to a reaction solvent, an organic compound serving as a ligand of the iridium complex.

4. The method for producing the iridium complex according to claim 3, wherein a 6-coordinated iridium complex is formed by coordination of ligands to iridium, and then a substituent group is introduced into the ligands of the iridium complex.

5. An organic electroluminescent element comprising at least one organic layer sandwiched between an anode and a cathode, an iridium complex contained in the at least one organic layer, and the iridium complex being the iridium complex according to claim 1.

6. A display device comprising the organic electroluminescent element according to claim 5.

7. A lighting device comprising the organic electroluminescent element according to claim 5.

8. The iridium complex according to claim 1, wherein $X_3$ is a carbon atom.

9. The iridium complex according to claim 1, wherein $Y_3$ is a carbon atom when $Y_2$ is a nitrogen atom, and $Y_2$ is a carbon atom when $Y_3$ is a nitrogen atom.

10. The iridium complex according to claim 1, wherein $X_2$, $X_3$, and $X_4$ are unsubstituted.

* * * * *